(12) United States Patent
Parella et al.

(10) Patent No.: US 11,174,500 B2
(45) Date of Patent: Nov. 16, 2021

(54) METHODS FOR PURIFICATION OF MESSENGER RNA

(71) Applicant: Translate Bio, Inc., Lexington, MA (US)

(72) Inventors: Joseph Parella, Lexington, MA (US); Kimberly Gillis, Lexington, MA (US); Jonathan Abysalh, Lexington, MA (US); Travis Jeannotte, Lexington, MA (US); Erik Held, Lexington, MA (US); Frank DeRosa, Lexington, MA (US); Michael Heartlein, Lexington, MA (US); Rebecca Powell, Lexington, MA (US)

(73) Assignee: Translate Bio, Inc., Lexington, MA (US)

(*) Notice: Subject to any disclaimer, the term of this patent is extended or adjusted under 35 U.S.C. 154(b) by 162 days.

(21) Appl. No.: 16/551,340

(22) Filed: Aug. 26, 2019

(65) Prior Publication Data

US 2020/0095571 A1    Mar. 26, 2020

Related U.S. Application Data

(60) Provisional application No. 62/722,674, filed on Aug. 24, 2018.

(51) Int. Cl.
| | |
|---|---|
| C12N 15/10 | (2006.01) |
| C12P 19/34 | (2006.01) |
| C07H 21/02 | (2006.01) |
| C07H 1/06 | (2006.01) |

(52) U.S. Cl.
CPC ............... *C12P 19/34* (2013.01); *C07H 1/06* (2013.01); *C07H 21/02* (2013.01); *C12N 15/1003* (2013.01); *C12N 15/1017* (2013.01)

(58) Field of Classification Search
CPC ..... C12P 19/34; C07H 21/02; C12N 15/1003; C12N 15/1017
See application file for complete search history.

(56) References Cited

U.S. PATENT DOCUMENTS

| | | |
|---|---|---|
| 2,647,121 A | 7/1953 | Jacoby |
| 2,717,909 A | 9/1955 | Kosmin |
| 2,819,718 A | 1/1958 | Goldman |
| 2,844,629 A | 7/1958 | William et al. |
| 3,096,560 A | 7/1963 | Liebig |

(Continued)

FOREIGN PATENT DOCUMENTS

| | | |
|---|---|---|
| CA | 2518132 A1 | 3/2006 |
| CA | 2807552 A1 | 2/2012 |

(Continued)

OTHER PUBLICATIONS

Piexoto et al., "Purification by membrane technology of an intracellular Ehrlichia ruminantium candidate vaccine against heartwater" Process Biochemistry vol. 42 pp. 1084-1089 (Year: 2007).*

(Continued)

*Primary Examiner* — Eric Olson
(74) *Attorney, Agent, or Firm* — Proskauer Rose LLP; Fangli Chen; Nicholas C. Prairie

(57) ABSTRACT

The present invention provides, among other things, methods for purifying mRNA based on normal flow filtration for therapeutic use.

25 Claims, 21 Drawing Sheets

(56) References Cited

U.S. PATENT DOCUMENTS

| | | |
|---|---|---|
| 3,535,289 A | 10/1970 | Yoshihara et al. |
| 3,614,954 A | 10/1971 | Mirowski et al. |
| 3,614,955 A | 10/1971 | Mirowski |
| 3,656,185 A | 4/1972 | Carpentier |
| 3,805,301 A | 4/1974 | Liebig |
| 3,945,052 A | 3/1976 | Liebig |
| 3,995,623 A | 12/1976 | Blake et al. |
| 4,013,507 A | 3/1977 | Rembaum |
| 4,072,146 A | 2/1978 | Howes |
| 4,096,860 A | 6/1978 | McLaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,737,323 A | 4/1988 | Martin et al. |
| 4,762,915 A | 8/1988 | Kung et al. |
| 4,782,836 A | 11/1988 | Alt |
| 4,843,155 A | 6/1989 | Chomczynski et al. |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |
| 4,920,016 A | 4/1990 | Allen et al. |
| 4,946,683 A | 8/1990 | Forssen |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,194,654 A | 3/1993 | Hostetler et al. |
| 5,200,395 A | 4/1993 | Eto et al. |
| 5,223,263 A | 6/1993 | Hostetler et al. |
| 5,261,419 A | 11/1993 | Osypka |
| 5,264,618 A | 11/1993 | Felgner et al. |
| 5,279,833 A | 1/1994 | Rose |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,552,155 A | 9/1996 | Bailey et al. |
| 5,595,756 A | 1/1997 | Bally et al. |
| 5,607,385 A | 3/1997 | Francischelli et al. |
| 5,609,624 A | 3/1997 | Kalis |
| 5,610,283 A | 3/1997 | Buechler |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,677,124 A | 10/1997 | DuBois et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,783,383 A | 7/1998 | Kondo et al. |
| 5,844,107 A | 12/1998 | Hanson et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler et al. |
| 5,976,569 A | 11/1999 | Milstein |
| 5,981,501 A | 11/1999 | Wheeler et al. |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,147,055 A | 11/2000 | Hobart et al. |
| 6,152,955 A | 11/2000 | KenKnight et al. |
| 6,165,763 A | 12/2000 | Brown et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,210,892 B1 | 4/2001 | Bennett et al. |
| 6,214,804 B1 | 4/2001 | Felgner et al. |
| 6,271,208 B1 | 8/2001 | Bischoff |
| 6,271,209 B1 | 8/2001 | Smith et al. |
| 6,287,591 B1 | 9/2001 | Semple et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,417,326 B1 | 7/2002 | Cullis et al. |
| 6,485,726 B1 | 11/2002 | Blumberg et al. |
| 6,534,484 B1 | 3/2003 | Wheeler et al. |
| 6,585,410 B1 | 7/2003 | Ryan |
| 6,586,410 B1 | 7/2003 | Wheeler et al. |
| 6,670,178 B1 | 12/2003 | Selden et al. |
| 6,696,424 B1 | 2/2004 | Wheeler |
| 6,733,777 B2 | 5/2004 | Erbacher et al. |
| 6,743,823 B1 | 6/2004 | Summar et al. |
| 6,756,055 B2 | 6/2004 | McDonald et al. |
| 6,790,838 B2 | 9/2004 | Alison et al. |
| 6,815,432 B2 | 11/2004 | Wheeler et al. |
| 6,821,530 B2 | 11/2004 | Koob et al. |
| 6,835,395 B1 | 12/2004 | Semple et al. |
| 6,858,224 B2 | 2/2005 | Wheeler et al. |
| 6,858,225 B2 | 2/2005 | Semple et al. |
| 6,887,665 B2 | 5/2005 | Trulson et al. |
| 6,986,902 B1 | 1/2006 | Chen et al. |
| 6,998,115 B2 | 2/2006 | Langer et al. |
| 7,022,214 B2 | 4/2006 | Olech |
| 7,067,697 B2 | 6/2006 | Gao |

(56) References Cited

U.S. PATENT DOCUMENTS

| | | | |
|---|---|---|---|
| 7,084,303 B2 | 8/2006 | Watanabe et al. |
| 7,341,738 B2 | 3/2008 | Semple et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,745,651 B2 | 6/2010 | Heyes et al. |
| 7,767,399 B2 | 8/2010 | Murphy et al. |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 7,972,435 B2 | 7/2011 | Bury et al. |
| 8,021,686 B2 | 9/2011 | Semple et al. |
| 8,071,082 B2 | 12/2011 | Zugates et al. |
| 8,075,780 B2 | 12/2011 | Pearce |
| 8,101,741 B2 | 1/2012 | MacLachlan et al. |
| 8,106,022 B2 | 1/2012 | Manoharan et al. |
| 8,158,601 B2 | 4/2012 | Chen et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |
| 8,329,070 B2 | 12/2012 | MacLachlan et al. |
| 8,450,298 B2 | 5/2013 | Mahon et al. |
| 8,450,467 B2 | 5/2013 | Manoharan et al. |
| 8,470,585 B2 | 6/2013 | de Vocht et al. |
| 8,513,403 B2 | 8/2013 | MacLachlan et al. |
| 8,557,231 B2 | 10/2013 | Langer et al. |
| 8,562,966 B2 | 10/2013 | Zugates et al. |
| 8,569,256 B2 | 10/2013 | Heyes et al. |
| 8,652,512 B2 | 2/2014 | Schmehl et al. |
| 8,691,966 B2 | 4/2014 | Kariko et al. |
| 8,710,200 B2 | 4/2014 | Schrum et al. |
| 8,748,089 B2 | 6/2014 | Kariko et al. |
| 8,802,644 B2 | 8/2014 | Chen et al. |
| 8,808,681 B2 | 8/2014 | Anderson et al. |
| 8,808,982 B2 | 8/2014 | Dahl et al. |
| 8,822,663 B2 | 9/2014 | Schrum et al. |
| 8,828,956 B2 | 9/2014 | Manoharan et al. |
| 8,835,108 B2 | 9/2014 | Kariko et al. |
| 8,846,348 B2 | 9/2014 | Jendrisak et al. |
| 8,853,377 B2 | 10/2014 | Guild et al. |
| 8,859,229 B2 | 10/2014 | Rabinovich et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,980,864 B2 | 3/2015 | Hoge et al. |
| 8,999,351 B2 | 4/2015 | Manoharan et al. |
| 8,999,950 B2 | 4/2015 | MacLachlan et al. |
| 9,012,219 B2 | 4/2015 | Kariko et al. |
| 9,012,498 B2 | 4/2015 | Manoharan et al. |
| 9,018,187 B2 | 4/2015 | Heyes et al. |
| 9,051,567 B2 | 6/2015 | Fitzgerald et al. |
| 9,061,059 B2 | 6/2015 | Chakraborty et al. |
| 9,074,208 B2 | 7/2015 | Maclachlan et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,404,127 B2 | 8/2016 | Yaworski et al. |
| 9,428,751 B2 | 8/2016 | MacDonald et al. |
| 9,254,311 B2 | 9/2016 | Bancel et al. |
| 9,464,124 B2 | 10/2016 | Bancel et al. |
| 9,492,386 B2 | 11/2016 | Maclachlan et al. |
| 9,504,734 B2 | 11/2016 | Bancel et al. |
| 9,518,272 B2 | 12/2016 | Yaworski et al. |
| 9,580,734 B2 | 2/2017 | Shanker et al. |
| 9,850,269 B2 * | 12/2017 | DeRosa ............... C07H 21/00 |
| 9,957,499 B2 * | 5/2018 | Heartlein ............. A61P 43/00 |
| 10,155,785 B2 * | 12/2018 | DeRosa ............. C12N 15/1017 |
| 2001/0047091 A1 | 11/2001 | Miki |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0082154 A1 | 5/2003 | Leamon |
| 2003/0083272 A1 | 5/2003 | Wiederholt et al. |
| 2003/0104044 A1 | 6/2003 | Semple et al. |
| 2003/0181410 A1 | 9/2003 | Wheeler et al. |
| 2003/0186237 A1 | 10/2003 | Ginsberg |
| 2003/0215395 A1 | 11/2003 | Yu et al. |
| 2004/0110709 A1 | 6/2004 | Li et al. |
| 2004/0132683 A1 | 7/2004 | Felgner et al. |
| 2004/0142025 A1 | 7/2004 | Maclachlan et al. |
| 2004/0224912 A1 | 11/2004 | Dobie et al. |
| 2004/0235982 A1 | 11/2004 | Rabasco et al. |
| 2005/0004058 A1 | 1/2005 | Benoit et al. |
| 2005/0008689 A1 | 1/2005 | Semple et al. |
| 2005/0032730 A1 | 2/2005 | Von Der Mulbe et al. |
| 2005/0054026 A1 | 3/2005 | Atsushi et al. |
| 2005/0059005 A1 | 3/2005 | Tuschl et al. |
| 2005/0059024 A1 | 3/2005 | Conrad |
| 2005/0059624 A1 | 3/2005 | Hoerr et al. |
| 2005/0065107 A1 | 3/2005 | Hobart et al. |
| 2005/0069590 A1 | 3/2005 | Buehler et al. |
| 2005/0079212 A1 | 4/2005 | Wheeler et al. |
| 2005/0112755 A1 | 5/2005 | Pearce |
| 2005/0143332 A1 | 6/2005 | Monahan et al. |
| 2005/0148786 A1 | 7/2005 | Ikeda et al. |
| 2005/0158302 A1 | 7/2005 | Faustman et al. |
| 2005/0226847 A1 | 10/2005 | Coffin |
| 2005/0244961 A1 | 11/2005 | Short et al. |
| 2005/0250723 A1 | 11/2005 | Hoerr et al. |
| 2006/0008910 A1 | 1/2006 | MacLachlan et al. |
| 2006/0051771 A1 | 3/2006 | Murphy |
| 2006/0059576 A1 | 3/2006 | Pasinetti et al. |
| 2006/0069225 A1 | 3/2006 | Wintermantel et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2006/0216343 A1 | 9/2006 | Panzner et al. |
| 2006/0223939 A1 | 10/2006 | Lange et al. |
| 2006/0228404 A1 | 10/2006 | Anderson et al. |
| 2006/0241071 A1 | 10/2006 | Grinstaff et al. |
| 2006/0246434 A1 | 11/2006 | Erlander et al. |
| 2007/0135372 A1 | 6/2007 | Maclachlan et al. |
| 2007/0142628 A1 | 6/2007 | Ghoshal et al. |
| 2007/0172950 A1 | 7/2007 | Wheeler et al. |
| 2007/0252295 A1 | 11/2007 | Panzner et al. |
| 2007/0275923 A1 | 11/2007 | Chen et al. |
| 2007/0281336 A1 | 12/2007 | Jendrisak et al. |
| 2008/0113357 A1 | 5/2008 | Baggio |
| 2008/0145338 A1 | 6/2008 | Anderson et al. |
| 2008/0160048 A1 | 7/2008 | Fuller |
| 2008/0242626 A1 | 10/2008 | Zugates et al. |
| 2008/0248559 A1 | 10/2008 | Inomata et al. |
| 2008/0260706 A1 | 10/2008 | Rabinovich et al. |
| 2009/0023673 A1 | 1/2009 | Manoharan et al. |
| 2009/0093433 A1 | 4/2009 | Woolf et al. |
| 2009/0163705 A1 | 6/2009 | Manoharan et al. |
| 2009/0186805 A1 | 7/2009 | Tabor et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2009/0286852 A1 | 11/2009 | Kariko et al. |

(56) References Cited

U.S. PATENT DOCUMENTS

| | | |
|---|---|---|
| 2009/0326051 A1 | 12/2009 | Corey et al. |
| 2010/0028943 A1 | 2/2010 | Thomas et al. |
| 2010/0035249 A1 | 2/2010 | Hayashizaki et al. |
| 2010/0036084 A1 | 2/2010 | Langer et al. |
| 2010/0041152 A1 | 2/2010 | Wheeler et al. |
| 2010/0047261 A1 | 2/2010 | Hoerr et al. |
| 2010/0092572 A1 | 4/2010 | Kaeuper et al. |
| 2010/0120129 A1 | 5/2010 | Amshey et al. |
| 2010/0178699 A1 | 7/2010 | Gao et al. |
| 2010/0189729 A1 | 7/2010 | Hoerr et al. |
| 2010/0267806 A1 | 10/2010 | Bumcrot et al. |
| 2010/0331234 A1 | 12/2010 | Mahon et al. |
| 2011/0009641 A1 | 1/2011 | Anderson et al. |
| 2011/0038941 A1 | 2/2011 | Lee et al. |
| 2011/0092739 A1 | 4/2011 | Chen et al. |
| 2011/0143397 A1 | 6/2011 | Kariko et al. |
| 2011/0159550 A1 | 6/2011 | Sanders |
| 2011/0200582 A1 | 8/2011 | Baryza et al. |
| 2011/0236391 A1 | 9/2011 | Mahler et al. |
| 2011/0244026 A1 | 10/2011 | Guild et al. |
| 2011/0256175 A1 | 10/2011 | Hope et al. |
| 2011/0293703 A1 | 12/2011 | Mahon et al. |
| 2011/0311583 A1 | 12/2011 | Manoharan et al. |
| 2012/0007803 A1 | 1/2012 | Takatsuka |
| 2012/0009222 A1 | 1/2012 | Nguyen et al. |
| 2012/0060237 A1 | 3/2012 | Wu et al. |
| 2012/0065252 A1 | 3/2012 | Schrum et al. |
| 2012/0065358 A1 | 3/2012 | Langer et al. |
| 2012/0114831 A1 | 5/2012 | Semple et al. |
| 2012/0128760 A1 | 5/2012 | Manoharan et al. |
| 2012/0129910 A1 | 5/2012 | Thompson et al. |
| 2012/0142756 A1 | 6/2012 | Guild et al. |
| 2012/0174256 A1 | 7/2012 | Kato et al. |
| 2012/0195936 A1 | 8/2012 | Rudolph et al. |
| 2012/0202871 A1 | 8/2012 | Heyes et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2012/0328668 A1 | 12/2012 | Maclachlan et al. |
| 2013/0004992 A1 | 1/2013 | Lin et al. |
| 2013/0017223 A1 | 1/2013 | Hope et al. |
| 2013/0158021 A1 | 6/2013 | Dong et al. |
| 2013/0195967 A1 | 8/2013 | Guild et al. |
| 2013/0224824 A1 | 8/2013 | Shigemori et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2013/0337045 A1 | 12/2013 | Bredehorst et al. |
| 2013/0337528 A1 | 12/2013 | Thompson et al. |
| 2013/0337579 A1 | 12/2013 | Lee et al. |
| 2014/0010861 A1 | 1/2014 | Bancel et al. |
| 2014/0044772 A1 | 2/2014 | MacLachlan et al. |
| 2014/0093952 A1 | 4/2014 | Serway |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0162897 A1 | 6/2014 | Grunenwald et al. |
| 2014/0171485 A1 | 6/2014 | Bancel et al. |
| 2014/0179756 A1 | 6/2014 | Maclachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200163 A1 | 7/2014 | Mikkelsen et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221248 A1 | 8/2014 | Jendrisak et al. |
| 2014/0221465 A1 | 8/2014 | Bancel et al. |
| 2014/0227300 A1 | 8/2014 | Chin et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0294938 A1 | 10/2014 | Guild et al. |
| 2014/0294939 A1 | 10/2014 | Guild et al. |
| 2014/0294940 A1 | 10/2014 | Guild et al. |
| 2014/0329884 A1 | 11/2014 | Dong et al. |
| 2014/0343129 A1 | 11/2014 | de Fougerolles et al. |
| 2014/0363876 A1 | 12/2014 | Jendrisak et al. |
| 2015/0004217 A1 | 1/2015 | Guild et al. |
| 2015/0005372 A1 | 1/2015 | Hoge et al. |
| 2015/0011615 A1 | 1/2015 | Manoharan et al. |
| 2015/0011633 A1 | 1/2015 | Shorr et al. |
| 2015/0017211 A1 | 1/2015 | de Fougerolles et al. |
| 2015/0038556 A1 | 2/2015 | Heartlein et al. |
| 2015/0038558 A1 | 2/2015 | Kariko et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0110857 A1 | 4/2015 | DeRosa et al. |
| 2015/0110858 A1 | 4/2015 | DeRosa et al. |
| 2015/0110859 A1 | 4/2015 | Heartlein et al. |
| 2015/0111248 A1 | 4/2015 | Bancel et al. |
| 2015/0111945 A1 | 4/2015 | Geisbert et al. |
| 2015/0119444 A1 | 4/2015 | Manoharan et al. |
| 2015/0119445 A1 | 4/2015 | Manoharan et al. |
| 2015/0157565 A1 | 6/2015 | Heartlein et al. |
| 2015/0166465 A1 | 6/2015 | Chen et al. |
| 2015/0190515 A1 | 7/2015 | Manoharan et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2015/0376220 A1 | 12/2015 | DeRosa et al. |
| 2016/0024139 A1 | 1/2016 | Berlanda Scorza et al. |
| 2016/0011548 A1 | 4/2016 | Maclachlan et al. |
| 2016/0095924 A1 | 4/2016 | Hoge et al. |
| 2016/0114011 A1 | 4/2016 | Bancel et al. |
| 2016/0115477 A1 | 4/2016 | Maclachlan et al. |
| 2016/0136236 A1 | 5/2016 | Hoge et al. |
| 2016/0151284 A1 | 6/2016 | Heves et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |

(56) References Cited

U.S. PATENT DOCUMENTS

| | | |
|---|---|---|
| 2016/0304552 A1 | 10/2016 | Roy et al. |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |
| 2016/0367702 A1 | 12/2016 | Hoge et al. |
| 2016/0375134 A1 | 12/2016 | Bancel et al. |
| 2016/0375137 A9 | 12/2016 | Manoharan et al. |
| 2017/0002060 A1 | 1/2017 | Bolen et al. |
| 2017/0007702 A1 | 1/2017 | Heyes et al. |

FOREIGN PATENT DOCUMENTS

| | | |
|---|---|---|
| CN | 1399561 | 2/2003 |
| CN | 100569877 C | 12/2009 |
| CN | 101863544 A | 10/2010 |
| DE | 24 30 998 A1 | 1/1975 |
| DE | 2520814 A1 | 11/1976 |
| DE | 3728917 A1 | 3/1989 |
| EP | 6 73 637 A1 | 9/1995 |
| EP | 0783297 A1 | 7/1997 |
| EP | 0853123 A1 | 7/1998 |
| EP | 0959092 A1 | 11/1999 |
| EP | 1519714 B1 | 4/2005 |
| EP | 1979364 A2 | 10/2008 |
| EP | 2045251 A1 | 4/2009 |
| EP | 2338478 B1 | 6/2011 |
| EP | 2449106 A1 | 5/2012 |
| EP | 2532649 A1 | 12/2012 |
| EP | 2578685 A2 | 4/2013 |
| EP | 2823809 A1 | 1/2015 |
| FR | 1 378 382 A | 11/1964 |
| FR | 2 235 112 A1 | 1/1975 |
| GB | 1072118 A | 6/1967 |
| GB | 1602085 A | 11/1981 |
| JP | H07-053535 | 2/1955 |
| JP | S48-022365 | 3/1973 |
| JP | S49-127908 A | 12/1974 |
| JP | S51-023537 | 2/1976 |
| JP | 51-125144 | 11/1976 |
| JP | S52-010847 | 1/1977 |
| JP | S63125144 A | 5/1988 |
| JP | 63-154788 | 6/1988 |
| JP | H09-505593 A | 6/1997 |
| JP | H10-197978 A | 7/1998 |
| JP | 11-005786 A | 1/1999 |
| JP | 11-080142 | 3/1999 |
| JP | 2001-523215 A | 11/2001 |
| JP | 2002-167368 A | 6/2002 |
| JP | 2003-519199 A | 6/2003 |
| JP | 4-108173 B2 | 6/2008 |
| JP | 2008-247749 A | 10/2008 |
| JP | 2010/053108 | 3/2010 |
| JP | 50-24216 B2 | 9/2012 |
| WO | WO-1992/004970 A1 | 4/1992 |
| WO | WO-93/18229 A1 | 9/1993 |
| WO | WO-93/18754 A1 | 9/1993 |
| WO | WO-95/11004 A1 | 4/1995 |
| WO | WO-95/14651 A1 | 6/1995 |
| WO | WO-95/27478 A1 | 10/1995 |
| WO | WO-96/18372 A2 | 6/1996 |
| WO | WO-96/26179 A1 | 8/1996 |
| WO | WO-96/37211 A1 | 11/1996 |
| WO | WO-96/40964 A2 | 12/1996 |
| WO | WO-97/46223 A1 | 12/1997 |
| WO | WO-1998/005673 A1 | 2/1998 |
| WO | WO-98/10748 A1 | 3/1998 |
| WO | WO-98/16202 A2 | 4/1998 |
| WO | WO-1998/030685 A2 | 7/1998 |
| WO | WO-98/51278 A2 | 11/1998 |
| WO | WO-00/03044 A1 | 1/2000 |
| WO | WO-00/62813 A2 | 10/2000 |
| WO | WO-00/64484 A2 | 11/2000 |
| WO | WO-00/69913 A1 | 11/2000 |
| WO | WO-01/05375 A1 | 1/2001 |
| WO | WO-01/07599 A1 | 2/2001 |
| WO | WO-02/22709 A1 | 3/2002 |
| WO | WO-02/31025 A2 | 4/2002 |
| WO | WO-02/34236 A2 | 5/2002 |
| WO | WO-02/42317 A2 | 5/2002 |
| WO | WO-2003/033739 | 4/2003 |
| WO | WO-03/040288 A2 | 5/2003 |
| WO | WO-03/070735 A2 | 8/2003 |
| WO | WO-2004/043588 A2 | 5/2004 |
| WO | WO-2004/048345 A2 | 6/2004 |
| WO | WO-2004/106411 A2 | 12/2004 |
| WO | WO-2005/026372 A1 | 3/2005 |
| WO | WO-2005/028619 A2 | 3/2005 |
| WO | WO-2005/037226 A2 | 4/2005 |
| WO | WO-2005/058933 | 6/2005 |
| WO | WO-2005/121348 A1 | 12/2005 |
| WO | WO-2006/000448 A2 | 1/2006 |
| WO | WO-2006/016097 A2 | 2/2006 |
| WO | WO-2006/082088 A1 | 8/2006 |
| WO | WO-2006/105043 A2 | 10/2006 |
| WO | WO-2006/138380 A2 | 12/2006 |
| WO | WO-2007/024708 A2 | 3/2007 |
| WO | WO-2007/031091 A2 | 3/2007 |
| WO | WO-2007/120863 A2 | 10/2007 |
| WO | WO-2007/126386 A1 | 11/2007 |
| WO | WO-2007/143659 A2 | 12/2007 |
| WO | WO-2008/011561 A2 | 1/2008 |
| WO | WO-2008/042973 A2 | 4/2008 |
| WO | WO-2008/083949 A2 | 7/2008 |
| WO | WO-2008/113364 A2 | 9/2008 |
| WO | WO-2009/046220 A2 | 4/2009 |
| WO | WO-2009/093142 | 7/2009 |
| WO | WO-2009/127060 A1 | 10/2009 |
| WO | WO-2009/127230 A1 | 10/2009 |
| WO | WO-2010/042877 A1 | 4/2010 |
| WO | WO-2010/045512 A2 | 4/2010 |
| WO | WO-2010/053572 A2 | 5/2010 |
| WO | WO-2010/054401 A1 | 5/2010 |
| WO | WO-2010/054405 A1 | 5/2010 |
| WO | WO-2010/056403 A1 | 5/2010 |
| WO | WO-2010/099387 A1 | 9/2010 |
| WO | WO-2010/114789 A1 | 10/2010 |
| WO | WO-2010/119256 A1 | 10/2010 |
| WO | WO-2010/129709 A1 | 11/2010 |
| WO | WO-2010/144740 A1 | 12/2010 |
| WO | WO-2010/147992 A1 | 12/2010 |
| WO | WO-2010/148013 A2 | 12/2010 |
| WO | WO-2011/012746 A2 | 2/2011 |
| WO | WO-2011/039144 A1 | 4/2011 |
| WO | WO-2011/068810 A1 | 6/2011 |
| WO | WO-2011/075656 A1 | 6/2011 |
| WO | WO-2011/141705 A1 | 11/2011 |
| WO | WO-2012/019168 A2 | 2/2012 |
| WO | WO-2012/019630 A1 | 2/2012 |
| WO | WO-2012/019780 A1 | 2/2012 |
| WO | WO-2012/027675 A2 | 3/2012 |
| WO | WO-2012/045075 A1 | 4/2012 |
| WO | WO-2012/045082 A2 | 4/2012 |
| WO | WO-2012/075040 A2 | 6/2012 |
| WO | WO-2012/077080 A1 | 6/2012 |
| WO | WO-2012/133737 A1 | 10/2012 |
| WO | WO-2012/135025 A2 | 10/2012 |
| WO | WO-2012/135805 A2 | 10/2012 |
| WO | WO-2012/170889 A1 | 12/2012 |
| WO | WO-2012/170930 A1 | 12/2012 |
| WO | WO-2013/039857 A1 | 3/2013 |
| WO | WO-2013/039861 A2 | 3/2013 |
| WO | WO-2013/063468 A1 | 5/2013 |
| WO | WO-2013/090186 A1 | 6/2013 |
| WO | WO-2013/101690 A1 | 7/2013 |
| WO | WO-2013/102203 A1 | 7/2013 |
| WO | WO-2013/126803 A1 | 8/2013 |
| WO | WO-2013/130161 A1 | 9/2013 |
| WO | WO-2013/149140 A1 | 10/2013 |

(56) References Cited

FOREIGN PATENT DOCUMENTS

| | | |
|---|---|---|
| WO | WO-2013/149141 A1 | 10/2013 |
| WO | WO-2013/151663 A1 | 10/2013 |
| WO | WO-2013/151664 A1 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/185067 A1 | 12/2013 |
| WO | WO-2013/185069 A1 | 12/2013 |
| WO | WO-2014/028487 A1 | 2/2014 |
| WO | WO-2014/089486 A1 | 6/2014 |
| WO | WO-2014/113089 A2 | 7/2014 |
| WO | WO-2014/144039 A1 | 9/2014 |
| WO | WO-2014/144196 A1 | 9/2014 |
| WO | WO-2014/144711 A1 | 9/2014 |
| WO | WO-2014/144767 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/152774 A1 | 9/2014 |
| WO | WO-2014/152940 A1 | 9/2014 |
| WO | WO-2014/152966 A1 | 9/2014 |
| WO | WO-2014/153052 A2 | 9/2014 |
| WO | WO-2014/158795 A1 | 10/2014 |
| WO | WO-2014/159813 A1 | 10/2014 |
| WO | WO-2014/179562 A1 | 11/2014 |
| WO | WO-2014/210356 A1 | 12/2014 |
| WO | WO-2015/006747 A2 | 1/2015 |
| WO | WO-2015/011633 A1 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO-2015/085318 A2 | 6/2015 |
| WO | WO-2015/089511 A2 | 6/2015 |
| WO | WO-2016/054421 A1 | 4/2016 |
| WO | WO-2016/071857 A1 | 5/2016 |
| WO | WO-2016/077123 A1 | 5/2016 |
| WO | WO-2016/077125 A1 | 5/2016 |
| WO | WO-2016/118724 A1 | 7/2016 |
| WO | WO-2016/118725 A1 | 7/2016 |
| WO | WO-2016/154127 A2 | 9/2016 |
| WO | WO-2016/164762 A1 | 10/2016 |
| WO | WO-2016/183366 A2 | 11/2016 |
| WO | WO-2016/193206 A1 | 12/2016 |
| WO | WO-2016/197132 A1 | 12/2016 |
| WO | WO-2016/197133 A1 | 12/2016 |
| WO | WO-2016/201377 A1 | 12/2016 |
| WO | WO-2017/149139 A1 | 9/2017 |
| WO | WO-2018/157133 A1 | 8/2018 |
| WO | WO-2018/157141 A1 | 8/2018 |
| WO | WO-2019/207060 | 10/2019 |
| WO | WO2019/227095 | * 11/2019 ............ B01D 63/06 |

OTHER PUBLICATIONS

U.S. Appl. No. 60/083,294, filed Apr. 28, 1998, Chen et al.
U.S. Appl. No. 61/494,714, filed Jun. 8, 2011, Guild et al.
U.S. Appl. No. 61/494,745, filed Jun. 8, 2011, Guild et al.
U.S. Appl. No. 61/494,881, filed Jun. 8, 2011, Guild et al.
U.S. Appl. No. 61/494,882, filed Jun. 8, 2011, Zhang et al.
Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Alton, E.W.F.W. et al., Cationic Lipid-Mediated CFTR Gene Transfer to the Lungs and Nose of Patients with Cystic Fibrosis: a Double-Blind Placebo-Controlled Trial, Lancet, 353:947-954 (1999).
Anderson, D.G. et al., Structure/property studies of polymeric gene delivery using a library of poly(beta-amino esters). Molecular Therapy 11(3):426-434 (2005).
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).
Anderson, J. Biological Responses to Materials. Annual Review of Materials Research 31:81-110 (2001).
Anderson, W. French, Human gene therapy, Nature, 392, 25-30 (1998).
Andries, O. et al., Comparison of the Gene Transfer Efficiency of mRNA/GL67 and pDNA/GL67 Complexes in Respiratory Cells, Mol. Pharmaceut., 9: 2136-2145 (2012).
Auffray, C. et al., Purification of Mouse Immunoglubulin Heavy-Chain Messenger RNAs from Total Myeloma Tumor RNA, European Journal of Biochemistry, 107(2):303-314 (1980).
Author Unknown, Blood Proteins, published by WikiPedia, San Francisco, CA, 2 pages, <http://en.wikipedia.org/wiki/Biood_proteins> downloaded May 17, 2015.
Bahlke, M. A. et al., Progress towards in vivo use of siRNAs, Molecular Therapy, 13:644-670 (2006).
Bajaj, A. et al., Synthesis and gene transfection efficacies of PEI-cholesterol-based lipopolymers. Bioconjugate Chemistry 19(8):1640-516511 (2008).
Barreau, C. et al., Liposome-mediated RNA transfection should be used with caution, RNA, 12:1790-1793 (2006).
Behr, J. et al., Efficient Gene Transfer into Mammalian Primary Endocrine Cells with Lipo Polyamine-Coated DNA, Proc. Nat.'l Acad. Sci., 86: 6982-6986 (1989).
Bennett, J. Immune response following intraocular delivery of recombinant viral vectors, Gene Therapy, 10: 977-982 (2003).
Bloomfield, V.A., Quasi-Elastic Light Scattering Applications in Biochemistry and Biology, Ann. Rev. Biophys. Bioeng. 10:421-450 (1981).
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., Structure/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Budker, V. et al., Protein/Amphipathic Polyamine Complexes Enable Highly Efficient Transfection with Minimal Toxicity, BioTechniques, 23: 139-147 (1997).
Burnett, J.C. et al., Current progress of siRNA/shRNA therapeutics in clinical trials. Biotechnology Journal 6(9): 1130-1146 (2011).
Byk, G. et al., Synthesis, activity, and structure—activity relationship studies of novel cationic lipids for DNA transfer. Journal of Medical Chemistry 41(2):224-235 (1998).

(56) References Cited

OTHER PUBLICATIONS

Caplen, N.J. et al., In vitro liposome-mediated DNA transfection of epithelial cell lines using the cationic liposome DC-Chol/DOPE, Gene Therapy, 2:603-613 (1995).
Cassiman, D. Gene transfer for inborn errors of metabolism of the liver: the clinical perspective, Current Pharmaceutical Design, 17(24):2550-2557 (2011).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chandler, R. et al., Liver-directed adeno-associated virus serotype 8 gene transfer rescues a lethal murine model of citrullinemmia type 1, Gene Therapy, 20:1188-1191 (2013).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Chiou, H.C. et al., Enhanced resistance to nuclease degradation of nucleic acids complexed to; asialoglycoprotein-polylysine carriers, Nucleic Acids Research, 22(24):5439-5446 (1994).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Conese, M. et al., Gene and Cell Therapy for Cystic Fibrosis: From Bench to Bedside, J. Cyst. Fibros., 10 Suppl 2:S114-s128 (2011).
Cotten, M. et al., Receptor-mediated transport of DNA into eukaryotic cells. Methods in Enzymology 217 (H):618-644 (1993).
Cowling, V.H., Regulation of mRNA cap methylation, Biochemical Journal, 425:295-302 (2010).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysics Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Dande, P. et al., Improving RNA interference in mammalian cells by 4'-thio-modified small interfering RNA (siRNA): effect on siRNA activity and nuclease stability when used in combination with 2'-0-alkyl modifications, Journal of Medicinal Chemistry, 49(5):1624-1634 (2006).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Debus, H. et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148:334-343 (2010).
Decher, G. Fuzzy Nanoassemblies: Toward Layered Polymeric Multicomposites. Science 277: 1232-1237 (1997).
Demeshkina, N. et al., Interactions of the ribosome with mRNA and tRNA, Current Opinion in Structural Biology, 20(3):325-332 (2010).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N'',N'''-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Drummond, D.C. et al., Optimizing Liposomes for Delivery of Chemotherapeutic Agents to Solid Tumors, Pharmacological Reviews, 51(4): 691-743 (1999).
Dwarki, V. et al., Cationic liposome-mediated RNA transfection, Methods in Enzymology, 217:644-654 (1993).
Elbashir, S.M. et al., RNA interference is mediated by 21- and 22-nucleotide RNAs. Genes & Development 15: 188-200 (2001).
Elton, C., The Next Next Big Thing, Boston Magazine, 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst, N. et al., Interaction of Liposomal and Polycationic Transfection Complexes with Pulmonary Surfactant, J. Gene. Med., 1:331-340 (1999).
Estimated Number of Animal and Plant Species on Earth, http://www.factmonster.com/ipka/A0934288.html, 2000-2014, 3 pages, (Retrieved Aug. 2, 2014).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fath, S. et al., Multiparameter RNA and Codon Optimization: A Standardized Tool to Assess and Enhance Autologous Mammalian Gene Expression, PLoS One, 6(3):e17596 (14 pages) 2011.
Fechter, P. and Brownlee, G. G., Recognition of mRNA cap structures by viral and cellular proteins, Journal of General Virology, 86:1239-1249 (2005).
Felgner, P.L. and Ringold, G.M., Cationic liposome-mediated transfection, Nature, 337(6205):387-388 (1989).
Felgner, P.L. et al., Lipofection: A Highly Efficient, Lipid-Mediated DNA-Transfection Procedure, Proc. Natl. Acad., 84:7413-7417 (1987).
Fenske, D.B. and Cullis, P., Liposomal nanomedicines. Expert Opinion on Drug Delivery 5(1):25-44 (2008).
Fernandez, V. et al., Cross Flow Filtration of RNA Extracts by Hollow Fiber Membrane, Acta Biotechnologica, 12(1):49-56 (1992).
Ferruti, P.F. and Barbucci, R., Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391 (6669):806-811 (1998).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-992 (2004).
Fumoto, S. et al., Targeted Gene Delivery: Importance of Administration Routes, Novel Gene Therapy Approaches, 3-31 (2013).
Furgeson, D.Y. et al., Modified linear polyethylenimine-cholesterol conjugates for DNA complexation. Bioconjugate Chemistry 14(4):840-847 (2003).

(56) References Cited

OTHER PUBLICATIONS

Furgeson, D.Y. et al., Novel water insoluble lipoparticulates for gene delivery. Pharmaceutical Research 19(4): 382-390 (2002).
Galipon, J. et al., Stress-induced lncRNAs evade nuclear degradation and enter the translational machinery, Genes to Cells, 18(5):353-368 (2013).
Gao, X. and Huang, L., A novel cationic liposome reagent for efficient transfection of mammalian cells, Biochem. Biophys. Res. Comm., 179(1): 280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Geraerts, M. et al., Upscaling of lentiviral vector production by tangential flow filtration, Journal of Gene Medicine, 7(10):1299-1310 (2005).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M. et al., Polyion complex micelles as vectors in gene therapy—pharmacokinetics and in vivo; gene transfer, Gene Therapy, 9(6):407-414 (2002).
Haskins M., Gene Therapy for Lysosomal Storage Disorders (LDSs) in Large Animal Models, Ilar J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(2S):346S (1994).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Henkin, R. I. et al., Inhaled Insulin—Intrapulmonary, intranasal, and other routes of administration: Mechanisms of action, Nutrition, 26: 33-39 (2010).
Hess, P. R. et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy:CII, 55(6): 672-683 (2006).

Heyes, J. et al., Cationic Lipid Saturation Influences Intracellular Delivery of Encapsulated Nucleic Acids, J. Controlled Release, 107:276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hillery, A.M. et al., Drug Delivery and Targeting for Pharmacists and Pharmaceutical Scientists, Taylor and Francis (2005).
Hoerr, I. et al., In Vivo Application of RNA Leads to Induction of Specific Cytotoxic T Lymphocytes and Antibodies, European Journal of Immunology, 30(1):1-7 (2000).
Hofland, H.E.J et al., Formation of stable cationic lipid/DNA complexes for gene transfer. Proceedings of the National Academy of Sciences of the USA 93 (14): 7305-7309 (1996).
*Homo sapiens* galactosidase, alpha (GLA) mRNA, NCBI Reference Sequence NM_000169.1, Modification Date: Nov. 17, 2006.
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Techniques, In: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-Based Lipids for Ordered Assembly of Bioresponsive Gene Carriers, Molecular Therapy, 11(3):409-417 (2005).
Huttenhofer, A. and Noller, H., Footprinting mRNA-ribosome complexes with chemical probes, The EMBO Journal, 13(16):3892-3901 (1994).
Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (dated Jun. 14, 2012).
International Search Report for PCT/US2010/058457, 4 pages (dated May 6, 2011).
International Search Report for PCT/US2011/062459, 3 pages (dated Apr. 11, 2012).
International Search Report for PCT/US2012/041663, 4 pages (dated Oct. 8, 2012).
International Search Report for PCT/US2012/041724, 5 pages (dated Oct. 25, 2012).
International Search Report for PCT/US2013/034602, 2 pages (dated Jun. 17, 2013).
International Search Report for PCT/US2013/034604, 4 pages (dated Jun. 17, 2013).
International Search Report for PCT/US2013/044769, 4 pages (dated Nov. 12, 2013).
International Search Report for PCT/US2013/044771, 6 pages (dated Nov. 1, 2013).
International Search Report for PCT/US2013/073672, 6 pages (dated Mar. 3, 2014).
International Search Report for PCT/US2014/027422, 5 pages (dated Jul. 31, 2014).

(56) References Cited

OTHER PUBLICATIONS

International Search Report for PCT/US2014/027585, 3 pages (dated Jul. 14, 2014).
International Search Report for PCT/US2014/027602, 6 pages (dated Jul. 28, 2014).
International Search Report for PCT/US2014/027717, 5 pages (dated Jul. 16, 2014).
International Search Report for PCT/US2014/028330, 5 pages (dated Jul. 22, 2014).
International Search Report for PCT/US2014/028441, 6 pages (dated Jul. 22, 2014).
International Search Report for PCT/US2014/028498, 5 pages (dated Jul. 28, 2014).
International Search Report for PCT/US2014/061786, 6 pages (dated Feb. 6, 2015).
International Search Report for PCT/US2014/061793, 4 pages (dated Feb. 6, 2015).
International Search Report for PCT/US2014/061830, 5 pages (dated Feb. 4, 2015).
International Search Report for PCT/US2014/061841, 6 pages (dated Feb. 24, 2015).
International Search Report for PCT/US2015/21403 (4 pages) dated Jun. 15, 2015.
Jakobsen, K. et al., Purification of MRNA Directly From Crude Plant Tissues in 15 Minutes Using Magnetic Oligo DT Microspheres, Nucleic Acids Research, 18(12):3669 (1990).
Jeffs, L.B. et al., A scalable, extrusion-free method for efficient liposomal encapsulation of plasmid DNA, Pharmacol. Res., 22(3): 362-372 (2005).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic & Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., In vivo protein expression from mRNA delivered into adult rat brain, Journal of Neuroscience Methods, 105:77-86 (2001).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kasuya, T. et al., In Vivo Delivery of Bionanocapsules Displaying *Phaseolus vulgaris* Agglutinin-$L_4$ Isolectin to Malignant Tumors Overexpressing N-Acetylglucosaminyltransferase V, Human Gene Therapy, 19:887-895 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer THerapy, Current Gene Therapy, 9: 434-458 (2009).

Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A.L. et al., Amphipathic polyethyleneglycols effectively prolong the circulation time of liposomes, FEBS, 268(1): 235-237 (1990).
Kober, L. et al., Optimized Signal Peptides for the Development of High Expressing CHO Cell Lines, Biotechnol. Bioeng., 110:1164-1173 (2012).
Kodama, K. et al., The Features and Shortcomings for Gene Delivery of Current Non-Viral Carriers, Current Medicinal Chemistry, 13: 2155-2161 (2006).
Kormann, M.S.D. et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).
Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011).
Lasic, D.D. et al., Gelation of liposome interior. A novel method for drug encapsulation, FEBS Letters, 312(2-3):255-258 (1992).
Lasic, D.D. Novel applications of liposomes, Trends in Biotechnology, 16:307-321 (1998).
Lee, S. et al., Stability and cellular uptake of polymerized siRNA (poly-siRNA)/polyethylenimine (PEI) complexes for efficient gene silencing. Journal of Controlled Release 141: 339-346 (2010).
Li, L. et al., Preparation and Gene Delivery of Alkaline Amino Acids-Based Cationic Liposomes, Archives of Pharmaceutical Research, 31(7):924-931 (2008).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lim, Y. et al., A self-destroying polycationic polymer: biodegradable poly(4-hydroxy-l-proline ester). Journal of American Chemical Society 121: 5633-5639 (1999).
Lindgren, V. et al., Human Ornithine Transcarbamylase Locus Mapped to Band Xp21.1 Near the Duchenne Muscular Dystrophy Locus, Science, 226(2675):698-700 (1984).
Liu, X. et al., COStar: a D-star Lite-based Dynamic Search Algorithm for Codon Optimization, Journal of Theoretical Biology, 344:19-30 (2014).
Liu, Y. and Huang, L., Designer Lipids Advance Systematic siRNA Delivery, Molecular Therapy, 18(4):669-670 (2010).
Liu, Y. et al., Factors influencing the efficiency of cationic liposome-mediated intravenous gene delivery, Nature Biotechnology, 15:167-173 (1997).
Lo, K-M et al., High level expression and secretion of Fc-X fusion proteins in mammalian cells, Protein Engineering, 11(6):495-500 (1998).
Lorenzi, J. C. C. et al., Intranasal Vaccination with Messenger RNA as a New Approach in Gene Therapy: Use Against Tuberculosis, BMC Biotechnology, 10(77):1-11 (2010).

(56) References Cited

OTHER PUBLICATIONS

Love, K.T. et al., Lipid-like materials for low-dose, in vivo gene silencing, PNAS, 107(5):1864-1869 (2010).
Lu, D. et al., Optimization of methods to achieve mRNA-mediated transfection of tumor cells in vitro and in vivo employing cationic liposome vectors, Cancer Gene Therapy, 1(4):245-252 (1994).
Lukyanov, A.N. and Torchilin, V.P., Micelles from lipid derivatives of water-soluble polymers as delivery systems for poorly soluble drugs. Advanced Drug Delivery Reviews 56: 1273-1289 (2004).
Luo, D. and Saltzman, M., Synthetic DNA delivery systems. Nature Biotechnology 18: 33-37. Review (2000).
Lynn, D.M. and Langer, R., Degradable Poly(β-amino esters):? Synthesis, Characterization, and Self-Assembly with Plasmid DNA. Journal of American Chemical Society 122(44): 10761-10768 (2000).
Lynn, D.M. et al., Accelerated discovery of synthetic transfection vectors: parallel synthesis and screening of a degradable polymer library. Journal of American Chemical Society 123 (33): 8155-8156 (2001).
Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Developlment of Cationic Polymer Coatings to Regulate Foreign Body Responses. Advanced Healthcare Materials 23: H189-H194. Reviews (2011).
MacLachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.
Maeda-Mamiya, R. et al., In vivo gene delivery by cationic tetraamino; fullerene. Proceedings of National Academy of Sciences U S A, 107(12):5339-5344 (2010).
Malone, R.W., et al., Cationic liposome-mediated RNA transfection, PNAS, 86:6077-6081 (1989).
Mammal, http://en.wikipedia.org/wiki/Mammal, 2007, Pearson Education, NY, NY, Author unkown (Source: The international union for conservation of nature and natural resources), 2 pages, (Retrieved Aug. 2, 2014).
Mansour, H.M. et al., Nanomedicine in pulmonary delivery, International Journal of Nanomedicine, 4:299-319 (2009).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N,N'-Disubstituted-ethylenediaminedipropionic Acids. Journal of the American Chemical Society 72: 5357-5361 (1950).
Martinon, F. et al., Induction of Virus-Specific Cytotoxic T Lymphocytes in Vivo by Liposome-Entrapped mRNA, European Journal of Immunology, 23(7):1719-1722 (1993).
Mathiowitz, E. and Langer, R., Polyanhydride microspheres as drug carriers I. Hot-melt microencapsulation. Journal of Controlled Release 5: 13-22 (1987).
Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
McCracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
McIvor, R. S., Therapeutic Delivery of mRNA: The Medium is the Message, Molecular Therapy, 19(5):822-823 (2011).
Melton, D.A. et al., Efficient in vitro synthesis of biologically active RNA and RNA hybridization probes from; plasmids containing a bacteriophage SP6 promoter, Nucleic Acids Research, 12(18):7035-7056 (1984).

Mendelsohn, J.D. et al., Rational design of cytophilic and cytophobic polyelectrolyte multilayer thin films. Biomacromolecules 4(1): 96-106 (2003).
Merkel, O.M. and Kissel, T., Nonviral Pulmonary Delivery of siRNA, Accounts of Chemical Research, 45(7):961-970 (2012).
Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37: 1768-1785 (1998).
Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).
Morrissey, D.V. et al., Potent and Persistent in vivo Anti-HBV Activity of Chemically Modified siRNAs, Nat. Biotechnol., 23(8): 1003-1007 (2005).
Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid-polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al., The Interaction between Cap-binding Complex and RNA Export Factor is Required for Intronless mRNA Export, Journal of Biological Chemistry, 282(21):15645-15651 (2007).
Nori, A. et al., Tat-conjugated synthetic macromolecules facilitate cytoplasmic drug delivery to human ovarian carcinoma cells, Bioconj. Chem., 14(1): 44-50 (2003).
Okumura, K. et al., Bax mRNA therapy using cationic liposomes for human malignant melanoma, The Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications for drug delivery: nasal and pulmonary routes, Nanomaterials and Nanosystems for Biomedical Applications, M.R. Mozafari (ed.): 99-112 (2007).
Painter, H. et al, Topical Delivery of mRNA to the Murine Lung and Nasal Epithelium, Gene Medicine Group and the Medical Informatics Unit, Nuffield Department of Clinical Laboratory Sciences, University of Oxford, 1 page.
Painter, H. et al., Topical Delivery of mRNA to the Murine Lung and Nasal Epithelium, Molecular Therapy, 9:S187 (2004).
Painter, H., An Investigation of mRNA as a Gene Transfer Agent, Gene Medicine Research Group Nuffield Department of Clinical Laboratory Sciences and Merton College, University of Oxford, 1-282 (2007).
Painter, H., An Investigation of mRNA as a Gene Transfer Agent, Oxford University GeneMedicine, Abstract Only, 1 page (2007).
Parrish, D.A. and Mathias, L.J., Five- and six-membered ring opening of pyroglutamic diketopiperazine. Journal of Organic Chemistry 67(6): 1820-1826 (2002).
Patton, J., Market Trends in Pulmonary Therapies, Trends and Opportunities, VI: 372-377.
Paulus, C. and Nevels, M., The Human Cytomegalovirus Major Immediate-Early Proteins as Antagonists of Intrinsic and Innate Antiviral Host Responses, Viruses, 1:760-779 (2009).
Peppas, N.A. et al., Hydrogels in Biology and Medicine: From Molecular Principles to Bionanotechnology. Advanced Materials 18: 1345-1360 (2006).

(56) References Cited

OTHER PUBLICATIONS

Philipp, A. et al., Hydrophobically modified oligoethylenimines as highly efficient transfection agents for siRNA delivery. Bioconjugate Chemistry 20(11): 2055-2061 (2009).
Pons, M. et al., Liposomes obtained by the ethanol injection method, Int. J. Pharm., 95: 51-56. (1993).
Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATtract mRNA Isolation Systems, Instructions for Use of Products Z5200, Z5210, Z2300 and Z5310, Technical Manual (2012).
Putnam, D. Polymers for gene delivery across length scales. Nature Materials 5: 439-451 (2006).
Putnam, D. and Langer, R., Poly(4-hydroxy-l-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Reddy, A. et al., The Effect of Labour and Placental Separation on the Shedding of Syncytiotrophoblast Microparticles, Cell-free DNA and mRNA in Normal Pregnancy and Pre-eclampsia, Placenta, 29: 942-949 (2008).
Rejman, J. et al., Characterization and transfection properties of lipoplexes stabilized with novel exchangeable polyethylene glycol-lipid conjugates, Biochimica et Biophysica Acta, 1660:41-52 (2004).
Remington: The Science and Practice of Pharmacy, 21st Edition, Philadelphia, PA. Lippincott Williams & Wilkins (2005).
Rosenecker, J. et al., Gene Therapy for Cystic Fibrosis Lung Disease: Current Status and Future Perspectives, Curr. Opin. Mol. Ther., 8:439-445 (2006).
Rosenecker, J. et al., Interaction of Bronchoalveolar Lavage Fluid with Polyplexes and Lipoplexes: Analysing the Role of Proteins and Glycoproteins, J. Gene. Med., 5:49-60 (2003).
Rowe, S.M. et al., Cystic Fibrosis, New Engl. J. Med. 352:1992-2001 (2005).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Schreier, H., The new frontier: gene and oligonucleotide therapy, Pharmaceutica Acta Helvetiae, 68(3):145-159 (1994).
Semple, S.C. et al., Rational design of cationic lipids for siRNA delivery, Nature Biotechnology, 28(2): 172-176 (2010).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway of the Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-13001 (2011).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50)47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated Via Electrostatic Surface Binding of mRNA To Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Suri, M. et al., Genetics for Pediatricians, Remedica Publishing, (2005).
Szoka, F. and Papahadjpoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334 (1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).
Third Party Preissuance Submission Under 37 CFR § 1.290 (Oct. 25, 2013).
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsui, N.B. et al., Stability of endogenous and added RNA in blood specimens, serum, and plasma, Clinical Chemistry, 48(10):1647-1653 (2002).
Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-3197 (1999).
Urban-Klein, B. et al., RNAi-mediated gene-targeting through systemic application of polyethylenimine (PEI)-complexed siRNA in vivo. Gene Therapy 12(5): 461-466 (2005).

(56) References Cited

OTHER PUBLICATIONS

Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Van Der Gun, B.T.F et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Varambally, S. et al., Genomic Loss of microRNA-101 Leads to Overexpression of Histone Methyltransferase EZH2 in Cancer, Science, 322:1695-1699 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al., Gene therapy for liver diseases using non-viral minicircle-DNA vector, Human Gene Therapy, 23(10):A145 (2012).
Viecelli, H. et al., Gene therapy for liver diseases using non-viral minicircle-DNA vector, Molecular Therapy, 21(1):S136 (2013).
Vomelova, I. et al., Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).
Wang, Y. et al., Systemic delivery of modified mRNA encoding herpes simplex virus 1 thymidine kinase for targeted cancer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Written Opinion for PCT/US2010/058457, 14 pages (dated May 6, 2011).
Written Opinion for PCT/US2011/062459, 9 pages (dated Apr. 11, 2012).
Written Opinion for PCT/US2012/041663, 7 pages (dated Oct. 8, 2012).
Written Opinion for PCT/US2012/041724, 11 pages (dated Oct. 25, 2012).
Written Opinion for PCT/US2013/034602, 4 pages (dated Jun. 17, 2013).
Written Opinion for PCT/US2013/034604, 9 pages (dated Jun. 17, 2013).
Written Opinion for PCT/US2013/044769, 8 pages (dated Nov. 12, 2013).
Written Opinion for PCT/US2013/044771, 7 pages (dated Nov. 1, 2013).
Written Opinion for PCT/US2013/073672, 7 pages (dated Mar. 3, 2014).
Written Opinion for PCT/US2014/027422, 6 pages (dated Jul. 31, 2014).
Written Opinion for PCT/US2014/027602, 7 pages (dated Jul. 28, 2014).
Written Opinion for PCT/US2014/027717, 5 pages (dated Jul. 16, 2014).
Written Opinion for PCT/US2014/028330, 7 pages (dated Jul. 22, 2014).
Written Opinion for PCT/US2014/028441, 6 pages (dated Jul. 22, 2014).
Written Opinion for PCT/US2014/028498, 6 pages (dated Jul. 28, 2014).
Written Opinion for PCT/US2014/061786, 5 pages (dated Feb. 6, 2015).
Written Opinion for PCT/US2014/061793, 4 pages (dated Feb. 6, 2015).
Written Opinion for PCT/US2014/061830, 7 pages (dated Feb. 4, 2015).
Written Opinion for PCT/US2014/061841, 8 pages (dated Feb. 24, 2015).
Written Opinion for PCT/US2015/21403 (7 pages) dated Jun. 15, 2015.
Wu, J. and Zern, M., Modification of liposomes for liver targeting, Journal of Hepatology, 24(6)757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Yamamoto, A. et al., Current prospects for mRNA gene delivery, European Journal of Pharmaceutics and Biopharmaceutics, 71(3): 484-489 (2009).
Yamamoto, Y. et al., Important Role of the Proline Residue in the Signal Sequence that Directs the Secretion of Human Lysozyme in *Saccharomyces cerevisiae*, Biochemistry, 28:2728-2732 (1989).
Yasuda, M. et al., Fabry Disease: Novel [alpha]-Galactosidase A 3-terminal Mutations Result in Multiple Transcripts Due to Aberrant 3-End Formation, American Journal of Human Genetics, 73:162-173 (2003).
Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).
Yokoe, H. et al., Spatial dynamics of GFP-tagged proteins investigated by local fluorescence enhancement, Nature Biotechnology, 14(10):1252-1256 (1996).
Yoneda et al., A cell-penetrating peptidic GRP78 ligand for tumor cell-specific prodrug therapy, Bioorg. Med. Chem. Lett., 18(5): 1632-1636 (2008).
Yoshioka, Y. and Calvert, P., Epoxy-based Electroactive Polymer Gels. Experimental Mechanics 42(4): 404-408 (2002).
Zagridullin, P.H. et al., Monobasic amines. II. Cycloalkylation and hydroxyalkylation of cyclic and acyclic di- and polyamines. Journal of Organic Chemistry26(1):184-88. Russian (1990).

(56) References Cited

OTHER PUBLICATIONS

Zaugg, H.E. et al., 3-Carboxy-2,5-piperazinedione and Derivatives. Journal of American Chemical Society 78(11):2626-2631 (1956).
Zauner, W.et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7):1448-1455 (2008).
Zou, S. et al., Lipid-mediated delivery of RNA is more efficient than delivery of DNA in non-dividing cells, International Journal of Pharmaceutics, 389(1-2):232-243 (2010).
Baboo et al., "Dark matter' worlds of unstable RNA and protein", Nucleus, 2014, 5:4 281-286.
Bhaduri, S. et al., "Procedure for the Preparation of Milligram Quantities of Adenovirus Mesenaer Ribonucleic Acid", Journal of Viroloay, 2(6):1126-1129, (1972).
Kariko et al., "Generating the optimal mRNA for therapy: HPLC purification eliminates immune activation and improves translation of nucleoside-modified, protein-encoding mRNA", Nucleic Acids Research, pp. 1-10 (2011).
Lee et al., "A Polynucleotide Segment Rich in Adenylie Acid in the Rapidly-Labeled Polyribosomal RNA Component of Mouse Sarcoma 180 Ascites Cells", PNAS 68(6): 13331-35 (Jun. 1971).
Lee et al., "Tiny abortive initiation transcripts exert antitermination activity on an RNA hairpin-dependent intrinsic terminator", Nucleic Acids Research, 38(18): 6045-53 (2010).
Wurm F.M., "Review: Production of recombinant protein therapeutics in cultivated mammalian cells", Nature Biotechnology, 22(11): 1393-8 (Nov. 2004).
Kern et al., "Application of a Fed-Batch System To Produce RNA by In Vitro Transcription", Biotechnol. Prog. 15 :174 (1999).
Chomczynski et al., "Single-step method of RNA isolation by acid guanidinium thiocyanate-phenol-chloroform extraction", Analytical Biochemistry 162(1): 156-9 (1987).
Cowan et al., Boichem. Cell Biol. 80 745 (2002).
Kahn et al., "Purification of Plasmid DNA by Tangential Flow Filtration", Biotech. Bioeng. 69: 101-106,(2000).
Kariko et al., Modern Therapy 16(11): 1833 (2008).
Keith et al., "Continuous culture system for production of biopolymer levan using erwinia herbicola", Biotech. Bioeng. 38: 557-560 (1991).
Krieg et al., Nucleic Acids Research 12 (18): 7057 (1984).
Kormann et al., Nature Biotechnology 29 (2): 154 (2011).
Martin et al., "Tailing and 3' -end labeling of RNA with yeast poly(A) polymerase and various nucelotides", RNA, 4:226-230, (1998).
Novagen, "Bug Buster Protein Extraction Protocol/Reagent". downloaded from the internet on Aug. 3, 2017.
Schwartz, "Tangential Flow Filtration", downloaded from the internet on Aug. 3, 2017.
Pokroskaya et al., Analytical Biochemistry 220: 420 (1994).
Rosemeyer et al., Analytical Biochemistry 224: 446 (1995).
You et al., Cell Biology International Reports 16(7): 663 (1992).
Ross et al. PNAS 69 (1): 264 (1972).
Nakanishi et al., "New Transfection Agents Based on Liposomes Containing Biosurfactant MEL-A", Pharmaceuticals, 5(3):411-420 (2013).
Robinson et al., "Lipid Nanoparticle-Delivered Chemically Modified mRNA Restores Chloride Secretion in Cystic Fibrosis", Molecular Therapy 26(8): 1-13 (2018).
Alton et al., "A randomized, double-blind, placebo-controlled trial of repeated nebulization of non-viral cystic fibrosis transmembrane conductance regulator (CFTR) gene therapy in patients with cystic fibrosis", Efficacy and Mechanism Evaluation), 3(28), (2016).
International Search Report for PCT/US2019/048154 (5 pages) dated Nov. 22, 2019.
Written Opinion for PCT/US2019/048154, (7 pages) dated Nov. 22, 2019.
Sahin et al., "mRNA-based therapeutics—developing a new class of drugs", Nature Reviews Drug Discovery, vol. 13, No. 10, pp. 759-780 (2014).
Merdy "Selection of clarification methods for improved downstream performance and economics", vol. 14, issue 3, pp. 50-55 (2015).

\* cited by examiner

Lane 1: Positive Control showing residual enzyme (highest band)
Lane 2: Negative Control showing no residual enzyme
Lanes 3 and 4: Purified MUT mRNA loaded at 1 mg/mL concentration
Lanes 5 and 6: Purified MUT mRNA loaded at 2 mg/mL concentration
Lane 7: RNA Polymerase enzyme
Lane 8: O-Methyl Transferase enzyme
Lane 9 Guanylyl Transferase enzyme
Lane 10 RNase I

METHODS FOR PURIFICATION OF MESSENGER RNA

CROSS-REFERENCE TO RELATED APPLICATION

This application claims the benefit of, and priority to, U.S. Ser. No. 62/722,674, filed on Aug. 24, 2018, the content of which is incorporated herein in its entirety.

BACKGROUND

Messenger RNA (mRNA) therapeutics are promising new therapeutics; for example, mRNA therapeutics can be alternatives to traditional protein replacement therapies, antibody therapies, vaccine therapies and/or gene therapies. In an mRNA therapeutic, an intact mRNA encoding a specific enzyme, antibody, antigen or other protein or peptide is delivered to a target cell and is translated by the cell's own native translational machinery into the intact enzyme, antibody, antigen or other protein or peptide. mRNA for such therapeutics typically are synthesized using in vitro transcription systems with enzymes such as RNA polymerases transcribing mRNA from template plasmid DNA, along with or followed by addition of a 5'-cap and 3'-polyadenylation. Such reaction(s) result in a composition that includes both full-length mRNA and various undesirable contaminants, e.g., proteins, salts, buffers, and non-RNA nucleic acids used in the reaction(s) that have to be removed to provide a clean and homogeneous mRNA that is usable in an mRNA replacement therapeutic.

Traditionally, small scale mRNA is purified from in vitro transcription reactions by either commercially-available silica-based column systems, such as the Qiagen RNeasy® kit, or by protein extraction into an organic mix (phenol:chloroform:isoamyl alcohol) and subsequent ethanol precipitation. These methods are limited in scale as they can provide maximally 5 to 10 mg of clean and homogeneous mRNA; thus, they are inadequate for the needs of clinical and commercial therapeutic uses of mRNA.

SUMMARY OF THE INVENTION

The present invention provides an improved large-scale purification method for in vitro synthesized mRNA based in part on the surprising finding that in vitro synthesized mRNA can be efficiently purified to a purity appropriate for clinical or commercial therapeutic uses, using normal flow filtration. Significantly, normal flow filtration methods described herein result in unexpectedly high yield of mRNA with high purity and integrity. Thus, the present invention permits more efficient and cost-effective manufacturing of high-quality mRNA for therapeutic use.

As used herein, the term "normal flow filtration" refers to a filtration process in which the material to be purified flows in a direction normal (i.e., perpendicular) to the surface of the filter. Materials that are too large to pass through the filter are retained whereas smaller materials pass through to the filtrate.

In one aspect, the invention provides a method for purifying messenger RNA (mRNA) that comprises the steps of: (a) precipitating mRNA in a composition comprising one or more contaminants from manufacturing the mRNA, to provide a suspension comprising precipitated mRNA; (b) subjecting the suspension comprising the precipitated mRNA to a filter wherein the precipitated mRNA is retained by the filter, (c) washing the precipitated mRNA by washing the filter from step (b) comprising the retained, precipitated mRNA; (d) dissolving the precipitated mRNA retained by the filter in step (c) thereby allowing purified mRNA to pass through the filter, and (e) recovering the purified mRNA from step (d), wherein each of steps (b), (c) and (d) is conducted using normal flow filtration.

In some embodiments, the manufacturing the mRNA comprises in vitro transcription (IVT) synthesis. In some embodiments, the manufacturing the mRNA comprises a step of 5'-capping of the mRNA after synthesis. In some embodiments, the manufacturing the mRNA does not comprise a step of 5'-capping of the mRNA. In some embodiments, the method further comprises a step of capping the purified mRNA with a 5'cap, following step (e).

In some embodiments, the manufacturing the mRNA comprises a step of 3'-tailing of the mRNA. In some embodiments, the manufacturing the mRNA does not comprise a step of 3'-tailing of the mRNA. In some embodiments, the method further comprises a step of 3' tailing of the purified mRNA, following step (e).

In some embodiments, the manufacturing the mRNA does not comprise a step of 5'-capping of the mRNA and does not comprise a step of 3'-tailing of the mRNA. In some embodiments, the method further comprises steps of capping the purified mRNA with a 5'cap and 3' tailing of the purified mRNA, following step (e).

In some embodiments, the one or more contaminants comprise an enzyme. In some embodiments, the enzyme is a polymerase used in IVT synthesis of mRNA. In some embodiments, the enzyme is a capping enzyme. In some embodiments, the enzyme is a poly A polymerase. In some embodiments, the one or more contaminants comprise a salt. In some embodiments, the one or more contaminants comprise short abortive transcripts.

In some embodiments, a filter suitable for normal flow filtration has a pore size (e.g., pore diameter) or a molecular weight cut off (MWCO) that is substantially smaller than the precipitated mRNA and larger than the soluble mRNA or contaminants so that the precipitated mRNA can be retained on the filter while the soluble contaminants flow through.

In some embodiments, a filter suitable for the invention is a membrane filter. In some embodiments, the membrane filter has a molecular weight cut off (MWCO) that is substantially smaller than the precipitated mRNA and larger than soluble mRNA or contaminants.

In some embodiments, a membrane filter has a format of pleated filter, a wrapped filter, or a capsule filter. In some embodiments, a filter comprises a filter screen.

In some embodiments, a filter suitable for the invention is a depth filter. In some embodiments, the depth filter has a pore size or pore diameter that is substantially smaller than the precipitated mRNA and larger than the soluble mRNA or contaminants.

In some embodiments, a filter is made of an inert material. In some embodiments, an inert material suitable for the invention is polypropylene. In some embodiments, an inert material is modified polyether sulfone (mPES). In some embodiments, an inert material is polyether sulfone (PES). In some embodiments, an inert material is polyvinylidene fluoride (PVDF). In some embodiments, an inert material is cellulose. In some embodiments, an inert material is diatomaceous earth. In some embodiments, the inert material is polytetrafluoroethylene (PTFE). In some embodiments, the inert material is nitrocellulose. In some embodiments, the inert material is polyethylene. In some embodiments, the inert material is polyacrylonitrile. In some embodiments, the inert material is polycarbonate. In some embodiments, the inert material is nylon.

In some embodiments, a filter comprises one or more three-dimensional matrices. In some embodiments, the one or more three-dimensional matrices is a felt matrix. In some embodiments, the thickness of the felt is about 1 millimeter (mm) to about 1 centimeter (cm) (e.g., about 1-500 mm, about 1-400 mm, about 1-300 mm, about 1-200 mm, about 1-100 mm, about 1-50 mm, about 1-40 mm, about 1-30 mm, about 1-20 mm, about 1-10 mm, or about 1-5 mm). In some embodiments, the thickness of the felt is between 1-10 mm. In some embodiments, the thickness of the felt is between 1-5 mm. In some embodiments, the thickness of the felt is less than 1 centimeter, less than 0.5 cm, less than 0.4 cm, less than 0.3 cm, less than 0.25 cm, less than 0.2 cm, less than 0.1 cm, less than 50 mm, less than 40 mm, less than 30 mm, less than 25 mm, less than 20 mm, less than 15 mm, less than 10 mm or less than 5 mm. In some embodiments, a filter comprises at least two, three, four, five, six, seven, eight, nine or ten three-dimensional matrices. In some embodiments, a filter comprises stacked three-dimensional matrices.

In some embodiments, a filter has an average pore size that facilitates retaining of precipitated mRNA. In some embodiments, a filter has an average pore size of between 0.001 µm and 500 µm, between 0.01 µm and 200 µm, or between 0.05 µm and 100 µm. In some embodiments, a filter has an average pore size of 0.05 µm or greater. In some embodiments, a filter has an average pore size of 0.5 µm or greater. In some embodiments, a filter has an average pore size of 5 µm or greater. In some embodiments, a filter has an average pore size of 10 µm or greater. In some embodiments, a filter has an average pore size of 20 µm or greater. In some embodiments, a filter has an average pore size of 25 µm or greater.

In some embodiments, a filter has a total surface area that facilitates capturing and/or distribution of the precipitated mRNA. In particular embodiments, a filter has a total surface area that provides for no gel layer for the amount of mRNA distributed onto the filter.

In some embodiments, a method according to the present invention requires no dispersant added to the suspension containing the precipitated mRNA.

In some embodiments, the step of precipitating mRNA comprises use of an organic solvent to precipitate the mRNA. In some embodiments, the step of precipitating the mRNA comprises use of ethanol to precipitate the mRNA.

In some embodiments, the step of precipitating mRNA does not comprise an organic solvent. In some embodiments, the step of precipitating mRNA does not comprise an organic solvent and the mRNA is precipitated using polyethylene glycol (PEG). In some embodiments, the step of precipitating mRNA comprises using PEG to precipitate the mRNA.

In some embodiments, the step of precipitating mRNA does not comprise an organic solvent and comprises triethylene glycol (TEG) to precipitate the mRNA. In some embodiments, the step of precipitating mRNA comprises use of TEG to precipitate the mRNA.

In some embodiments, the step of precipitating mRNA does not comprise an organic solvent and comprises triethylene glycol monomethyl ether (MTEG) to precipitate the mRNA. In some embodiments, the step of precipitating mRNA comprises use of MTEG to precipitate the mRNA.

In some embodiments, the step of washing the precipitated mRNA comprises washing the precipitated mRNA with one or more salt washes. In some embodiments, the step of washing the precipitated mRNA comprises one or more washes with an organic solvent. In some embodiments, the step of washing the precipitated mRNA comprises one or more of ethanol wash.

In some embodiments, the step of washing the precipitated mRNA does not comprise an organic solvent. In some embodiments, the step of washing the precipitated mRNA does not comprise an organic solvent and comprises polyethylene glycol (PEG). In some embodiments, the step of washing the precipitated mRNA comprises one or more washes comprising PEG. In some embodiments, the PEG used to wash the precipitated mRNA has a viscosity of 90 centistrokes or less. In some embodiments, the PEG used to wash the precipitated mRNA has a viscosity of 80 centistrokes or less. In some embodiments, the PEG used to wash the precipitated mRNA has a viscosity of 70 centistrokes or less. In some embodiments, the PEG used to wash the precipitated mRNA has a viscosity of 60 centistrokes or less. In some embodiments, the PEG used to wash the precipitated mRNA has a viscosity of 50 centistrokes or less. In some embodiments, the PEG used to wash the precipitated mRNA has a viscosity of 40 centistrokes or less. In some embodiments, the PEG used to wash the precipitated mRNA has a viscosity of 30 centistrokes or less. In some embodiments, the PEG used to wash the precipitated mRNA has a viscosity of 20 centistrokes or less. In some embodiments, the PEG used to wash the precipitated mRNA has a viscosity of 10 centistrokes or less.

In some embodiments, the step of washing the precipitated mRNA does not comprise an organic solvent and comprises triethylene glycol (TEG). In some embodiments, the step of washing the precipitated mRNA comprises one or more washes comprising TEG.

In some embodiments, the step of washing the precipitated mRNA does not comprise an organic solvent and comprises triethylene glycol monomethyl ether (MTEG). In some embodiments, the step of washing the precipitated mRNA comprises one or more washes comprising MTEG.

In some embodiments, the normal flow filtration comprises one or more of: constant flow; constant pressure; variable flow; variable pressure; flow by wicking and gravity control.

In some embodiments, the normal flow filtration comprises a system and/or filter that are for single use. In some embodiments, the normal flow filtration comprises a system and/or filter that are for multi-use.

In some embodiments, the recovery step comprises one or more of:

recirculation of water/buffer;
single pass flush of water/buffer; and
reverse flush of water/buffer.

A method according to the present invention may be used to purify any mRNA that encodes a protein or a peptide. In some embodiments, the protein is a metabolic protein or peptide. In some embodiments, the protein or peptide is an enzyme. In some embodiments, the protein or peptide is a receptor protein. In some embodiments, the protein or peptide is a secreted protein or peptide. In some embodiments, the protein or peptide is a non-secreted protein or peptide. In some embodiments, the protein or peptide is a cytosolic protein or peptide. In some embodiments, the protein or peptide is a nuclear protein or peptide. In some embodiments, the protein or peptide is a mitochondrial protein or peptide. In some embodiments, the protein or peptide is a lysosomal protein or peptide. In some embodiments, the protein or peptide is an endoplasmic reticulum protein or peptide. In some embodiments, the protein or peptide is a Golgi protein or peptide. In some embodiments, the protein or peptide is a structural membrane protein or peptide.

In some embodiments, the protein is an antibody or antibody fragment. In some embodiments, the protein is an antigen. In some embodiments, the protein is a cancer associated antigen. In some embodiments, the protein is a vaccine. In some embodiments, the protein is selected from ABC7, ABCB3, ABCB7, ABCC7, ABCD1, AKT; AKT2, AKT3, ATF4, AKT2; AKT3; ALAS2, Alpha galactosidase, Alpha-1 Protease inhibitor, APA, APC; APOA1, APOE, Anti-trypsin alpha 1, Arginosuccinate synthase, ASAT; ATM; ATP7B, ATR; Atrophin-1; ATX3; Atxn10; ATXN2; Atxn7; ATXNl; Bax; Bcl2; Bcl2; BRCA1; BRCA2; Carbamylphosphate Synthase, CASP8, CBP (Creb-BP); CDKN2a; CFTR, CREB1, CVAP, CYP1Bl, DBA, DMD, DMPK; EGFR, EIF2B1, EIF2BA, EIF2B2, EIF2B3, EIF2B5, EIF2B4; ERBB2; ERBB3; ERBB4; Erythropoietin, Factor IX, Factor V; Factor VII, Factor VII; Factor VIII; Factor VIIIa light chain, Factor X; Factor XI (F11); Factor XII deficiency (F12, HAF); Factor XIIIA (F13A1, F13A); Factor XIIIB (F13B); FBN1, FGF Receptor Family members; FHL3; FKRP, FXN/X25; FXR1, G6PC, G6PT, GAA, Galactose-1-phosphate uridylyltransferase, GLUT2, H1Fla; HBA1; HBB; HBA2, HBB, HBD, Heparan N-sulfatase, HIF; HIF3a; HLH3, HPLH2, HPLH3, Huntingtin, IDH2; IDH1, IGF Receptor, IGF; IGF1R, Igf2 Receptor; Igf2; Igf1 Receptor, Igf1; ITGB2, KIAA1596; Kras; LCRB, Methylmalonyl-CoA mutase, MRP7, MUNC13-4, N-acetyl-alpha-D-glucosaminidase, NOS3, NPC1, OTC (Ornithine transcarbamylase), PAH, PKHD1, PKD1, PKD2, PKD4, PKLR, PKU1, PPAR gamma; PPARalpha; PRF1, PSEN2, PSF2, PTEN; RB, Retinoschisin; RING11, SBMA/SMAXI/AR; SEC63, SERPINA1, SERPINA2, SERPINA3, SERPINA5, SERPINA6, SFTPA1, SFTPB, SFTPC, SFTPD, SLC2A, SLC7A9, SMPD1, SPTB, TAP2, TAPBP, TPSN, UNC13D, VEGF-a, VEGF-b, VEGF-c, VLDLR; and WT1.

In some embodiments, the protein is a CFTR protein. In some embodiments, the protein is an OTC protein.

In some embodiments, a method of the invention results in high recovery of total purified mRNA. In some embodiments, the purified mRNA is recovered in an amount that results in a yield of about 85% or greater, 90% or greater, 91% or greater, 92% or greater, 93% or greater, 94% or greater, 95% or greater, 96% or greater, 97% or greater, 98% or greater or 99% or greater. In some embodiments, the total purified mRNA is recovered in an amount that results in a yield of at least about 99%.

In some embodiments, the total purified mRNA is substantially free of a protein contaminant.

In some embodiments, the total purified mRNA is substantially free of short abortive transcript contaminant.

In some embodiments, the total purified mRNA has greater than 95% integrity.

In some embodiments, the purity of the purified mRNA is determined by electrophoresis. In some embodiments, the purity of the mRNA is determined by capillary electrophoresis. In some embodiments, the purity of the purified mRNA is determined by chromatography. In some embodiments, the purity of the purified mRNA is determined by HPLC.

In some embodiments, at least about 0.5 grams of RNA is purified. In some embodiments, at least about 1 gram of RNA is purified. In some embodiments, at least about 10 grams of RNA is purified. In some embodiments, at least about 50 grams of RNA is purified. In some embodiments, at least about 100 grams of RNA is purified. In some embodiments, at least about 1 kilograms of RNA is purified.

In particular embodiments, the invention provides a method of purifying a composition comprising 100 gm or more of mRNA manufactured by in vitro transcription (IVT) synthesis, the method comprising: precipitating the NT-transcribed mRNA comprising one or more contaminants from the IVT synthesis to generate a suspension; subjecting the suspension comprising the precipitated mRNA and contaminants to normal flow filtration through a filter, where the precipitated mRNA is retained by the filter, washing the mRNA retained on the filter; recovering the mRNA from the filter in a solution, thereby purifying the mRNA, wherein at least 85% of the mRNA is recovered and the recovered mRNA has an integrity of 90% or greater and is substantially free of protein contaminants.

In various embodiments, a suitable filter (e.g., a polypropylene felt filter) has a total surface area of up to about 264 square meters or more. In various embodiments, a suitable filter (e.g., a polypropylene felt filter) has a total surface area of up to about 528 square meters or more. In various embodiments, a suitable filter (e.g., a polypropylene felt filter) has a total surface area of up to about 1056 square meters or more.

In various embodiments, the purified mRNA using a method based on normal flow filtration described herein has a clinical grade purity without any further purification steps. As used herein, the term "clinical grade" refers to a grade of sufficient purity for clinical use. In some embodiments, a clinical grade refers to a purity that meets or exceeds requirement by the US Pharmacopoeia (USP) or the National Formulary (NF), or the standards set forth by British Pharmacopoeia, and European Pharmacopoeia. In some embodiments, the term "pharmacopoeia grade" is used interchangeably with "clinical grade".

In some embodiments, the clinical grade purity is achieved without the further purification steps selected from HPLC purification, ligand or binding based purification, TFF purification, and/or ion exchange chromatography.

In various embodiments, the purified mRNA according to a method described herein is determined to comprise 5% or less, 4% or less, 3% or less, 2% or less, or 1% or less protein contaminants as determined by capillary electrophoresis. In certain embodiments, the purified mRNA according to a method described herein is determined to comprise 5% or less protein contaminants as determined by capillary electrophoresis. In certain embodiments, the purified mRNA according to a method described herein is determined to comprise 4% or less protein contaminants as determined by capillary electrophoresis. In certain embodiments, the purified mRNA according to a method described herein is determined to comprise 3% or less protein contaminants as determined by capillary electrophoresis. In certain embodiments, the purified mRNA according to a method described herein is determined to comprise 2% or less protein contaminants as determined by capillary electrophoresis. In certain embodiments, the purified mRNA according to a method described herein is determined to comprise 1% or less protein contaminants as determined by capillary electrophoresis.

In various embodiments, the purified mRNA according to a method described herein is determined to comprise 5% or less, 4% or less, 3% or less, 2% or less or 1% or less protein contaminants by HPLC. In certain embodiments, the purified mRNA according to a method described herein is determined to comprise 5% or less protein contaminants by HPLC. In certain embodiments, the purified mRNA according to a method described herein is determined to comprise 4% or less protein contaminants by HPLC. In certain embodiments, the purified mRNA according to a method described herein is determined to comprise 3% or less protein contaminants by HPLC. In certain embodiments, the purified mRNA according to a method described herein is determined to comprise 2% or less protein contaminants by HPLC. In certain embodiments, the purified mRNA according to a method described herein is determined to comprise 1% or less protein contaminants by HPLC.

In various embodiments, the purified mRNA according to a method described herein is determined to comprise less than 5%, less than 4%, less than 3%, less than 2% or less than 1% salt contaminants by HPLC. In certain embodiments, the purified mRNA according to a method described herein is determined to comprise 5% or less salt contaminants by HPLC. In certain embodiments, the purified mRNA according to a method described herein is determined to comprise 4% or less salt contaminants by HPLC. In certain embodiments, the purified mRNA according to a method described herein is determined to comprise 3% or less salt contaminants by HPLC. In certain embodiments, the purified mRNA according to a method described herein is determined to comprise 2% or less salt contaminants by HPLC. In certain embodiments, the purified mRNA according to a method described herein is determined to comprise 1% or less salt contaminants by HPLC.

In various embodiments, the purified mRNA is determined to comprise 5% or less, 4% or less, 3% or less, 2% or less or 1% or less short abortive RNA contaminants by capillary electrophoresis. In certain embodiments, the purified mRNA is determined to comprise 5% or less short abortive RNA contaminants by capillary electrophoresis. In certain embodiments, the purified mRNA is determined to comprise 4% or less short abortive RNA contaminants by capillary electrophoresis. In certain embodiments, the purified mRNA is determined to comprise 3% or less short abortive RNA contaminants by capillary electrophoresis. In certain embodiments, the purified mRNA is determined to comprise 2% or less short abortive RNA contaminants by capillary electrophoresis. In certain embodiments, the purified mRNA is determined to comprise 1% or less short abortive RNA contaminants by capillary electrophoresis.

In various embodiments, the purified mRNA is determined to comprise 5% or less, 4% or less, 3% or less, 2% or less or 1% or less short abortive RNA contaminants as determined by HPLC. In certain embodiments, the purified mRNA is determined to comprise 5% or less short abortive RNA contaminants as determined by HPLC. In certain embodiments, the purified mRNA is determined to comprise 4% or less short abortive RNA contaminants as determined by HPLC. In certain embodiments, the purified mRNA is determined to comprise 3% or less short abortive RNA contaminants as determined by HPLC. In certain embodiments, the purified mRNA is determined to comprise 2% or less short abortive RNA contaminants as determined by HPLC. In certain embodiments, the purified mRNA is determined to comprise 1% or less short abortive RNA contaminants as determined by HPLC.

In various embodiments, the purified mRNA is determined to comprise an integrity of 95% or greater, 96% or greater, 97% or greater, 98% or greater, or 99% or greater as determined by capillary electrophoresis. In certain embodiments, the purified mRNA is determined to comprise an integrity of 95% or greater as determined by capillary electrophoresis. In certain embodiments, the purified mRNA is determined to comprise an integrity of 96% or greater as determined by capillary electrophoresis. In certain embodiments, the purified mRNA is determined to comprise an integrity of 97% or greater as determined by capillary electrophoresis. In certain embodiments, the purified mRNA is determined to comprise an integrity of 98% or greater as determined by capillary electrophoresis. In certain embodiments, the purified mRNA is determined to comprise an integrity of 98% or greater as determined by capillary electrophoresis. In certain embodiments, the purified mRNA is determined to comprise an integrity of 99% or greater as determined by capillary electrophoresis.

Among other things, the present invention provides a composition comprising mRNA purified using various methods described herein. In some embodiments, the composition is a pharmaceutical composition comprising the purified mRNA described herein and at least one pharmaceutically-acceptable excipient. The present invention also provides methods for treating a disease or disorder including administering to a subject in need thereof a pharmaceutical composition described herein.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Other features and advantages of the invention will be apparent from the Drawings and the following detailed description and claims.

BRIEF DESCRIPTION OF THE DRAWINGS

The above and further features will be more clearly appreciated from the following detailed description when taken in conjunction with the accompanying drawings. The drawings however are for illustration purposes only; not for limitation.

FIG. 8A shows concentration (mg/ml) of recovered mRNA over recirculation time. FIG. 8B expresses the recovered mRNA percent over recirculation time.

FIG. 14A shows concentration (mg/ml) of recovered mRNA over recirculation time. FIG. 14B expresses the recovered mRNA percent over recirculation time.

FIG. 15A—control CFTR mRNA purified by a prior method without using normal flow depth filtration. FIG. 15B CFTR mRNA purified by normal flow depth filtration.

DEFINITIONS

Figure 1:
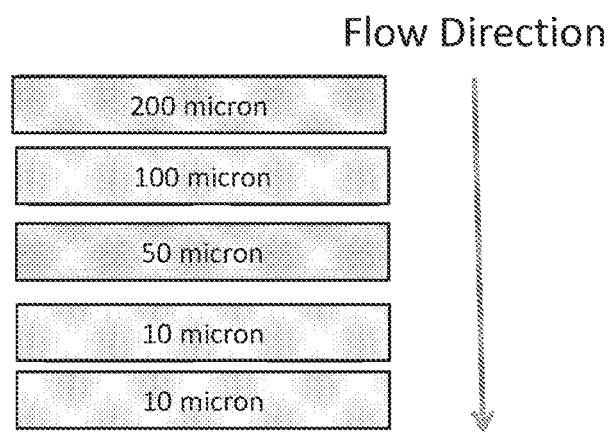
FIG. 1 illustrates an exemplary depth filter design.

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The terms "e.g.," and "i.e." as used herein, are used merely by way of example, without limitation intended, and should not be construed as referring only those items explicitly enumerated in the specification.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or obvious from context, as used herein, the term "about" is understood as within a range of normal tolerance in the art, for example within 2 standard deviations of the mean. "About" can be understood to be within 10%, 9%, 8%, 7%, 6%, 5%, 4%, 3%, 2%, 1%, 0.5%, 0.1%, 0.05%, 0.01%, or 0.001% of the stated value. Unless otherwise clear from the context, all numerical values provided herein are modified by the term "about".

As used herein, the term "batch" refers to a quantity or amount of mRNA synthesized at one time, e.g., produced according to a single manufacturing order during the same cycle of manufacture. A batch may refer to an amount of mRNA synthesized in one reaction that occurs via a single aliquot of enzyme and/or a single aliquot of DNA template for continuous synthesis under one set of conditions. In some embodiments, a batch would include the mRNA produced from a reaction in which not all reagents and/or components are supplemented and/or replenished as the reaction progresses. The term "batch" would not mean mRNA synthesized at different times that are combined to achieve the desired amount.

As used herein, the term "contaminants" refers to substances inside a confined amount of liquid, gas, or solid, which differ from the chemical composition of the target material or compound. Contaminants are also referred to as impurities. Examples of contaminants or impurities include buffers, proteins (e.g., enzymes), nucleic acids, salts, solvents, and/or wash solutions.

As used herein, the term "dispersant" refers to a solid particulate which reduces the likelihood that an mRNA precipitate will form a hydrogel. Examples of dispersants include and are not limited to one or more of ash, clay, diatomaceous earth, filtering agent, glass beads, plastic beads, polymers, polypropylene beads, polystyrene beads, salts (e.g., cellulose salts), sand, and sugars. In embodiments, a dispersant is polymer microspheres (e.g., poly (styrene-co-divinylbenezene) microspheres).

As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end formation); (3) translation of an mRNA into a polypeptide or protein; and/or (4) post-translational modification of a polypeptide or protein. In this application, the terms "expression" and "production," and grammatical equivalent, are used inter-changeably.

As used herein, "flux" is flow rate divided by filter area. It allows for comparisons across different scales of filters.

As used herein, "full-length mRNA" is as characterized when using a specific assay, e.g., gel electrophoresis or detection using UV and UV absorption spectroscopy with separation by capillary electrophoresis. The length of an mRNA molecule that encodes a full-length polypeptide and as obtained following any of the purification methods described herein is at least 50% of the length of a full-length mRNA molecule that is transcribed from the target DNA, e.g., at least 60%, 70%, 80%, 90%, 91%, 92%, 93%, 94%, 95%, 96%, 97%, 98%, 99%, 99.01%, 99.05%, 99.1%, 99.2%, 99.3%, 99.4%, 99.5%, 99.6%, 99.7%, 99.8%, 99.9% of the length of a full-length mRNA molecule that is transcribed from the target DNA and prior to purification according to any method described herein.

As used herein, a "functional" biological molecule is a biological molecule in a form in which it exhibits a property and/or activity by which it is characterized.

As used herein, the term "hydrogel" refers to a network of hydrophilic polymer chains, e.g., mRNA, which forms a colloidal gel in which water is the dispersion medium. Using mRNA as an example, it is more difficult to extract or purify mRNA from a hydrogel than from a dry cake.

As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man.

As used herein, the term "messenger RNA" or "mRNA" refers to a polyribonucleotide that encodes at least one polypeptide. mRNA as used herein encompasses both modified and unmodified mRNA. mRNA may contain one or more coding and non-coding regions. mRNA can be purified from natural sources, produced using recombinant expression systems and optionally purified, in vitro transcribed, or chemically synthesized.

mRNA is typically thought of as the type of RNA that carries information from DNA to the ribosome. The existence of mRNA is usually very brief and includes processing and translation, followed by degradation. Typically, mRNA includes a nucleotide sequence having a coding region that codes for a polypeptide, a 5' untranslated region (5' UTR) upstream of the coding region, a 3'untranslated region (3' UTR) downstream of the coding region, a cap at the 5' terminus and a polyA or polyadenylation region downstream of the 3'UTR. Typically, in eukaryotic organisms, mRNA processing comprises transcription of the mRNA from DNA and the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA typically is translated by the ribosomes into a series of amino acids that make up a protein.

In some embodiments, an mRNA of the present invention lacks one or both of a cap and/or a tail. Thus, an mRNA may have a cap and lack a tail, an mRNA may have a tail and lack a cap, and an mRNA may lack a cap and lack a tail.

As used herein, the term "mRNA integrity" generally refers to the quality of mRNA. In some embodiments, mRNA integrity refers to the percentage of mRNA that is not degraded after a purification process (e.g., a method described herein). mRNA integrity may be determined using methods particularly described herein, such as TAE Agarose gel electrophoresis or by SDS-PAGE with silver staining, or by methods well known in the art, for example, by RNA agarose gel electrophoresis (e.g., Ausubel et al., John Wiley & Sons, Inc., 1997, Current Protocols in Molecular Biology).

As used herein, the term "pharmaceutically acceptable" refers to substances that, within the scope of sound medical judgment, are suitable for use in contact with the tissues of human beings and animals without excessive toxicity, irritation, allergic response, or other problem or complication, commensurate with a reasonable benefit/risk ratio.

A "pharmaceutically acceptable excipient" means an excipient that is suitable for preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate.

Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. Therefore, a composition substantially free of a compound 'x' would be understood to comprise less than 5% of the compound 'x', or less than 1%, or less than 0.1% or less than 0.01% of the compound 'x'. Unless otherwise defined, all technical and scientific terms used herein have the same meaning as commonly understood by one of ordinary skill in the art to which this application belongs and as commonly used in the art to which this application belongs; such art is incorporated by reference in its entirety. In the case of conflict, the present Specification, including definitions, will control.

DETAILED DESCRIPTION

The present invention relates to methods for preparing scalable quantities of pure and high-quality mRNA base on normal flow filtration. mRNA synthesized in vitro comprises contaminants generated during, or are carried over from, the synthesis process. Methods of the invention involve precipitating in vitro synthesized mRNA and subjecting the mRNA preparation to normal flow filtration such that the precipitated mRNA is retained in or on the filter matrix or system while allowing contaminants from the synthesis process to flow through the filter or filter system as a filtrate, thereby purifying the precipitated mRNA. The captured mRNA is then transformed into a filtrate by dissolving the mRNA precipitate, thereby allowing the mRNA to pass through the filter or the filter system where it can be collected at a purity level that is suitable for clinical or therapeutic applications without further steps to purify the mRNA (e.g., without further HPLC purification, or TFF, ion exchange chromatography, or affinity binding chromatography). Notably, this method provides for a remarkable recovery of mRNA Methods as described herein allows for manufacturing of large quantities of mRNA efficiently, with surprisingly high purity and integrity suitable for therapeutic use.

Messenger RNA

The purification methods described herein are suitable for purification of any mRNA. The present invention may be used to purify mRNAs encoding a variety of proteins (e.g., polypeptides) or peptides.

According to various embodiments, the present invention may be used to purify in vitro synthesized mRNA of a variety of lengths. In some embodiments, the present invention may be used to purify in vitro synthesized mRNA of or greater than about 1 kb, 1.5 kb, 2 kb, 2.5 kb, 3 kb, 3.5 kb, 4 kb, 4.5 kb, 5 kb, 6 kb, 7 kb, 8 kb, 9 kb, 10 kb, 11 kb, 12 kb, 13 kb, 14 kb, 15 kb, or 20 kb in length. In some embodiments, the present invention may be used to purify in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length. For example, typical mRNAs may be about 1 kb to about 5 kb in length. More typically, the mRNA will have a length of about 1 kb to about 3 kb. However, in some embodiments, the mRNA in the composition of the invention is much longer (greater than about 20 kb).

In certain embodiments, mRNA nucleotides are modified to provide "modified mRNA." A modified mRNA according to the invention can thus include, for example, backbone modifications, sugar modifications or base modifications. In some embodiments, antibody encoding mRNAs (e.g., heavy chain and light chain encoding mRNAs) may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

In some embodiments, the present invention may be used to purify in vitro synthesized mRNA that is unmodified.

In some embodiments, mRNA includes a 5' and/or 3' untranslated region (UTR). In some embodiments, a 5' untranslated region includes one or more elements that affect an mRNA's stability or translation, for example, an iron responsive element. In some embodiments, a 5' untranslated region may be between about 50 and 500 nucleotides in length. In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer. In some embodiments, a 5' untranslated region includes one or more elements that affect an mRNA's stability or translation, for example, an iron responsive element.

Exemplary 3' and/or 5' UTR sequences can be derived from mRNA molecules which are stable (e.g., globin, actin, GAPDH, tubulin, histone, and citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these features improve the stability and/or pharmacokinetic properties (e.g., half-life) of the polynucleotide relative to the same polynucleotide without such features, and include, for example features made to improve such polynucleotides' resistance to in vivo nuclease digestion.

In some embodiments an mRNA encodes an intracellular protein. In some embodiments, an mRNA encodes a cytosolic protein. In some embodiments, an mRNA encodes a protein associated with the actin cytoskeleton. In some embodiments, an mRNA encodes a protein associated with the plasma membrane. In some specific embodiments, an mRNA encodes a transmembrane protein. In some specific embodiments an mRNA encodes an ion channel protein. In some embodiments, an mRNA encodes a perinuclear protein. In some embodiments, an mRNA encodes a nuclear protein. In some specific embodiments, an mRNA encodes a transcription factor. In some embodiments, an mRNA encodes a chaperone protein. In some embodiments, an mRNA encodes an intracellular enzyme (e.g., mRNA encoding an enzyme associated with urea cycle or lysosomal storage metabolic disorders). In some embodiments, an mRNA encodes a protein involved in cellular metabolism, DNA repair, transcription and/or translation. In some embodiments, an mRNA encodes an extracellular protein. In some embodiments, an mRNA encodes a protein associated with the extracellular matrix. In some embodiments an mRNA encodes a secreted protein. In specific embodiments, an mRNA used in the composition and methods of the invention may be used to express functional proteins or enzymes that are excreted or secreted by one or more target cells into the surrounding extracellular fluid (e.g., mRNA encoding hormones and/or neurotransmitters). In some embodiments an mRNA encodes an immunogenic protein for vaccine purposes. In some embodiments an mRNA encodes an antibody or a fragment therefore. In some embodiments, an mRNA encodes a metabolic protein. In some embodiments, an mRNA encodes an enzyme. In some embodiments, an mRNA encodes a receptor protein. In some embodiments, an mRNA encodes an antigen. In some embodiments, an mRNA encodes a cancer associated antigen. In some embodiments, an mRNA encodes a vaccine.

As non-limiting examples, an mRNA encodes a protein such as ABC7, ABCB3, ABCB7, ABCC7, ABCD1, AKT; AKT2, AKT3. ATF4, AKT2; AKT3; ALAS2, Alpha galactosidase, Alpha-1 Protease inhibitor, APA, APC; APOA1, APOE, Anti-trypsin alpha 1, Arginosuccinate synthase, ASAT; ATM; ATP7B, ATR; Atrophin-1; ATX3; Atxn10; ATXN2; Atxn7; ATXNl; Bax; Bcl2; Bcl2; BRCA1; BRCA2; Carbamylphosphate Synthase, CASP8, CBP (Creb-BP); CDKN2a; CFTR, CREB1, CVAP, CYP1Bl, DBA, DMD, DMPK; EGFR, EIF2B1, EIF2BA, EIF2B2, EIF2B3, EIF2B5, EIF2B4; ERBB2; ERBB3; ERBB4; Erythropoietin, Factor IX, Factor V; Factor VII, Factor VII; Factor VIII; Factor VIIIa light chain, Factor X; Factor XI (F11); Factor XII deficiency (F12, HAF); Factor XIIIA (F13Al, F13A); Factor XIIIB (F13B); FBN1, FGF Receptor Family members; FHL3; FKRP, FXN/X25; FXR1, G6PC, G6PT, GAA, Galactose-1-phosphate uridylyltransferase, GLUT2, H1Fla; HBA1; HBB; HBA2, HBB, HBD, Heparan N-sulfatase, HIF; HIF3a; HLH3, HPLH2, HPLH3, Huntingtin, IDH2; IDH1, IGF Receptor; IGF; IGF1R, Igf2 Receptor, Igf2; Igf1 Receptor; Igf1; ITGB2, KIAA1596; Kras; LCRB, Methylmalonyl-CoA mutase, MRP7, MUNC13-4, N-acetyl-alpha-D-glucosaminidase, NOS3, NPC1, OTC (Ornithine transcarbamylase), PAH, PKHD1, PKD1, PKD2, PKD4, PKLR, PKU1, PPAR gamma; PPARalpha; PRF1, PSEN2, PSF2, PTEN; RB, Retinoschisin; RING1, SBMA/SMAXl/AR; SEC63, SERPINA1, SERPINA2, SERPINA3, SERPINA5, SERPINA6, SFTPA1, SFTPB, SFTPC, SFTPD, SLC2A, SLC7A9, SMPD1, SPTB, TAP2, TAPBP, TPSN, UNC13D, VEGF-a, VEGF-b, VEGF-c, VLDLR; and WT1.

In certain embodiments the present invention provides a method for purifying mRNA that encodes a peptide or polypeptide for treatment of the lung of a subject or a lung cell. In certain embodiments the present invention provides a method for purifying mRNA that encodes an endogenous protein which may be deficient or non-functional in a subject. In certain embodiments the present invention provides a method for purifying mRNA that encodes a polypeptide in a therapeutic mRNA vaccine for a subject.

In certain embodiments the present invention provides a method for purifying mRNA that encodes a peptide or polypeptide for use in the delivery to or treatment of the lung of a subject or a lung cell. In certain embodiments the present invention provides a method for purifying mRNA encoding cystic fibrosis transmembrane conductance regulator, CFTR. The purified CFTR mRNA can be delivered to the lung of a subject in need in a therapeutic composition for treating cystic fibrosis. In certain embodiments the present invention provides a method for purifying mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with purified mRNA provides therapeutic benefit.

In certain embodiments the present invention provides a method for purifying mRNA that encodes for a protein associated with a urea cycle disorder. In certain embodiments the present invention provides a method for purifying mRNA that encodes for ornithine transcarbamylase (OTC) protein. In certain embodiments the present invention provides a method for purifying mRNA that encodes for arginosuccinate synthetase 1 protein. In certain embodiments the present invention provides a method for purifying mRNA that encodes for carbamoyl phosphate synthetase I protein. In certain embodiments the present invention provides a method for purifying mRNA that encodes for arginosuccinate lyase protein. In certain embodiments the present invention provides a method for purifying mRNA that encodes for arginase protein.

In certain embodiments the present invention provides a method for purifying mRNA that encodes for a protein associated with a lysosomal storage disorder. In certain embodiments the present invention provides a method for purifying mRNA that encodes for alpha galactosidase protein. In certain embodiments the present invention provides a method for purifying mRNA that encodes for glucocerebrosidase protein. In certain embodiments the present invention provides a method for purifying mRNA that encodes for iduronate-2-sulfatase protein. In certain embodiments the present invention provides a method for purifying mRNA that encodes for iduronidase protein. In certain embodiments the present invention provides a method for purifying mRNA that encodes for N-acetyl-alpha-D-glucosaminidase protein. In certain embodiments the present invention provides a method for purifying mRNA that encodes for heparan N-sulfatase protein. In certain embodiments the present invention provides a method for purifying mRNA that encodes for galactosamine-6 sulfatase protein. In certain embodiments the present invention provides a method for purifying mRNA that encodes for beta-galactosidase protein. In certain embodiments the present invention provides a method for purifying mRNA that encodes for lysosomal lipase protein. In certain embodiments the present invention provides a method for purifying mRNA that encodes for arylsulfatase B (N-acetylgalactosamine-4-sulfatase) protein. In certain embodiments the present invention provides a method for purifying mRNA that encodes for transcription factor EB (TFEB).

In certain embodiments the present invention provides a method for purifying mRNA that encodes for a protein associated with a glycogen storage disorder. In certain embodiments the present invention provides a method for purifying mRNA that encodes for acid alpha-glucosidase protein. In certain embodiments the present invention provides a method for purifying mRNA that encodes for glucose-6-phosphatase (G6PC) protein. In certain embodiments the present invention provides a method for purifying mRNA that encodes for liver glycogen phosphorylase protein. In certain embodiments the present invention provides a method for purifying mRNA that encodes for muscle phosphoglycerate mutase protein. In certain embodiments the present invention provides a method for purifying mRNA that encodes for glycogen debranching enzyme.

In certain embodiments the present invention provides a method purifying mRNA that encodes for a protein associated with amino acid metabolism. In certain embodiments the present invention provides a method for purifying mRNA that encodes for phenylalanine hydroxylase enzyme. In certain embodiments the present invention provides a method for purifying mRNA that encodes for glutaryl-CoA dehydrogenase enzyme. In certain embodiments the present invention provides a method for purifying mRNA that encodes for propionyl-CoA caboxylase enzyme. In certain embodiments the present invention provides a method for purifying mRNA that encodes for oxalase alanine-glyoxylate aminotransferase enzyme.

In certain embodiments the present invention provides a method for purifying mRNA that encodes for a protein associated with a lipid metabolism or fibrotic disorder. In certain embodiments the present invention provides a method for purifying mRNA that encodes for a mTOR inhibitor. In certain embodiments the present invention provides a method for purifying mRNA that encodes for ATPase phospholipid transporting 8B1 (ATP8B1) protein. In certain embodiments the present invention provides a method for purifying mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for purifying mRNA that encodes for PPAR-gamma protein or an active variant.

In certain embodiments the present invention provides a method for purifying mRNA that encodes for a protein associated with methylmalonic acidemia. For example, in certain embodiments the present invention provides a method for purifying mRNA that encodes for methylmalonyl CoA mutase protein. In certain embodiments the present invention provides a method for purifying mRNA that encodes for methylmalonyl CoA epimerase protein.

In certain embodiments the present invention provides a method for purifying mRNA for which delivery to or treatment of the liver can provide therapeutic benefit. In certain embodiments the present invention provides a method for purifying mRNA that encodes for ATP7B protein, also known as Wilson disease protein. In certain embodiments the present invention provides a method for purifying mRNA that encodes for porphobilinogen deaminase enzyme. In certain embodiments the present invention provides a method for purifying mRNA that encodes for one or clotting enzymes, such as Factor VIII, Factor IX, Factor VII, and Factor X. In certain embodiments the present invention provides a method for purifying mRNA that encodes for Factor IX. In certain embodiments the present invention provides a method for purifying mRNA that encodes for human hemochromatosis (HFE) protein.

In certain embodiments the present invention provides a method for purifying mRNA that encodes a peptide or polypeptide for use in the delivery to or treatment of the cardiovasculature of a subject or a cardiovascular cell. In certain embodiments the present invention provides a method for purifying mRNA that encodes for vascular endothelial growth factor A protein. In certain embodiments the present invention provides a method for purifying mRNA that encodes for relaxin protein. In certain embodiments the present invention provides a method for purifying mRNA that encodes for bone morphogenetic protein-9 protein. In certain embodiments the present invention provides a method for purifying mRNA that encodes for bone morphogenetic protein-2 receptor protein.

In certain embodiments the present invention provides a method for purifying mRNA that encodes a peptide or polypeptide for use in the delivery to or treatment of the muscle of a subject or a muscle cell. In certain embodiments the present invention provides a method for purifying mRNA that encodes for dystrophin protein. In certain embodiments the present invention provides a method for purifying mRNA that encodes for frataxin protein. In certain embodiments the present invention provides a method for purifying mRNA that encodes a peptide or polypeptide for use in the delivery to or treatment of the cardiac muscle of a subject or a cardiac muscle cell. In certain embodiments the present invention provides a method for purifying mRNA that encodes for a protein that modulates one or both of a potassium channel and a sodium channel in muscle tissue or in a muscle cell. In certain embodiments the present invention provides a method for purifying mRNA that encodes for a protein that modulates a Kv7.1 channel in muscle tissue or in a muscle cell. In certain embodiments the present invention provides a method for purifying mRNA that encodes for a protein that modulates a Nav1.5 channel in muscle tissue or in a muscle cell.

In certain embodiments the present invention provides a method for purifying mRNA that encodes a peptide or polypeptide for use in the delivery to or treatment of the nervous system of a subject or a nervous system cell. For example, in certain embodiments the present invention provides a method for purifying mRNA that encodes for survival motor neuron 1 protein. For example, in certain embodiments the present invention provides a method for purifying mRNA that encodes for survival motor neuron 2 protein. In certain embodiments the present invention provides a method for purifying mRNA that encodes for frataxin protein. In certain embodiments the present invention provides a method for purifying mRNA that encodes for ATP binding cassette subfamily D member 1 (ABCD1) protein. In certain embodiments the present invention provides a method for purifying mRNA that encodes for CLN3 protein.

In certain embodiments the present invention provides a method for purifying mRNA that encodes a peptide or polypeptide for use in the delivery to or treatment of the blood or bone marrow of a subject or a blood or bone marrow cell. In certain embodiments the present invention provides a method for purifying mRNA that encodes for beta globin protein. In certain embodiments the present invention provides a method for purifying mRNA that encodes for Bruton's tyrosine kinase protein. In certain embodiments the present invention provides a method for purifying mRNA that encodes for one or clotting enzymes, such as Factor VIII, Factor IX, Factor VII, and Factor X.

In certain embodiments the present invention provides a method for purifying mRNA that encodes a peptide or polypeptide for use in the delivery to or treatment of the kidney of a subject or a kidney cell. In certain embodiments the present invention provides a method for purifying mRNA that encodes for collagen type IV alpha 5 chain (COL4A5) protein.

In certain embodiments the present invention provides a method for purifying mRNA that encodes a peptide or polypeptide for use in the delivery to or treatment of the eye of a subject or an eye cell. In certain embodiments the present invention provides a method for purifying mRNA that encodes for ATP-binding cassette sub-family A member 4 (ABCA4) protein. In certain embodiments the present invention provides a method for purifying mRNA that encodes for retinoschisin protein. In certain embodiments the present invention provides a method for purifying mRNA that encodes for retinal pigment epithelium-specific 65 kDa (RPE65) protein. In certain embodiments the present invention provides a method for purifying mRNA that encodes for centrosomal protein of 290 kDa (CEP290).

In certain embodiments the present invention provides a method for purifying mRNA that encodes a peptide or polypeptide for use in the delivery of or treatment with a vaccine for a subject or a cell of a subject. For example, in certain embodiments the present invention provides a method for purifying mRNA that encodes for an antigen from an infectious agent, such as a virus. In certain embodiments the present invention provides a method for purifying mRNA that encodes for an antigen from influenza virus. In certain embodiments the present invention provides a method for purifying mRNA that encodes for an antigen from respiratory syncytial virus. In certain embodiments the present invention provides a method for purifying mRNA that encodes for an antigen from rabies virus. In certain embodiments the present invention provides a method for purifying mRNA that encodes for an antigen from cytomegalovirus. In certain embodiments the present invention provides a method for purifying mRNA that encodes for an antigen from rotavirus. In certain embodiments the present invention provides a method for purifying mRNA that encodes for an antigen from a hepatitis virus, such as hepatitis A virus, hepatitis B virus, or hepatis C virus. In certain embodiments the present invention provides a method for purifying mRNA that encodes for an antigen from human papillomavirus. In certain embodiments the present invention provides a method for purifying mRNA that encodes for an antigen from a herpes simplex virus, such as herpes simplex virus 1 or herpes simplex virus 2. In certain embodiments the present invention provides a method for purifying mRNA that encodes for an antigen from a human immunodeficiency virus, such as human immunodeficiency virus type 1 or human immunodeficiency virus type 2. In certain embodiments the present invention provides a method for purifying mRNA that encodes for an antigen from a human metapneumovirus. In certain embodiments the present invention provides a method for purifying mRNA that encodes for an antigen from a human parainfluenza virus, such as human parainfluenza virus type 1, human parainfluenza virus type 2, or human parainfluenza virus type 3. In certain embodiments the present invention provides a method for purifying mRNA that encodes for an antigen from malaria virus. In certain embodiments the present invention provides a method for purifying mRNA that encodes for an antigen from zika virus. In certain embodiments the present invention provides a method for purifying mRNA that encodes for an antigen from chikungunya virus.

In certain embodiments the present invention provides a method for purifying mRNA that encodes for an antigen associated with a cancer of a subject or identified from a cancer cell of a subject. In certain embodiments the present invention provides a method for purifying mRNA that encodes for an antigen determined from a subject's own cancer cell, i.e., to provide a personalized cancer vaccine. In certain embodiments the present invention provides a method for purifying mRNA that encodes for an antigen expressed from a mutant KRAS gene.

In certain embodiments the present invention provides a method for purifying mRNA that encodes for an antibody. In certain embodiments, the antibody can be a bi-specific antibody. In certain embodiments, the antibody can be part of a fusion protein. In certain embodiments the present invention provides a method for purifying mRNA that encodes for an antibody to OX40. In certain embodiments the present invention provides a method for purifying mRNA that encodes for an antibody to VEGF. In certain embodiments the present invention provides a method for purifying mRNA that encodes for an antibody to tissue necrosis factor alpha. In certain embodiments the present invention provides a method for purifying mRNA that encodes for an antibody to CD3. In certain embodiments the present invention provides a method for purifying mRNA that encodes for an antibody to CD19.

In certain embodiments the present invention provides a method for purifying mRNA that encodes for an immunomodulator. In certain embodiments the present invention provides a method for purifying mRNA that encodes for Interleukin 12. In certain embodiments the present invention provides a method for purifying mRNA that encodes for Interleukin 23. In certain embodiments the present invention provides a method for purifying mRNA that encodes for Interleukin 36 gamma. In certain embodiments the present invention provides a method for purifying mRNA that encodes for a constitutively active variant of one or more stimulator of interferon genes (STING) proteins.

In certain embodiments the present invention provides a method for purifying mRNA that encodes for an endonuclease. In certain embodiments the present invention provides a method for purifying mRNA that encodes for an RNA-guided DNA endonuclease protein, such as Cas 9 protein. In certain embodiments the present invention provides a method for purifying mRNA that encodes for a meganuclease protein. In certain embodiments the present invention provides a method for purifying mRNA that encodes for a transcription activator-like effector nuclease protein. In certain embodiments the present invention provides a method for purifying mRNA that encodes for a zinc finger nuclease protein.

In certain embodiments the present invention provides a method for purifying mRNA that encodes for treating an ocular disease. In some embodiments the method is used for purifying mRNA encoding retinoschisin.

mRNA Synthesis mRNAs may be synthesized according to any of a variety of known methods. For example, mRNAs may be synthesized via in vitro transcription (IVT). While the present invention is particularly useful to purify mRNA synthesized by in vitro transcription reactions. In some embodiments, mRNA from other sources are contemplated as within the scope of the invention including wild-type mRNA produced from bacteria, fungi, plants, and/or animals.

Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNase inhibitor. The exact conditions will vary according to the specific application. The presence of these reagents is undesirable in the final product according to several embodiments and may thus be referred to as impurities or contaminants and a preparation containing one or more of these impurities or contaminants may be referred to as an impure preparation. In some embodiments, the in vitro transcription occurs in a single batch. In some embodiments, IVT reaction includes capping and tailing reactions (CM. In some embodiments, capping and tailing reactions are performed separately from IVT reaction. In some embodiments, the mRNA is recovered from IVT reaction, followed by a first precipitation and purification of mRNA by methods described in the present application; the recovered purified mRNA is then capped and tailed, and subjected to a second precipitation and purification.

In some embodiments, the present invention may be used to purify a composition or a batch containing at least 200 mg, 300 mg, 400 mg, 500 mg, 600 mg, 700 mg, 800 mg, 900 mg, 1 g, 5 g, 10 g, 25 g, 50 g, 75 g, 100 g, 250 g, 500 g, 750 g, 1 kg, 5 kg, 10 kg, 50 kg, 100 kg, 1000 kg, or more mRNA. In some embodiments, the mRNA molecules are greater than 600, 700, 800, 900, 1000, 2000, 3000, 4000, 5000, 10,000 or more nucleotides in length; also included in the present invention is mRNA having any length in between.

IVT Reaction

IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNase inhibitor. The exact conditions will vary according to the specific application. A suitable DNA template typically has a promoter, for example a T3, T7 or SP6 promoter, for in vitro transcription, followed by desired nucleotide sequence for desired mRNA and a termination signal.

Other IVT methods are available in the art and may be used to practice the present invention.

Capping and Tailing (C/T) Reactions

Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

In vitro transcribed mRNA is modified enzymatically by the addition of a 5'$N^7$-methylguanylate Cap 0 structure using guanylate transferase and the addition of a methyl group at the 2' O position of the penultimate nucleotide resulting in a Cap 1 structure using 2' O-methyltransferase as described by Fechter, P.; Brownlee, G. G. "Recognition of mRNA cap structures by viral and cellular proteins" *J. Gen. Virology* 2005, 86, 1239-1249. Following addition of the Cap 1 structure, a poly-adenylate tail is added to the 3'end of the in vitro transcribed mRNA enzymatically using poly-A polymerase. Briefly, purified IVT mRNA is mixed with GTP, S-adenosyl methionine, RNase inhibitor, 2'-Omethyl transferase, guanylyl transferase, a reaction buffer comprising Tris-HCl, $MgCl_2$, and RNase-free $H_2O$; then incubated at 37° C. Following the incubation, a tailing reaction is initiated by adding tailing buffer comprising Tris-HCl, NaCl, $MgCl_2$, ATP, poly-A polymerase and RNase-free $H_2O$. The reaction is quenched by addition of EDTA.

Other capping and/or tailing methods are available in the art and may be used to practice the present invention.

Contaminants in In Vitro Synthesized mRNA

An mRNA product from the synthesis process for example as described above is likely to contain various contaminants (also referred to as impurities) including residual template DNA, aborted products, enzymes, including polymerase, for example SP6, or T7-polymerase, capping enzyme, for example guanylyl transferase, or methyl guanylyl transferase, tailing enzyme such as polyA polymerase, DNase 1, various salts, and prematurely aborted mRNA oligonucleotides, which are byproducts of an mRNA synthesis reaction.

mRNA Purification

A purification process according to the present invention may be carried out during or subsequent to synthesis. For example, mRNA may be purified as described herein before a cap and/or tail are added to the mRNA. In some embodiments, the mRNA is purified after a cap and/or tail are added to the mRNA. In some embodiments, the mRNA is purified after a cap is added. In some embodiments, the mRNA is purified both before and after a cap and/or tail are added to the mRNA. In general, a purification step as described herein may be performed after each step of mRNA synthesis, optionally along with other purification processes, such as dialysis.

Precipitation of mRNA

According to the present invention, mRNA may be precipitated in an impure preparation, such as an in vitro synthesis reaction mixture, using various precipitation methods known in the art. As used herein, the term "precipitation" (or any grammatical equivalent thereof) refers to the formation of an insoluble substance (e.g., solid) in a solution. When used in connection with mRNA, the term "precipitation" refers to the formation of insoluble or solid form of mRNA in a liquid.

Any and all methods suitable for precipitating mRNA may be used to practice the present invention. Typically, mRNA precipitation involves a denaturing condition. As used herein, the term "denaturing condition" refers to any chemical or physical condition that can cause disruption of native confirmation of mRNA. Since the native conformation of a molecule is usually the most water soluble, disrupting the secondary and tertiary structures of a molecule may cause changes in solubility and may result in precipitation of mRNA from solution.

For example, a suitable method of precipitating mRNA from an impure preparation involves treating the impure preparation with a denaturing reagent such that the mRNA precipitates. Exemplary denaturing reagents suitable for the invention include, but are not limited to, lithium chloride, sodium chloride, potassium chloride, guanidinium chloride, guanidinium thiocyanate, guanidinium isothiocyanate, ammonium acetate and combinations thereof. Suitable reagent may be provided in a solid form or in a solution.

As a non-limiting example, guanidinium thiocyanate (GSCN) may be used to precipitate mRNA. Typically, guanidinium thiocyanate may be provided in a solution at a concentration of about 1M or greater, of about 2M or greater, of about 3M or greater, of about 4M or greater, of about 5M or greater, of about 6M or greater, of about 7M or greater, of about 8M or greater, of about 9M or greater, or of about 10M or greater. In some embodiments, a solution suitable for mRNA precipitation contains guanidinium thiocyanate at a concentration of about 4M, or about 5M, or about 6M.

In addition to denaturing reagent, a suitable solution for mRNA precipitation may include additional salt, surfactant and/or buffering agent. For example, a suitable solution may further include sodium lauryl sarcosyl and/or sodium citrate. As non-limiting examples, a solution suitable for mRNA precipitation may contain 4M guanidinium thiocyanate. In certain embodiments, a solution suitable for mRNA precipitation may contain about 5M guanidinium thiocyanate.

Typically, it is desirable to incubate the impure preparation with one or more denaturing reagents described herein for a period of time at a desired temperature that permits precipitation of substantial amount of mRNA. For example, the mixture of an impure preparation and a denaturing agent may be incubated at room temperature or ambient temperature for a period of time. Typically, a suitable incubation time is a period of or greater than about 2, 3, 4, 5, 6, 7, 8, 9, 10, 15, 20, 25, 30, 40, 50, or 60 minutes. In some embodiments, a suitable incubation time is a period of or less than about 60, 55, 50, 45, 40, 35, 30, 25, 20, 15, 10, 9, 8, 7, 6, or 5 minutes. In some embodiments, the mixture is incubated for about 5 minutes at room temperature. Typically, "room temperature" or "ambient temperature" refers to a temperature with the range of about 20-25° C., for example, about 20° C., 21° C., 22° C., 23° C., 24° C., or 25° C. In some embodiments, the mixture of an impure preparation and a denaturing agent may also be incubated above room temperature (e.g., about 30-37° C. or in particular, at about 30° C., 31° C., 32° C., 33° C., 34° C., 35° C., 36° C., or 37° C.) or below room temperature (e.g., about 15-20° C., or in particular, at about 15° C., 16° C., 17° C., 18° C., 19° C., or 20° C.). The incubation period may be adjusted based on the incubation temperature. Typically, a higher incubation temperature requires shorter incubation time.

Alternatively or additionally, a solvent may be used to facilitate mRNA precipitation. Suitable exemplary solvent includes, but is not limited to, isopropyl alcohol, acetone, methyl ethyl ketone, methyl isobutyl ketone, ethanol, methanol, denatonium, and combinations thereof. For example, a solvent (e.g., absolute ethanol) may be added to an impure preparation together with a denaturing reagent or after the addition of a denaturing reagent and the incubation as described herein, to further enhance and/or expedite mRNA precipitation.

In some embodiments, precipitating the mRNA can include use of an organic solvent such as ethanol to precipitate the mRNA.

However, precipitating the mRNA can be achieved without the use organic solvent. In some embodiments, precipitating mRNA can be achieved using PEG to precipitate the mRNA. In some embodiments, precipitating mRNA can be achieved using PEG-6000 to precipitate the mRNA. In some embodiments, precipitating mRNA can be achieved using PEG-400 to precipitate the mRNA. In some embodiments, precipitating mRNA can be achieved using triethylene glycol (TEG) to precipitate the mRNA. In some embodiments, precipitating mRNA can be achieved using triethylene glycol monomethyl ether (MTEG) to precipitate the mRNA. In some embodiments, precipitating mRNA can be achieved using tert-butyl-TEG-O-propionate to precipitate the mRNA. In some embodiments, precipitating mRNA can be achieved using TEG-dimethacrylate to precipitate the mRNA. In some embodiments, precipitating mRNA can be achieved using TEG-dimethyl ether to precipitate the mRNA. In some embodiments, precipitating mRNA can be achieved using TEG-divinyl ether to precipitate the mRNA. In some embodiments, precipitating mRNA can be achieved using TEG-monobutyl ether to precipitate the mRNA. In some embodiments, precipitating mRNA can be achieved using TEG-methyl ether methacrylate to precipitate the mRNA. In some embodiments, precipitating mRNA can be achieved using TEG-monodecyl ether to precipitate the mRNA. In some embodiments, precipitating mRNA can be achieved using TEG-dibenzoate to precipitate the mRNA. Any one of these PEG or TEG based reagents can be used in combination with guanidinium thiocyanate to precipitate the mRNA. The structures of each of these reagents is shown below in Table A.

TABLE A

Non-Organic Solvent Reagents for Purification of mRNA (Precipitation and/or Washing of mRNA)

| Reageant Name | Structure |
| --- | --- |
| TEG | HO~~O~~O~~OH |
| TEG-monomethyl ether | H-O~~O~~O~~O- |
| tert-butyl-TEG-O-propionate | (t-Bu)O-C(=O)-CH2CH2-O~~O~~O~~OH |

TABLE A-continued

Non-Organic Solvent Reagents for Purification of mRNA (Precipitation and/or Washing of mRNA)

| Reageant Name | Structure |
| --- | --- |
| TEG-dimethacrylate | 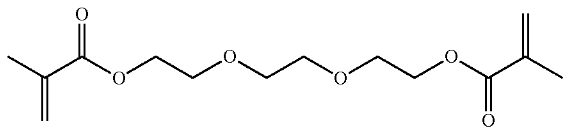 [SMILES: C=C(C)C(=O)OCCOCCOCCOC(=O)C(=C)C] |
| TEG-dimethyl ether | 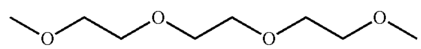 |
| TEG-divinyl ether | 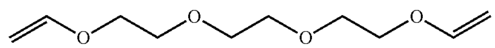 |
| TEG-monobutyl ether | 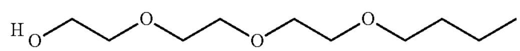 |
| TEG-methyl ether methacrylate | 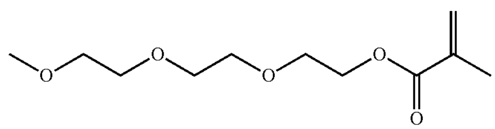 [SMILES: C=C(C)C(=O)OCCOCCOCCOC] |
| TEG-monodecyl ether | 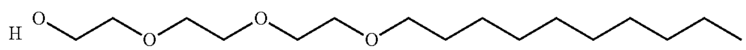 |
| TEG-dibenzoate | 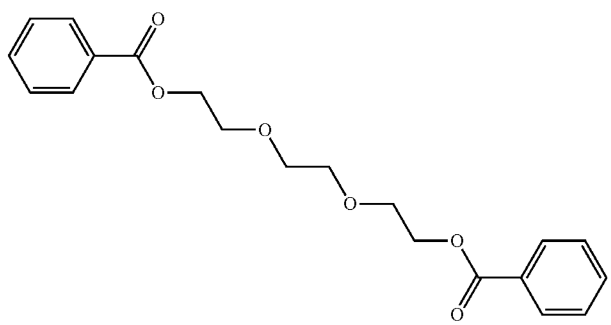 [SMILES: O=C(OCCOCCOCCOC(=O)c1ccccc1)c1ccccc1] |

Typically, after the addition of a suitable solvent (e.g., absolute ethanol), the mixture may be incubated at room temperature for another period of time. Typically, a suitable period of incubation time is or greater than about 2, 3, 4, 5, 6, 7, 8, 9, 10, 15, 20, 25, 30, 40, 50, or 60 minutes. In some embodiments, a suitable period of incubation is a period of or less than about 60, 55, 50, 45, 40, 35, 30, 25, 20, 15, 10, 9, 8, 7, 6, or 5 minutes. Typically, the mixture is incubated at room temperature for another about 5 minutes. Temperature above or below room may be used with proper adjustment of incubation time. Alternatively, incubation could occur at 4° C. or −20° C. for precipitation.

Typically, methods described herein result in precipitation of a substantial amount of mRNA from an impure preparation. In some embodiments, methods described herein result in precipitation of at least about 80%, 85%, 90%, 95%, 96%, 97%, 98%, or 99% of total mRNA from an impure preparation. In some embodiments, methods described herein result in precipitation of substantially 100% of total mRNA from an impure preparation.

Typically, as a result of precipitation, a suspension containing precipitated mRNA and various contaminants described herein is formed and subjected to normal flow filtration.

Normal Flow Filtration

Normal Flow Filtration is a filtration process in which the entirety of the material or product to be purified flows in a direction normal (i.e., perpendicular) to the surface of the filter. Materials that are too large to pass through the filter are retained whereas smaller materials pass through to the filtrate.

Typically, a normal flow filtration process described herein includes the steps of loading, washing and recovering the mRNA. The loading step involves loading the feed (e.g., an impure preparation containing precipitated mRNA) onto a filter system. The feed may be loaded under various conditions, including but not limited to, constant flow, constant pressure, variable flow, variable pressure, flow by wicking and/or gravity control.

Normal flow filtration may be performed with or without a dispersant added to the load (e.g., suspension). In some embodiments, a suspension comprising precipitated mRNA is subject to normal flow filtration without a dispersant.

Various normal flow filtration process systems and methods known in the art may be used or adapted to practice the present invention. Various filters may be used in a normal flow filtration system, including but not limited to various membrane filters, depth filters, where a filter comprising one or more three-dimensional matrices. One or multiple filters with various molecule weight cut off (MWCO), pore sizes, surface areas or format may be used. In some embodiments, multiple filters may be stacked. In some embodiments, one or more filter screens are used. Filters are selected to facilitate capturing or retaining the precipitated mRNA and allowing contaminants to pass through. Typically, suitable MWCO or pore sizes are chosen to be smaller than the precipitated mRNA and larger than soluble mRNA or other contaminants. Suitable surface areas are chosen to facilitate capturing sufficiently large amount of precipitated mRNA and allowing distribution of captured mRNA without clogging or forming a gel layer. Exemplary filters are described in more details below.

Filters

Suitable filters for the present invention comprise a variety of formats, for example, pleated filter, wrapped filter, or capsule filter. In some embodiments, a suitable filter is a depth filter. In some embodiments, a suitable filter is a membrane filter. In some embodiments, a suitable filter comprises a filter screen. Particles of interest (i.e., precipitated mRNA) in a suspension are retained on or in filters, whereas the suspension with solubilized contaminants or contaminant particles having smaller sizes flow through the filter, which is typically referred to as filtrate.

Typically, a filter with suitable pore size is selected, such that the molecular weight cut off (MWCO) value of the membrane is typically less than the minimum molecular weight of precipitated mRNA, but greater than the molecular weight of dissolved contaminants. In some embodiments, a membrane with pore size two to six (e.g., 2, 3, 4, 5, or 6) times below the MWCO of the precipitated mRNA is used. For mRNA purification, a membrane filter typically has a MWCO ranging between 1 Kilo Dalton (kDa) and 10,000 Kilo Daltons (kDa) (e.g., 10 kDa-9,000 kDa, 50 kDa-8,000 kDa, 100 kDa-9,000 kDa, 100 kDa-8,000 kDa, 100 kDa-7,000 kDa, 100 kDa-6,000 kDa, 100 kDa-5,000 kDa, 100 kDa-4,000 kDa, 100 kDa-3,000 kDa, 100 kDa-2,000 kDa, or 100 kDa-1,000 kDa). Exemplary suitable membrane filters may have a MWCO value of or greater than 1 kDa, 2 kDa, 3 kDa, 4 kDa, 5 kDa, 6 kDa, 7 kDa, 8 kDa, 9 kDa, 10 kDa, 12 kDa, 15 kDa, 20 kDa, 25 kDa, 30 kDa, 40 kDa, 50 kDa, 60 kDa, 70 kDa, 80 kDa, 90 kDa or 100 kDa. In some embodiments, suitable membrane filters may have a MWCO value of or greater than 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 350 kDa, 400 kDa, 450 kDa, 500 kDa, or 1000 kDa. In some embodiments, suitable membrane filters for the present invention may have a MWCO value of or less than about 100 kDa, 300 kDa, 500 kDa, 1,000 kDa, 1,500 kDa, 2,000 kDa, 2,500 kDa, 3,000 kDa, 3,500 kDa, 4,000 kDa, 4,500 kDa, 5,000 kDa, 5,500 kDa, 6,000 kDa, 6,500 kDa, 7,000 kDa, 7,500 kDa, 8,000 kDa, 8,500 kDa, 9,000 kDa, 9,500 kDa, or 10,000 kDa.

In some embodiments, pore sizes of filters are also measured in average pore diameter. For example, suitable filters may have an average pore size ranging between 0.001 and 500 μm, between 0.01 μm and 400 μm, between 0.01 μm and 300 μm, between 0.01 μm and 200 μm, between 0.01 μm and 100 μm, between 0.05 μm and 500 μm, between 0.05 μm and 400 μm, between 0.05 μm and 300 μm, between 0.05 μm and 200 μm, or between 0.05 μm and 100 μm. In some embodiments, a suitable filter has an average pore size of 0.001 μm or greater, 0.01 μm or greater, 0.05 μm or greater, 0.01 μm or greater, 0.1 μm or greater, 0.2 μm or greater, 0.3 μm or greater, 0.4 μm or greater, 0.5 μm or greater, 1 μm or greater, 5 μm or greater, 10 μm or greater, 15 μm or greater, 20 μm or greater, 25 μm or greater, 30 μm or greater, 35 μm or greater, 40 μm or greater, 45 μm or greater, or 50 μm or greater. In some embodiments, the filter has an average pore size of 0.5 μm or greater. In some embodiments, the filter has an average pore size of 5 μm or greater. In some embodiments, the filter has an average pore size of 10 μm or greater. In some embodiments, the filter has an average pore size of 20 μm or greater. In some embodiments, the filter has an average pore size of 25 μm or greater. In some embodiments, a suitable membrane has an average pore size of or greater than about 0.10 μm, 0.20 μm, 0.22 μm, 0.24 μm, 0.26 μm, 0.28 μm, 0.30 μm, 0.40 μm, 0.5 μm, 0.6 μm, 0.7 μm, 0.8 μm, 0.9 μm, or 1.0 μm.

A suitable filter for the present invention may be made of any material. Exemplary materials include, but are not limited to, polyethersulfone (PES) (not modified), polyethersulfone (mPES), polyvinylidene fluoride (PVDF), cellulose acetate, nitrocellulose, MCE (mixed cellulose esters), ultra-high MW polyethylene (UPE), polyfluorotetraethylene (PTFE), nylon, polysulfone, polyacrilonitrile, polypropylene, polyvinyl chloride, diatomaceous earth, glass filter and combination thereof.

A suitable filter for the present invention may have various surface area. Typically, a suitable filter has a sufficiently large surface area to facilitate large scale production of mRNA. In particular, a suitable filter has a surface area that allows capturing large amount of precipitated mRNA without clogging or forming a gel layer. For example, a suitable filter may have a surface area of or greater than about 1,000 cm$^2$, 1,500 cm$^2$, 2,000 cm$^2$, 2,500 cm$^2$, 3,000 cm$^2$, 3,500 cm$^2$, 3,500 cm$^2$, 4,000 cm$^2$, 5,000 cm$^2$, 7,500 cm$^2$, 10,000 cm$^2$, 1 m$^2$, 5 m$^2$, 10 m$^2$, 50 m$^2$, 100 m$^2$, 150 m$^2$, 200 m$^2$, 300 m$^2$, 400 m$^2$, 500 m$^2$, 600 m$^2$, 700 m$^2$, 800 m$^2$, 900 m$^2$, 1000 m$^2$. In some embodiments, a suitable filter may have a surface area of or greater than 264 m$^2$. In some embodiments, a suitable filter may have a surface area of or greater than 528 m$^2$. In some embodiments, a suitable filter may have a surface area of or greater than 1056 m$^2$. In some embodiments, a suitable filter may have a surface area of or greater than 2112 m$^2$. A single layer or multiple filtration layers may be used. Examples include diatomaceous earth matrices, cellulose matrices, or polypropylene felt matrices. In some embodiments, a suitable filter system includes depth filters that may be comprised of multiple layers of a single matrix type or multiple layers of different matrices. A suspension comprising precipitated mRNA flows through the depth filter by normal flow where precipitated mRNA is retained in the one or more filters having the suitable pore size. An exemplary array of depth array filters may include 2 or more, 3 or more, 4 or more, 5 or more, 6 or more, 7 or more, 8 or more, 9 or more, or 10 or more filter layers. In some embodiments, each layer has a pore size (e.g., measured by MWCO or average diameter) decreased by at least 10%, 20%, 30%, 40%, 50%, 60%, 70%, 80%, or 90% than that of the one preceding in the direction of the flow. As a non-limiting example, a suitable depth filters have the following pore sizes in order: 200 μm, 100 μm, 50 μm and 5 μm; or 500 μm, 300 μm, 200 μm, 100 μm, and 20 μm; or 100 μm, 50 μm, 20 μm, or 5 μm. An exemplary depth filter design is illustrated in FIG. 1.

Depth filters are commercially manufactured by several manufacturers, for example: Millipore Sigma (Clarisolve 60HX filters, Millistak filters), Pall Corporation, Sartorius Biotech, and others. The filters are prepared from inert materials, for example, felted polypropylene, or diatomaceous earth. The filter housings and adapter fittings comprise glass filled polypropylene. In some embodiments, the inert material is modified polyether sulfone (mPES). Other examples of inert material for filter include polyether sulfone (PES), polyvinylidene fluoride (PVDF) and cellulose. The filters may have varying thicknesses. The thickness of a filter may be 1 cm or greater. Depth filters offer easy scalability, for example, filters can be added to increase area of filtration. Exemplary filters with surface area and corresponding predicted mRNA purification capacities are as follows: 23 cm$^2$ filters may have a capacity of purifying about 290 mg mRNA; a 135 cm$^2$ filter may have a capacity of purifying about 1.7 gm mRNA; a 270 cm$^2$ filter have a capacity of purifying about 3.4 gm mRNA; 0.11-1.65 m$^2$ filters may have a capacity of purifying about 14 gm-200 gm mRNA; 11.5 m$^2$ filters may have a capacity of purifying about 1.4 Kg mRNA. In some embodiments, the filter comprises a total surface area of up to about 264 square meters or more, or up to about 528 square meters or more or up to about 1056 square meters or more.

Loading

Typically, the loading step involves loading a feed, such as a suspension containing precipitated mRNA, onto a filter system described herein. The feed may be loaded under various conditions, including but not limited to, constant flow, constant pressure, variable flow, variable pressure, and flow by wicking and/or gravity control. In some embodiments, a suspension containing precipitated mRNA from IVT reactions are loaded onto one or more filters with a suitable flow rate. Exemplary suitable concentration of a suspension containing precipitated mRNA may range from about 0.01 mg/ml to about 100 mg/ml, or from about 0.1 mg/ml to about 50 mg/ml, or from about 0.1 mg/ml to about 25 mg/ml, or from about 0.1 mg/ml to about 10 mg/ml, or from about 0.5 mg/ml to about 50 mg/ml, or from about 0.5 mg/ml to about 25 mg/ml, or from about 0.5 mg/ml to about 10 mg/ml, or from about 0.5 mg/ml to about 5 mg/ml, or from about 1 mg/ml to about 5 mg/ml. In some embodiments, suitable flow rate may be at least about 1 mg/ml, or 1.2 mg/ml, or 1.3 mg/ml, or 1.4 mg/ml, or 1.5 g/ml, or 1.6 mg/ml, or 1.7 mg/ml, or 1.8 mg/ml or 1.9 mg/ml or 2 mg/ml, and any concentration in between. In some embodiments, the flow rate of the suspension, normalized to the membrane area may range from 10 to 10000 Liters/m$^2$/hr (LMH). Exemplary suitable flow rates are 10 LMH, 50 LMH, 100 LMH, 200 LMH, 300 LMH, 400 LMH, 500 LMH, 600 LMH, 700 LMH, 800 LMH, 900 LMH, 1,000 LMH, 1,100 LMH, 1,200 LMH, 1,300 LMH, 1,400 LMH, 1,500 LMH, 1,600 LMH, 1,700 LMH, 1,800 LMH, 1,900 LMH, 2,000 LMH, 2,100 LMH, 2,200 LMH, 2,300 LMH, 2,400 LMH, 2,500 LMH, 2,600 LMH, 2,700 LMH, 2,800 LMH, 2,900 LMH, 3,000 LMH, 3,100 LMH, 3,200 LMH, 3,300 LMH, 3,400 LMH, 3,500 LMH, 3,600 LMH, 3,700 LMH, 3,800 LMH, 3,900 LMH, 4,000 LMH, 4,100 LMH, 4,200 LMH, 4,300 LMH, 4,400 LMH, 4,500 LMH, 4,600 LMH, 4,700 LMH, 4,800 LMH, 4,700 LMH, 4,800 LMH, 4,900 LMH, or 5,000 LMH. In some embodiments, the suitable flow rate includes 5,500 LMH, 6,000 LMH, 6,500 LMH, 7,000 LMH, 7,500 LMH, 8,000 LMH, 8,500 LMH, 9,000 LMH, 9,500 LMH, or 10,000 LMH.

In general, the flow rate may vary during loading. In some embodiments, the pressure is adjusted to maintain the flow rate with increase in loads. Exemplary loads flow times and rates are provided in the working examples provided in the specification.

Washing and Recovery of mRNA

The captured or retained insoluble precipitated mRNA may be washed before eluting to get rid of impurities retained on the filter(s). In some embodiments, a wash step comprises single rinse or multiple rinse cycles using one or more wash solutions. For example, a wash step may be carried out by multiple rinse cycles using a guanidinium buffer (GSCN) and ethanol, followed by 70-80% ethanol (e.g., about 70%, 75%, or 80% ethanol). In certain embodiments, multiple rinse cycles include more than 2, more than 3, more than 4, more than 5, more than 6, more than 7, more than 8, more than 9, or more than 10 cycles.

Various washing buffer may be used. For example, the captured mRNA may be subject to one or more salt washes and/or one or more ethanol washes. The washes may be performed using an aqueous solvent or an organic solvent. Exemplary washing buffers are further described in U.S. Pat. Nos. 9,957,499 and 9,850,269, and in U.S. patent application Ser. Nos. 15/907,086 and 15/906,864. In some embodiments, washing the precipitated mRNA can be achieved with one or more salt washes. In some embodiments, washing the precipitated mRNA can be achieved with an organic solvent. In some embodiments, washing the precipitated mRNA can be achieved with an ethanol wash.

Washing the precipitated mRNA can include use of an organic solvent such as ethanol. However, washing the precipitated mRNA can be achieved without the use organic solvent. In some embodiments, washing the precipitated mRNA can be achieved using PEG. In some embodiments, washing the precipitated mRNA can be achieved using PEG-6000. In some embodiments, washing the precipitated mRNA can be achieved using PEG-400. In some embodiments, washing the precipitated mRNA includes one or more washes comprising PEG having a viscosity of 90 centistrokes or less. In some embodiments, the PEG used to wash the precipitated mRNA has a viscosity of 80 centistrokes or less. In some embodiments, the PEG used to wash the precipitated mRNA has a viscosity of 70 centistrokes or less. In some embodiments, the PEG used to wash the precipitated mRNA has a viscosity of 60 centistrokes or less. In some embodiments, the PEG used to wash the precipitated mRNA has a viscosity of 50 centistrokes or less. In some embodiments, the PEG used to wash the precipitated mRNA has a viscosity of 40 centistrokes or less. In some embodiments, the PEG used to wash the precipitated mRNA has a viscosity of 30 centistrokes or less. In some embodiments, the PEG used to wash the precipitated mRNA has a viscosity of 20 centistrokes or less. In some embodiments, the PEG used to wash the precipitated mRNA has a viscosity of 10 centistrokes or less. In some embodiments, washing the precipitated mRNA can be achieved using triethylene glycol (TEG). In some embodiments, washing the precipitated mRNA can be achieved using triethylene glycol monomethyl ether (MTEG). In some embodiments, washing the precipitated mRNA can be achieved using tert-butyl-TEG-O-propionate. In some embodiments, washing the precipitated mRNA can be achieved using TEG-dimethacrylate. In some embodiments, washing the precipitated mRNA can be achieved using TEG-dimethyl ether. In some embodiments, washing the precipitated mRNA can be achieved using TEG-divinyl ether. In some embodiments, washing the precipitated mRNA can be achieved using TEG-monobutyl. In some embodiments, washing the precipitated mRNA can be achieved using TEG-methyl ether methacrylate. In some embodiments, washing the precipitated mRNA can be achieved using TEG-monodecyl ether. In some embodiments, washing the precipitated mRNA can be achieved using TEG-dibenzoate. The structures of each of these reagents are shown above in Table A.

Typically, captured or retained mRNA may be eluted by re-solubilizing the precipitated mRNA into a solution. For example, captured mRNA may be eluted with RNase-free water. In certain embodiments, eluting the captured mRNA involves recirculating the RNase-free water. For example, the RNase-free water may be circulated for about 5-100 minutes (e.g., about 5-90 minutes, about 5-80 minutes, about 5-70 minutes, about 5-60 minutes or about 5-30 minutes). In particular embodiments, the RNase-free water is re-circulated for about 5-10 minutes (e.g., for about 5, 6, 7, 8, 9 or 10 minutes).

In some embodiments, re-solubilized mRNA may be dialyzed into a desired formulation at a desired concentration. Various formulations may be used for dialysis. In some embodiments, the purified mRNA solution is dialyzed with 1 mM sodium citrate. In some embodiments, the purified mRNA solution is dialyzed with sodium acetate, ammonium carbonate, ammonium bicarbonate, pyridinium acetate, pyridinium formate, ammonium acetate, urea, potassium chloride, etc. Depending on the size of mRNA of interest, dialysis membranes with appropriate molecular weight cut-off (MWCO) may be used. For example, suitable dialysis membranes may have a MWCO of about 50 kDa, 60 kDa, 70 kDa, 80 kDa, 90 kDa, 100 kDa, 150 kDa, 200 kDa, 250 kDa, 300 kDa, 350 kDa, 400 kDa, 450 kDa, or 500 kDa.

Characterization of Purified mRNA

Purified mRNA may be characterized and quantified using any methods available in the art. In some embodiments, purified mRNA molecules are characterized using blotting, capillary electrophoresis, chromatography, fluorescence, gel electrophoresis, HPLC, silver stain, spectroscopy, ultraviolet (UV), or UPLC, or a combination thereof. Other methods known in the art are included in the present invention. In some embodiments, purified mRNA molecules are detected using UV absorption spectroscopy with separation by capillary electrophoresis. In some embodiments, mRNA is first denatured by a Glyoxal dye before gel electrophoresis ("Glyoxal gel electrophoresis").

In some embodiments, mRNA purified by methods disclosed herein comprises less than 10%, less than 9%, less than 8%, less than 7%, less than 6%, less than 5%, less than 4%, less than 3%, less than 2%, less than 1%, less than 0.5%, less than 0.1% impurities other than full-length mRNA determined by various detection methods described herein and known in the art (e.g., capillary electrophoresis, gel electrophoresis, HPLC, or UPLC). The impurities include IVT contaminants, e.g., proteins, enzymes, free nucleotides and/or shortmers. As used herein, the term "shortmers" or "abortive transcripts" refers to any transcripts that are less than full-length. In some embodiments, "shortmers" or "abortive transcripts" are less than 100 nucleotides in length, less than 90, less than 80, less than 70, less than 60, less than 50, less than 40, less than 30, less than 20, or less than 10 nucleotides in length. In some embodiments, shortmers are detected or quantified after adding a 5'-cap, and/or a 3'-poly A tail.

Among other things, the purification methods described herein may be used to manufacture mRNA for therapeutic use. The purity and/or integrity of purified mRNA determined by various characterization techniques described herein may be used as batch release criteria. In some embodiments, the release criteria of a batch production of mRNA in a manufacturing process includes capillary electrophoretic determination of one or more of the following: the purified mRNA comprises 5% or less, 4% or less, 3% or less, 2% or less, 1% or less, or substantially free of protein contaminants; the purified mRNA comprises 5%, or less, 4% or less, 3% or less, 2% or less, 1% or less, or substantially free of short abortive RNA contaminants; the purified mRNA comprises 5% or less, 4% or less, 3% or less, 2% or less, 1% or less, or substantially free of salt contaminants; the purified mRNA comprises 95% or greater, 96% or greater, 97% or greater, 98% or greater or 99% or greater integrity.

In some embodiments, the release criteria of a batch production of mRNA in a manufacturing process includes HPLC determination of one or more of the following: the purified mRNA comprises 5% or less, 4% or less, 3% or less, 2% or less, 1% or less, or substantially free of protein contaminants; the purified mRNA comprises 5% or less, 4% or less, 3% or less, 2% or less, 1% or less, or substantially free of short abortive RNA contaminants; the purified mRNA comprises 5% or less, 4% or less, 3% or less, 2% or less, 1% or less, or substantially free of salt contaminants; the purified mRNA comprises 95% or greater, 96% or greater, 97% or greater, 98% or greater or 99% or greater integrity.

Additionally, mRNA purified according to the present invention results in a high yield. For example, the total purified mRNA is recovered in an amount that results in a yield of at least about 70%, 75%, 85%, 90%, 91%, 92%, 93%, 94%, 95%, 96%, 97%, 98% or 99%.

According to the present invention, mRNA may be purified in a large scale. For example, at least 0.5 grams, 1 gram, 5 grams, 10 grams, 15 grams, 20 grams, 35 grams, 40 grams, 45 grams, 50 grams, 60 grams, 70 grams, 80 grams, 90 grams, 100 grams, 200 grams, 300 grams, 400 grams, 500 grams, 1 kilogram, 10 kilograms, 50 kilograms, 100 kilograms of mRNA may be purified in a single batch.

Compositions and Methods of Treatment mRNA purified according to the present invention may be delivered as naked mRNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

According to various embodiments, suitable delivery vehicles include, but are not limited to polymer based carriers, such as polyethyleneimine (PEI), lipid nanoparticles (LNPs) and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g., a lipid nanoparticle (LNP) or liposome. In some embodiments, liposomes may comprise one or more cationic lipids. In some embodiments, a liposome comprises one or more cationic lipids, one or more non-cationic lipids, one or more cholesterol-based lipids and one or more PEG-modified lipids. In some embodiments, a liposome comprises one or more cationic lipids, one or more non-cationic lipids, and one or more PEG-modified lipids. In some embodiments, a liposome comprises no more than four distinct lipid components. In some embodiments, a liposome comprises no more than three distinct lipid components. In some embodiments, one distinct lipid component is a sterol-based cationic lipid.

As used herein, the term "cationic lipids" refers to any of a number of lipid and lipidoid species that have a net positive charge at a selected pH, such as at physiological pH. Several cationic lipids have been described in the literature, many of which are commercially available.

Accordingly, in certain embodiments the present invention provides a method for producing a therapeutic composition comprising purified mRNA that encodes a peptide or polypeptide for use in the delivery to or treatment of the lung of a subject or a lung cell. In certain embodiments the present invention provides a method for producing a therapeutic composition comprising purified mRNA that encodes an endogenous protein which may be deficient or non-functional in a subject. In certain embodiments the present invention provides a method for producing a therapeutic composition comprising purified mRNA that encodes an endogenous protein which may be deficient or non-functional in a subject.

In certain embodiments the present invention provides a method for producing a therapeutic composition comprising purified mRNA that encodes a peptide or polypeptide for use in the delivery to or treatment of the lung of a subject or a lung cell. In certain embodiments the present invention is useful in a method for manufacturing mRNA encoding cystic fibrosis transmembrane conductance regulator, CFTR. The CFTR mRNA is delivered to the lung of a subject in need in a therapeutic composition for treating cystic fibrosis. In certain embodiments the present invention provides a method for producing a therapeutic composition comprising purified mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides therapeutic benefit.

In certain embodiments the present invention provides a method for producing a therapeutic composition comprising purified mRNA that encodes for a protein associated with a urea cycle disorder. In certain embodiments the present invention provides a method for producing a therapeutic composition comprising purified mRNA that encodes for ornithine transcarbamylase (OTC) protein. In certain embodiments the present invention provides a method for producing a therapeutic composition comprising purified mRNA that encodes for arginosuccinate synthetase 1 protein. In certain embodiments the present invention provides a method for producing a therapeutic composition comprising purified mRNA that encodes for carbamoyl phosphate synthetase I protein. In certain embodiments the present invention provides a method for producing a therapeutic composition comprising purified mRNA that encodes for arginosuccinate lyase protein. In certain embodiments the present invention provides a method for producing a therapeutic composition comprising purified mRNA that encodes for arginase protein.

In certain embodiments the present invention provides a method for producing a therapeutic composition comprising purified mRNA that encodes for a protein associated with a lysosomal storage disorder. In certain embodiments the present invention provides a method for producing a therapeutic composition comprising purified mRNA that encodes for alpha galactosidase protein. In certain embodiments the present invention provides a method for producing a therapeutic composition comprising purified mRNA that encodes for glucocerebrosidase protein. In certain embodiments the present invention provides a method for producing a therapeutic composition comprising purified mRNA that encodes for iduronate-2-sulfatase protein. In certain embodiments the present invention provides a method for producing a therapeutic composition comprising purified mRNA that encodes for iduronidase protein. In certain embodiments the present invention provides a method for producing a therapeutic composition comprising purified mRNA that encodes for N-acetyl-alpha-D-glucosaminidase protein. In certain embodiments the present invention provides a method for producing a therapeutic composition comprising purified mRNA that encodes for heparan N-sulfatase protein. In certain embodiments the present invention provides a method for producing a therapeutic composition comprising purified mRNA that encodes for galactosamine-6 sulfatase protein. In certain embodiments the present invention provides a method for producing a therapeutic composition comprising purified mRNA that encodes for beta-galactosidase protein. In certain embodiments the present invention provides a method for producing a therapeutic composition comprising purified mRNA that encodes for lysosomal lipase protein. In certain embodiments the present invention provides a method for producing a therapeutic composition comprising purified mRNA that encodes for arylsulfatase B (N-acetylgalactosamine-4-sulfatase) protein. In certain embodiments the present invention provides a method for producing a therapeutic composition comprising purified mRNA that encodes for transcription factor EB (TFEB).

In certain embodiments the present invention provides a method for producing a therapeutic composition comprising purified mRNA that encodes for a protein associated with a glycogen storage disorder. In certain embodiments the present invention provides a method for producing a therapeutic composition comprising purified mRNA that encodes for acid alpha-glucosidase protein. In certain embodiments the present invention provides a method for producing a therapeutic composition comprising purified mRNA that encodes for glucose-6-phosphatase (G6PC) protein. In certain embodiments the present invention provides a method for producing a therapeutic composition comprising purified mRNA that encodes for liver glycogen phosphorylase protein. In certain embodiments the present invention provides a method for producing a therapeutic composition comprising purified mRNA that encodes for muscle phosphoglycerate mutase protein. In certain embodiments the present invention provides a method for producing a therapeutic composition comprising purified mRNA that encodes for glycogen debranching enzyme.

In certain embodiments the present invention provides a method for producing a therapeutic composition comprising purified mRNA that encodes for a protein associated with amino acid metabolism. In certain embodiments the present invention provides a method for producing a therapeutic composition comprising purified mRNA that encodes for phenylalanine hydroxylase enzyme. In certain embodiments the present invention provides a method for producing a therapeutic composition comprising purified mRNA that encodes for glutaryl-CoA dehydrogenase enzyme. In certain embodiments the present invention provides a method for producing a therapeutic composition comprising purified mRNA that encodes for propionyl-CoA caboxylase enzyme. In certain embodiments the present invention provides a method for producing a therapeutic composition comprising purified mRNA that encodes for oxalase alanine-glyoxylate aminotransferase enzyme.

In certain embodiments the present invention provides a method for producing a therapeutic composition comprising purified mRNA that encodes for a protein associated with a lipid metabolism or fibrotic disorder. In certain embodiments the present invention provides a method for producing a therapeutic composition comprising purified mRNA that encodes for an mTOR inhibitor. In certain embodiments the present invention provides a method for producing a therapeutic composition comprising purified mRNA that encodes for ATPase phospholipid transporting 8B1 (ATP8B1) protein. In certain embodiments the present invention provides a method for producing a therapeutic composition comprising purified mRNA that encodes for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition comprising purified mRNA that encodes for PPAR-gamma protein or an active variant.

In certain embodiments the present invention provides a method for producing a therapeutic composition comprising purified mRNA that encodes for a protein associated with methylmalonic acidemia. For example, in certain embodiments the present invention provides a method for producing a therapeutic composition comprising purified mRNA that encodes for methylmalonyl CoA mutase protein. In certain embodiments the present invention provides a method for producing a therapeutic composition comprising purified mRNA that encodes for methylmalonyl CoA epimerase protein.

In certain embodiments the present invention provides a method for producing a therapeutic composition comprising purified mRNA for which delivery to or treatment of the liver can provide therapeutic benefit. In certain embodiments the present invention provides a method for producing a therapeutic composition comprising purified mRNA that encodes for ATP7B protein, also known as Wilson disease protein. In certain embodiments the present invention provides a method for producing a therapeutic composition comprising purified mRNA that encodes for porphobilinogen deaminase enzyme. In certain embodiments the present invention provides a method for producing a therapeutic composition comprising purified mRNA that encodes for one or clotting enzymes, such as Factor VIII, Factor IX, Factor VII, and Factor X. In certain embodiments the present invention provides a method for producing a therapeutic composition comprising purified mRNA that encodes for human hemochromatosis (HFE) protein.

In certain embodiments the present invention provides a method for producing a therapeutic composition comprising purified mRNA that encodes a peptide or polypeptide for use in the delivery to or treatment of the cardiovasculature of a subject or a cardiovascular cell. In certain embodiments the present invention provides a method for producing a therapeutic composition comprising purified mRNA that encodes for vascular endothelial growth factor A protein. In certain embodiments the present invention provides a method for producing a therapeutic composition comprising purified mRNA that encodes for relaxin protein. In certain embodiments the present invention provides a method for producing a therapeutic composition comprising purified mRNA that encodes for bone morphogenetic protein-9 protein. In certain embodiments the present invention provides a method for producing a therapeutic composition comprising purified mRNA that encodes for bone morphogenetic protein-2 receptor protein.

In certain embodiments the present invention provides a method for producing a therapeutic composition comprising purified mRNA that encodes a peptide or polypeptide for use in the delivery to or treatment of the muscle of a subject or a muscle cell. In certain embodiments the present invention provides a method for producing a therapeutic composition comprising purified mRNA that encodes for dystrophin protein. In certain embodiments the present invention provides a method for producing a therapeutic composition comprising purified mRNA that encodes for frataxin protein. In certain embodiments the present invention provides a method for producing a therapeutic composition comprising purified mRNA that encodes a peptide or polypeptide for use in the delivery to or treatment of the cardiac muscle of a subject or a cardiac muscle cell. In certain embodiments the present invention provides a method for producing a therapeutic composition comprising purified mRNA that encodes for a protein that modulates one or both of a potassium channel and a sodium channel in muscle tissue or in a muscle cell. In certain embodiments the present invention provides a method for producing a therapeutic composition comprising purified mRNA that encodes for a protein that modulates a Kv7.1 channel in muscle tissue or in a muscle cell. In certain embodiments the present invention provides a method for producing a therapeutic composition comprising purified mRNA that encodes for a protein that modulates a Nav1.5 channel in muscle tissue or in a muscle cell.

In certain embodiments the present invention provides a method for producing a therapeutic composition comprising purified mRNA that encodes a peptide or polypeptide for use in the delivery to or treatment of the nervous system of a subject or a nervous system cell. For example, in certain embodiments the present invention provides a method for producing a therapeutic composition comprising purified mRNA that encodes for survival motor neuron 1 protein. For example, in certain embodiments the present invention provides a method for producing a therapeutic composition comprising purified mRNA that encodes for survival motor neuron 2 protein. In certain embodiments the present invention provides a method for producing a therapeutic composition comprising purified mRNA that encodes for frataxin protein. In certain embodiments the present invention provides a method for producing a therapeutic composition comprising purified mRNA that encodes for ATP binding cassette subfamily D member 1 (ABCD1) protein. In certain embodiments the present invention provides a method for producing a therapeutic composition comprising purified mRNA that encodes for CLN3 protein.

In certain embodiments the present invention provides a method for producing a therapeutic composition comprising purified mRNA that encodes a peptide or polypeptide for use in the delivery to or treatment of the blood or bone marrow of a subject or a blood or bone marrow cell. In certain embodiments the present invention provides a method for producing a therapeutic composition comprising purified mRNA that encodes for beta globin protein. In certain embodiments the present invention provides a method for producing a therapeutic composition comprising purified mRNA that encodes for Bruton's tyrosine kinase protein. In certain embodiments the present invention provides a method for producing a therapeutic composition comprising purified mRNA that encodes for one or clotting enzymes, such as Factor VIII, Factor IX, Factor VII, and Factor X.

In certain embodiments the present invention provides a method for producing a therapeutic composition comprising purified mRNA that encodes a peptide or polypeptide for use in the delivery to or treatment of the kidney of a subject or a kidney cell. In certain embodiments the present invention provides a method for producing a therapeutic composition comprising purified mRNA that encodes for collagen type IV alpha 5 chain (COL4A5) protein.

In certain embodiments the present invention provides a method for producing a therapeutic composition comprising purified mRNA that encodes a peptide or polypeptide for use in the delivery to or treatment of the eye of a subject or an eye cell. In certain embodiments the present invention provides a method for producing a therapeutic composition comprising purified mRNA that encodes for ATP-binding cassette sub-family A member 4 (ABCA4) protein. In certain embodiments the present invention provides a method for producing a therapeutic composition comprising purified mRNA that encodes for retinoschisin protein. In certain embodiments the present invention provides a method for producing a therapeutic composition comprising purified mRNA that encodes for retinal pigment epithelium-specific 65 kDa (RPE65) protein. In certain embodiments the present invention provides a method for producing a therapeutic composition comprising purified mRNA that encodes for centrosomal protein of 290 kDa (CEP290).

In certain embodiments the present invention provides a method for producing a therapeutic composition comprising purified mRNA that encodes a peptide or polypeptide for use in the delivery of or treatment with a vaccine for a subject or a cell of a subject. For example, in certain embodiments the present invention provides a method for producing a therapeutic composition comprising purified mRNA that encodes for an antigen from an infectious agent, such as a virus. In certain embodiments the present invention provides a method for producing a therapeutic composition comprising purified mRNA that encodes for an antigen from influenza virus. In certain embodiments the present invention provides a method for producing a therapeutic composition comprising purified mRNA that encodes for an antigen from respiratory syncytial virus. In certain embodiments the present invention provides a method for producing a therapeutic composition comprising purified mRNA that encodes for an antigen from rabies virus. In certain embodiments the present invention provides a method for producing a therapeutic composition comprising purified mRNA that encodes for an antigen from cytomegalovirus. In certain embodiments the present invention provides a method for producing a therapeutic composition comprising purified mRNA that encodes for an antigen from rotavirus. In certain embodiments the present invention provides a method for producing a therapeutic composition comprising purified mRNA that encodes for an antigen from a hepatitis virus, such as hepatitis A virus, hepatitis B virus, or hepatis C virus. In certain embodiments the present invention provides a method for producing a therapeutic composition comprising purified mRNA that encodes for an antigen from human papillomavirus. In certain embodiments the present invention provides a method for producing a therapeutic composition comprising purified mRNA that encodes for an antigen from a herpes simplex virus, such as herpes simplex virus 1 or herpes simplex virus 2. In certain embodiments the present invention provides a method for producing a therapeutic composition comprising purified mRNA that encodes for an antigen from a human immunodeficiency virus, such as human immunodeficiency virus type 1 or human immunodeficiency virus type 2. In certain embodiments the present invention provides a method for producing a therapeutic composition comprising purified mRNA that encodes for an antigen from a human metapneumovirus. In certain embodiments the present invention provides a method for producing a therapeutic composition comprising purified mRNA that encodes for an antigen from a human parainfluenza virus, such as human parainfluenza virus type 1, human parainfluenza virus type 2, or human parainfluenza virus type 3. In certain embodiments the present invention provides a method for producing a therapeutic composition comprising purified mRNA that encodes for an antigen from malaria virus. In certain embodiments the present invention provides a method for producing a therapeutic composition comprising purified mRNA that encodes for an antigen from zika virus. In certain embodiments the present invention provides a method for producing a therapeutic composition comprising purified mRNA that encodes for an antigen from chikungunya virus.

In certain embodiments the present invention provides a method for producing a therapeutic composition comprising purified mRNA that encodes for an antigen associated with a cancer of a subject or identified from a cancer cell of a subject. In certain embodiments the present invention provides a method for producing a therapeutic composition comprising purified mRNA that encodes for an antigen determined from a subject's own cancer cell, i.e., to provide a personalized cancer vaccine. In certain embodiments the present invention provides a method for producing a therapeutic composition comprising purified mRNA that encodes for an antigen expressed from a mutant KRAS gene.

In certain embodiments the present invention provides a method for producing a therapeutic composition comprising purified mRNA that encodes for an antibody. In certain embodiments, the antibody can be a bi-specific antibody. In certain embodiments, the antibody can be part of a fusion protein. In certain embodiments the present invention provides a method for producing a therapeutic composition comprising purified mRNA that encodes for an antibody to OX40. In certain embodiments the present invention provides a method for producing a therapeutic composition comprising purified mRNA that encodes for an antibody to VEGF. In certain embodiments the present invention provides a method for producing a therapeutic composition comprising purified mRNA that encodes for an antibody to tissue necrosis factor alpha. In certain embodiments the present invention provides a method for producing a therapeutic composition comprising purified mRNA that encodes for an antibody to CD3. In certain embodiments the present invention provides a method for producing a therapeutic composition comprising purified mRNA that encodes for an antibody to CD19.

In certain embodiments the present invention provides a method for producing a therapeutic composition comprising purified mRNA that encodes for an immunomodulator. In certain embodiments the present invention provides a method for producing a therapeutic composition comprising purified mRNA that encodes for Interleukin 12. In certain embodiments the present invention provides a method for producing a therapeutic composition comprising purified mRNA that encodes for Interleukin 23. In certain embodiments the present invention provides a method for producing a therapeutic composition comprising purified mRNA that encodes for Interleukin 36 gamma. In certain embodiments the present invention provides a method for producing a therapeutic composition comprising purified mRNA that encodes for a constitutively active variant of one or more stimulator of interferon genes (STING) proteins.

In certain embodiments the present invention provides a method for producing a therapeutic composition comprising purified mRNA that encodes for an endonuclease. In certain embodiments the present invention provides a method for producing a therapeutic composition comprising purified mRNA that encodes for an RNA-guided DNA endonuclease protein, such as Cas 9 protein. In certain embodiments the present invention provides a method for producing a therapeutic composition comprising purified mRNA that encodes for a meganuclease protein. In certain embodiments the present invention provides a method for producing a therapeutic composition comprising purified mRNA that encodes for a transcription activator-like effector nuclease protein. In certain embodiments the present invention provides a method for producing a therapeutic composition comprising purified mRNA that encodes for a zinc finger nuclease protein.

In certain embodiments the present invention provides a method for producing a therapeutic composition comprising purified mRNA that encodes for treating an ocular disease. In some embodiments the method is used for producing a therapeutic composition comprising purified mRNA encoding retinoschisin.

Another aspect of the present invention is a purified mRNA composition prepared by an above-described aspect or embodiment.

Yet another aspect of the present invention is pharmaceutical composition including the purified mRNA composition of the above aspect and at least one pharmaceutically-acceptable excipient.

An aspect of the present invention is a method for treating a disease or disorder including a step of administering to a subject in need thereof the pharmaceutical composition of the above aspect.

Another aspect of the present invention is a solution including purified mRNA prepared by an above-described aspect or embodiment.

In some embodiments the present invention provides a pharmaceutical composition including the solution including purified mRNA of the above description and at least one pharmaceutically-acceptable excipient.

An aspect of the present invention is a method for treating a disease or disorder including a step of administering to a subject in need thereof the pharmaceutical composition of the above aspect.

The present invention further includes a composition including a purified mRNA precipitate produced by an above aspect and/or embodiment.

The present invention further includes a pharmaceutical composition including a purified mRNA precipitate produced by an above aspect and/or embodiment and at least one pharmaceutically-acceptable excipient.

The present invention further includes a method for treating a disease or disorder comprising administering to a subject in need thereof a pharmaceutical composition of the above aspect and/or embodiment.

Any aspect or embodiment described herein can be combined with any other aspect or embodiment as disclosed herein. While the disclosure has been described in conjunction with the detailed description thereof, the above description is intended to illustrate and not limit the scope of the disclosure, which is defined by the scope of the appended claims. Other aspects, advantages, and modifications are within the scope of the following claims.

Additional teaching relevant to the present invention are described in one or more of the following: WO 2010/053572; WO 2011/068810; WO 2012/075040; WO 2012/170889; WO 2012/170930; WO 2013/063468; WO 2013/149140; WO 2013/149141; WO 2013/185067; WO 2013/185069; WO 2014/089486; WO 2014/152513; WO 2014/152659; WO 2014/152673; WO 2014/152774; WO 2014/152966; WO 2014/153052; WO 2015/061461; WO 2015/061467; WO 2015/061491; WO 2015/061500; WO 2015/148247; WO 2015/164773; WO 2015/184256; WO 2015/200465; WO 2016/004318; WO 2016/149508; WO/2014/152940; PCT/US16/57044; U.S. 62/320,073; U.S. 62/349,331; U.S. 62/420,413; U.S. 62/420,421; U.S. 62/420,428; U.S. 62/420,435; U.S. 62/421,007; U.S. 62/421,021, and the related applications filed Feb. 27, 2017 by Applicant entitled "LARGE SCALE SYNTHESIS OF MESSENGER RNA" (U.S. 62/464,043), "METHODS FOR PURIFICATION OF MESSENGER RNA" (U.S. 62/463,998), and "NOVEL CODON-OPTIMIZED CFTR MRNA" (U.S. 62/464,215), each of which is incorporated by reference in its entirety.

Although methods and materials similar or equivalent to those described herein can be used in the practice or testing of the present invention, suitable methods and materials are described below. All publications, patent applications, patents, and other references mentioned herein are incorporated by reference in their entirety. The references cited herein are not admitted to be prior art to the claimed invention. In addition, the materials, methods, and examples are illustrative only and are not intended to be limiting.

EXAMPLES

Example 1: Normal Flow Filtration Purification of mRNA

In this experiment, the feasibility of normal flow filtration using depth filtration (Clarisolve 60HX) for purification of messenger RNA (mRNA) was evaluated. The method steps included (1) precipitating of mRNA, (2) capturing by a filter the precipitated mRNA within and/or on the filter, (3) washing the captured precipitated mRNA, (4) dissolving the precipitated mRNA to transform it into a filter permeate, and (5) recovery of the dissolved. In particular, in this experiment, precipitation conditions and wash buffers were varied and yield and purity of the mRNA were evaluated. Feasibility of this normal flow filtration was assessed at various points in the purification: (i) retention of precipitated mRNA within the depth filter as indicated by visual inspection of filtrate; (ii) effectiveness of the precipitated mRNA wash as indicated by filtrate conductivity; (iii) recovery of mRNA from the purification as indicated by spectrophotometry.

IVT Reaction

For this and all examples described herein, in general, mRNA was in vitro transcribed (IVT) by standard methods. Briefly, for each gram of mRNA transcribed, a reaction containing linearized double stranded DNA plasmid with an RNA polymerase-specific promoter, RNA polymerase (e.g., SP6 polymerase or T7 polymerase), RNase inhibitor, pyrophosphatase, NTPs, DTT and a reaction buffer was prepared with RNase-free water then incubated at 37° C. for a specified time. The reaction was then quenched by the addition of DNase I and a DNase I buffer to facilitate digestion of the double-stranded DNA template in preparation for purification.

RNA Precipitation and Filtration

Materials: Feed mRNA: In vitro synthesized mRNA encoding CFTR; GSCN Buffer: A mixture of Guanidine Thiocyanate, Sodium Citrate, N-Lauryl Sarcosine; Depth Filter: Clarisolve 60HX, Cat No: CS60HX01L3, having effective area 23 cm². GSCN Wash Buffer: GSCN Buffer, Ethanol, water.

A. Precipitation

In vitro synthesized mRNA encoding CFTR (Feed mRNA) was precipitated by first mixing the mRNA with Guanidinium thio-cyanide (GSCN) buffer and mixed to denature the mRNA. 100% Ethanol (EtOH) was added to the mixture and mixed to precipitate the mRNA.

B. Filtration

The precipitated mixture was loaded onto the depth filter at constant feed flux. The initial feed flux was selected to achieve a process time of 3-4 hours. The flux was adjusted during the experiment. After completion of the loading, the captured, precipitated mRNA was rinsed (washed) with GSCN/Ethanol Wash Buffer followed by 80% ethanol until a filtrate conductivity of 0.0 mS/cm was achieved. Filtrate mass, feed pressure, and filtrate conductivity were monitored during the loading and washing steps. The washed, precipitated mRNA was dissolved and transformed into filtrate by altering the rinse from 80% ethanol to water. In this instance, the water was recirculated through the depth filter and filter system. Then the water with dissolved mRNA was collected and the mRNA recovery was measured via absorbance at 260 nm.

mRNA Analysis: In this and other examples described herein, change in resistance during mRNA loading to filter was recorded with increasing load and was measured as feed pressure divided by feed flux. This parameter was indicated instead of indicating pressure to normalize pressure changes resulting from flow rate changes. mRNA integrity (which can include capped and tailed (C/T) mRNA, where integrity includes assessment of poly-A tail length) was analyzed using the CE Fragment Analyzer™ with standard sensitivity mRNA analysis kit (Advanced Analytical Tech.) with a total mRNA load of 300 ng. Residual process enzymes were analyzed by preparing 20 µg of RNase I digested mRNA in NuPAGE sample loading and reducing buffer, separating samples on a NuPage 10% bis-tris gel at 200V for 35 minutes (Invitrogen). Then residual proteins were visualized using the SilverQuest™ silver stain kit (Invitrogen). The starting mass of an mRNA to be purified was calculated based on the theoretically expected amount of product as determined by initial reagent amounts in an IVT and/or a cap/tail reaction used to prepare the mRNA. The percent yield was calculated as the ratio of the obtained product to the theoretically expected amount of product.

Figure 2:
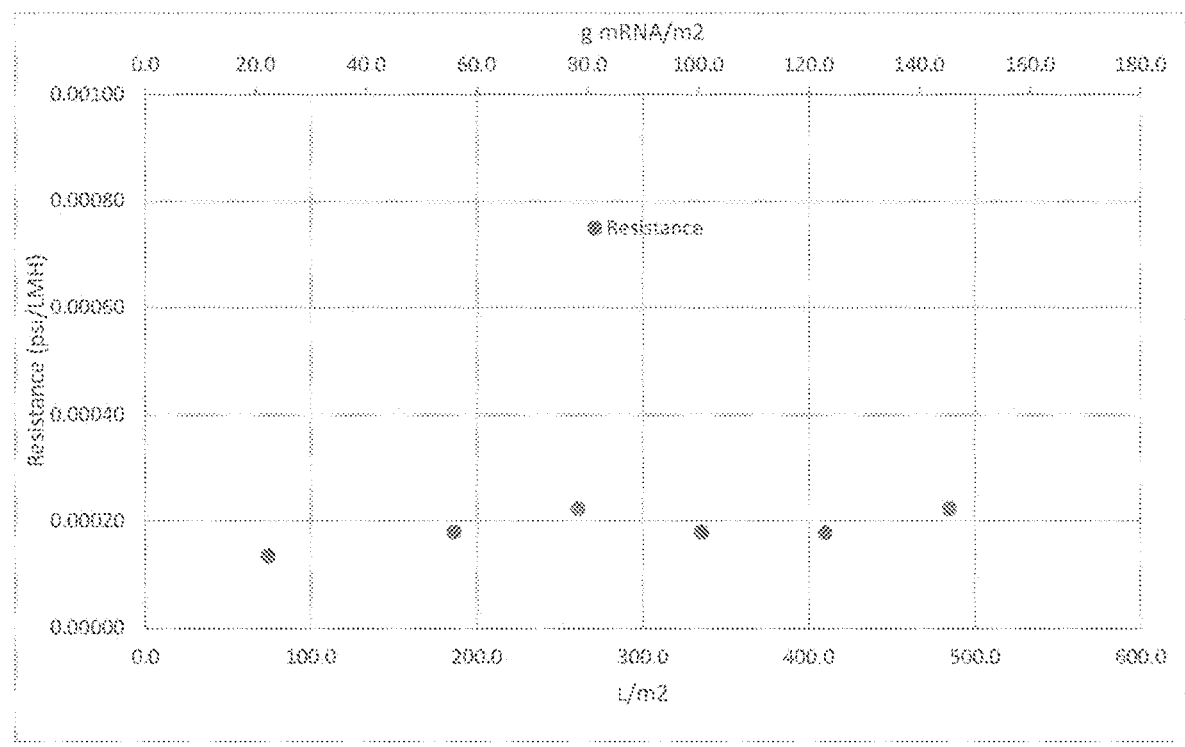
FIG. 2 demonstrates change in filter resistance with respect to the amount of CFTR-encoding mRNA loaded onto the filter in an exemplary mRNA purification study using a depth filter.

No increase in resistance was observed with increasing mRNA load during the loading step. The trend of resistance vs. mRNA loading is shown in FIG. 2. Resistance was calculated as the feed pressure divided by feed flux.

The filtrate from the load and washing steps was inspected for the presence of precipitate as an indication of some portion of the precipitated mRNA passing through the filter. No precipitates were observed in the filtrate.

Figure 3:
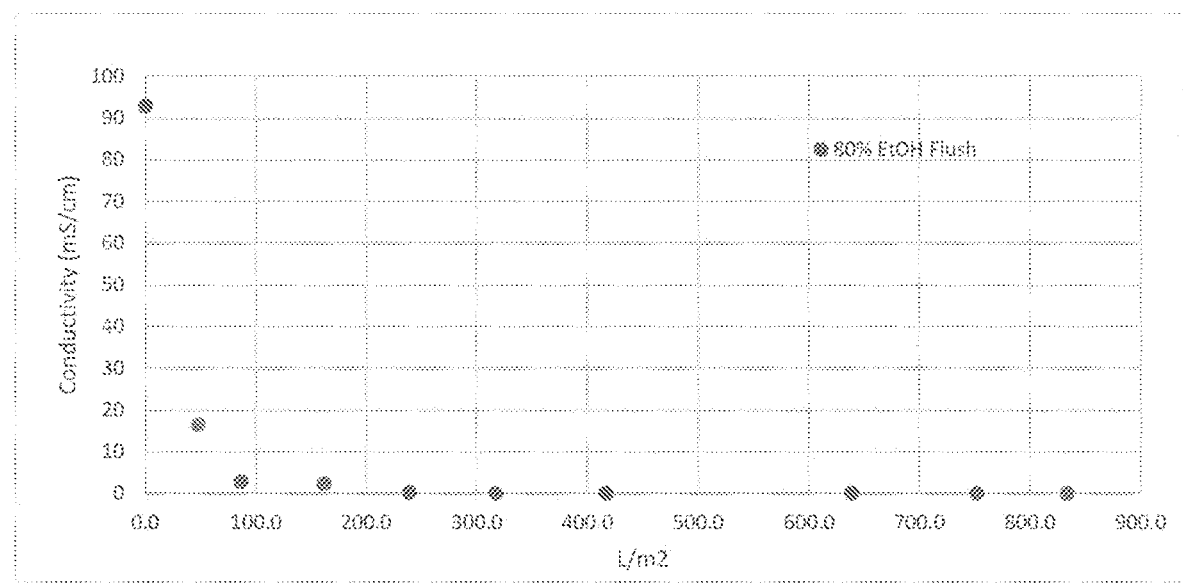
FIG. 3 shows a change in filter conductivity with increasing Ethanol Flush Volume indicating the effectiveness of the flush volume in removing salt from the precipitated mRNA.

As noted above, the precipitated mRNA in the filter was washed with GSCN/Ethanol Wash Buffer followed by 80% EtOH. The effectiveness of this filter system to remove manufacturing salt contaminants was demonstrated by measuring the conductivity and plotting it against increasing volume of the EtOH wash buffer and is shown in FIG. 3. The conductivity conferred by the contaminant salts decreased to zero with the increasing flush volume, thereby indicating removal of the salts and showing that 80% Ethanol effectively removed salt contaminants from the filter and precipitated mRNA. In particular, filtrate conductivity of 0.0 mS/cm was observed after a flush volume of approximately 2.0 L per gram of mRNA.

Figure 4:
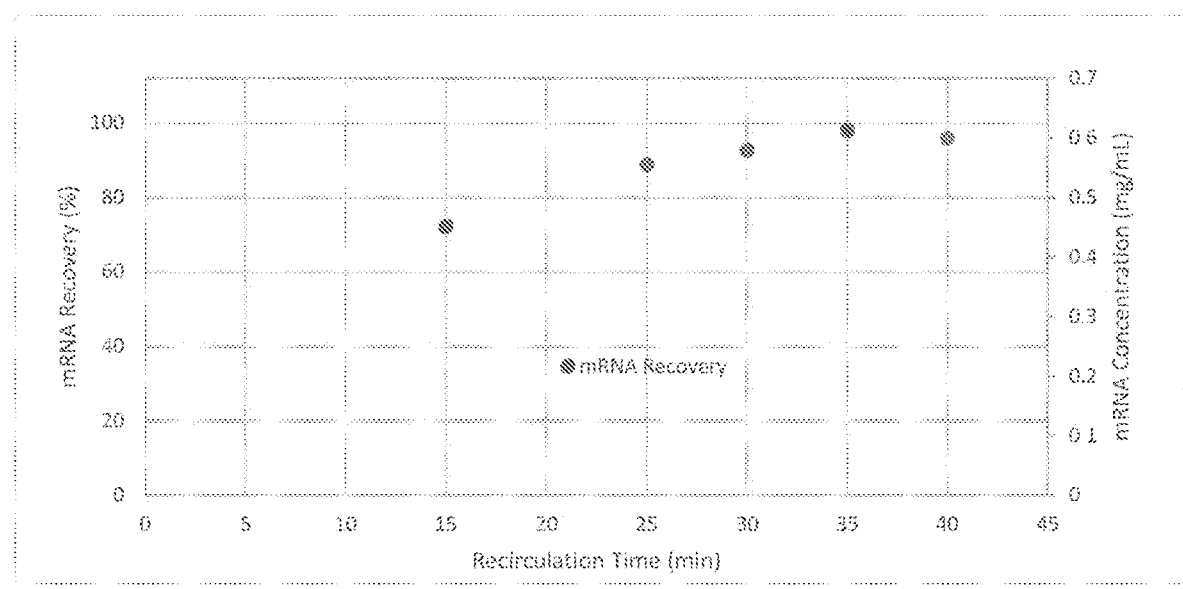
FIG. 4 demonstrates percent mRNA recovery of in vitro transcribed CFTR mRNA over recirculation time.

The mRNA recovery from this purification method is summarized in Table 1. FIG. 4 shows percent mRNA recovery of in vitro transcribed CFTR mRNA over recirculation time. After 40 minutes of recirculating water through the system to dissolve the precipitated mRNA, filtrate was collected, and mRNA was measured via absorbance at A260. Surprisingly, 94% of the mRNA was recovered from this purification. This surprisingly high recovery percentage from resulting conductivity measure of zero indicated that (a) the precipitated mRNA was successfully captured/retained within the depth filter media, (b) precipitated mRNA captured in the depth filter media was effectively washed of salt contaminants and (c) precipitated mRNA captured in the depth filter media was effectively recovered.

TABLE 1

| Summary of Product Recovery | |
| --- | --- |
| Starting Mass | 373 mg |
| Recovered Mass: | 352 mg |
| % Recovery: | 94% |

As shown in Table 1, a high recovery was obtained using the normal flow filtration process described herein.

Example 2. Normal Flow Filter Purification of mRNA after the Capping and Tailing Reaction In this experiment, normal flow filter purification was performed using a depth filter on IVT manufactured mRNA after the capping and tailing (C/T) reaction. The purification of the capped and tailed mRNA was evaluated using the following criteria: (i) retention of precipitated mRNA post C/T reaction within depth filter (the Clarisolve 60HX) as indicated by visual inspection of filtrate and product recovery; (ii) effectiveness of the precipitated mRNA wash to remove contaminants and retain mRNA, as indicated by filtrate conductivity and product recovery; (iii) recovery of mRNA (following dissolution of it in precipitated form, thereby transforming the mRNA captured in and/or on the filter to filter filtrate) as indicated by spectrophotometry; (iv) mRNA integrity as indicated by capillary electrophoresis (CE); and (v) mRNA purity as indicated by silver stain gel analysis.

Capping and Tailing (C/T) Reaction

Following synthesis of mRNA by in vitro transcription as described above, the in vitro transcribed mRNA was modified enzymatically by the addition of a 5' $N^7$-methylguanylate Cap 0 structure using guanylate transferase and the addition of a methyl group at the 2' O position of the penultimate nucleotide resulting in a Cap 1 structure using 2' O-methyltransferase as described by Fechter, P.; Brownlee, G. G. "Recognition of mRNA cap structures by viral and cellular proteins" *J. Gen. Virology* 2005, 86, 1239-1249. Following addition of the Cap 1 structure, a poly-adenylate tail was added to the 3' end of the in vitro transcribed mRNA enzymatically using poly-A polymerase.

The C/T reaction was performed immediately prior to the precipitation and depth filter testing.

A. Precipitation

The C/T material was precipitated without dilution (Precipitation 1). The precipitation was performed by first mixing the mRNA feed material with GSCN buffer (and mixed for 14 minutes to denature the mRNA. 100% Ethanol was added to the mixture and mixed for 6 minutes to precipitate the mRNA.

B. Filtration

The resulting solution comprising precipitated mRNA was loaded onto the depth filter at constant feed flux of approximately 1600LMH (based on previous testing and process time considerations). After completion of the loading, the captured precipitate was rinsed (washed) with GSCN/Ethanol Wash Buffer (as described above) followed by 80% Ethanol washing until a filtrate conductivity of 0.0 mS/cm was achieved. Filtrate mass, feed pressure, and filtrate conductivity were monitored during the loading and washing steps. The washed, precipitated mRNA in the depth filter was dissolved by recirculating water through the depth filter, thereby transforming the captured mRNA to filtrate. The dissolved mRNA then was recovered as filtrate and the recovery was measured over time via absorbance at 260 nm.

A second precipitation (Precipitation 2) also was performed on the mRNA eluted from the depth filter. This second precipitation was performed using the same procedure used for the first precipitation. The precipitated mRNA captured by the filter was subjected to a second round of washing, followed by dissolution and collection as filtrate, following the same procedure described above.

Figure 5:
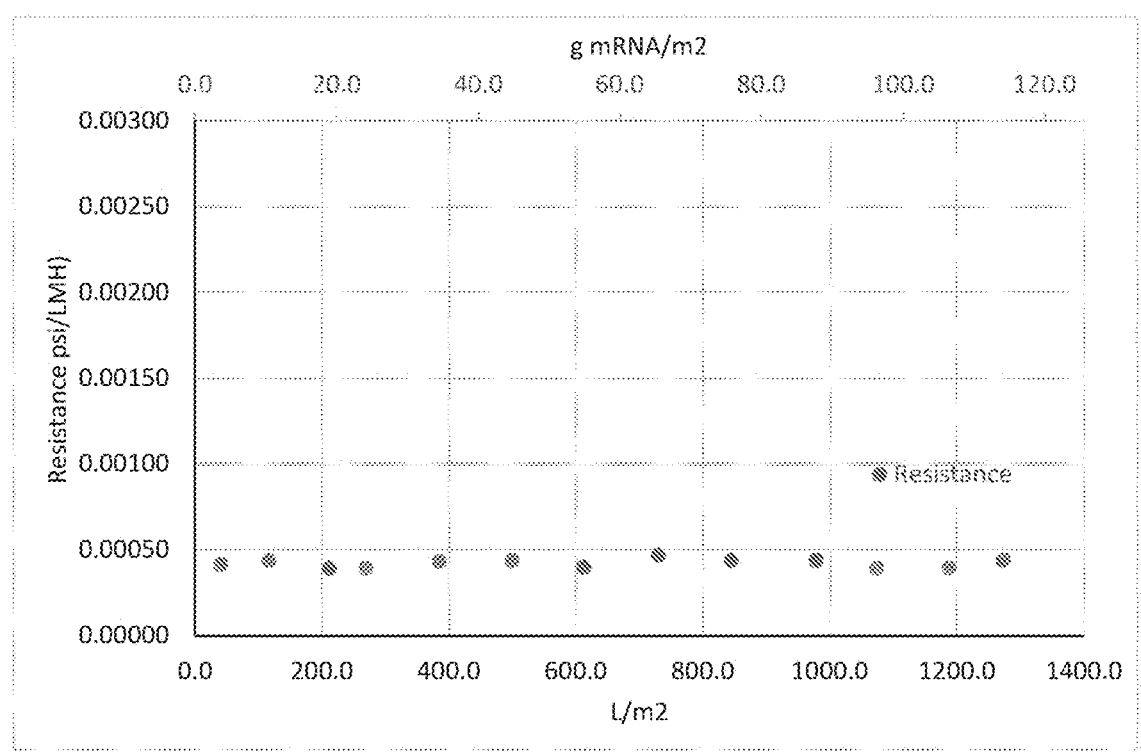
FIG. 5 demonstrates change in filter resistance with respect to the amount of mRNA loaded onto the filter after a second precipitation (Precipitation 2) of CFTR mRNA.
Figure 6:
FIG. 6 shows a photograph of the filtrates from mRNA loading and washing in an exemplary study using depth filtration, (left—filtrate from mRNA capping and tailing reaction (C/T) precipitated a first time (Precipitation 1) and captured by the filter matrix before dissolving the precipitate and collecting the dissolved mRNA in filtrate; right—filtrate from mRNA in Precipitation 1 precipitated a second time (Precipitation 2) captured by the filter matrix before dissolving the precipitate and collecting the dissolved mRNA in filtrate).

The trend of resistance vs. mRNA loading for the C/T Precipitations 1 and 2 are show in FIGS. 4 and 5, respectively. Minimal, if any, increase in resistance was observed during the loading step. The filtrate from the load and washing steps was inspected for the presence of precipitates. As shown in FIG. 6, no precipitates were observed in the filtrate in both the cases.

Figure 7:
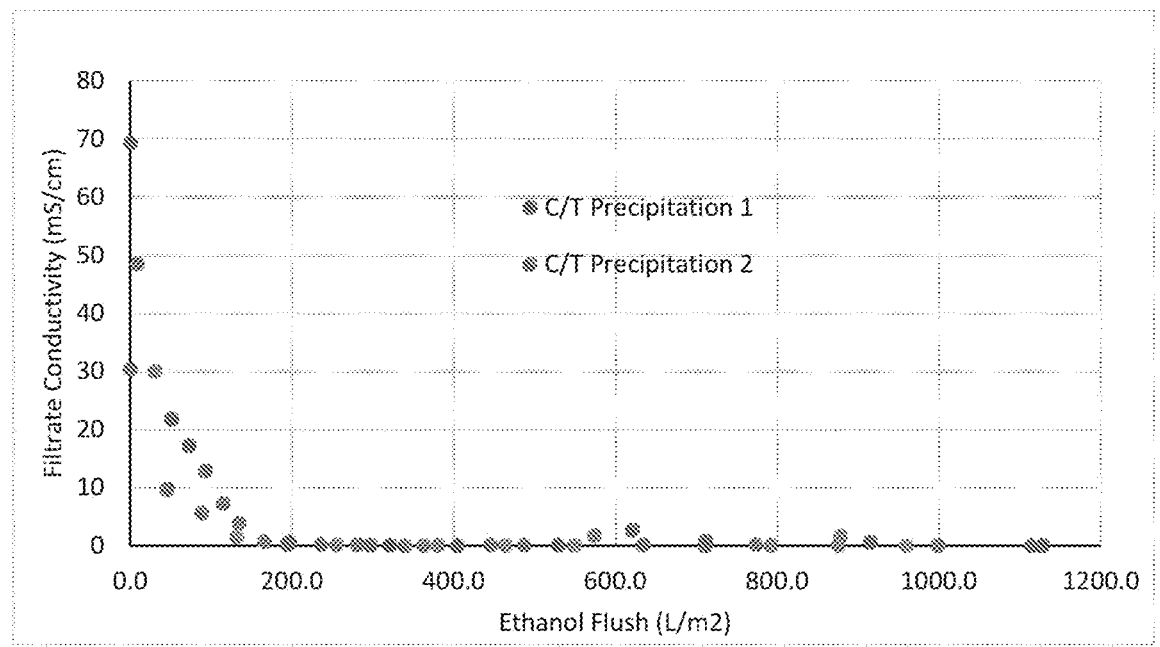
FIG. 7 shows a plot of Filtrate Conductivity over 80% Ethanol Flush Volume of Precipitation 1 and Precipitation 2. The figure demonstrates reduction of filtrate conductivity with increasing volume of ethanol flushes during the exemplary depth filtration of C/T mRNA.

The effectiveness of 80% Ethanol flush to remove residual salt is shown in FIG. 7. The 80% Ethanol effectively removed residual salt from the filter and precipitated mRNA. Approximately 9 L of 80% Ethanol per gram of mRNA was flushed through each of the filters prior to mRNA dissolution and recovery.

Figure 8A:
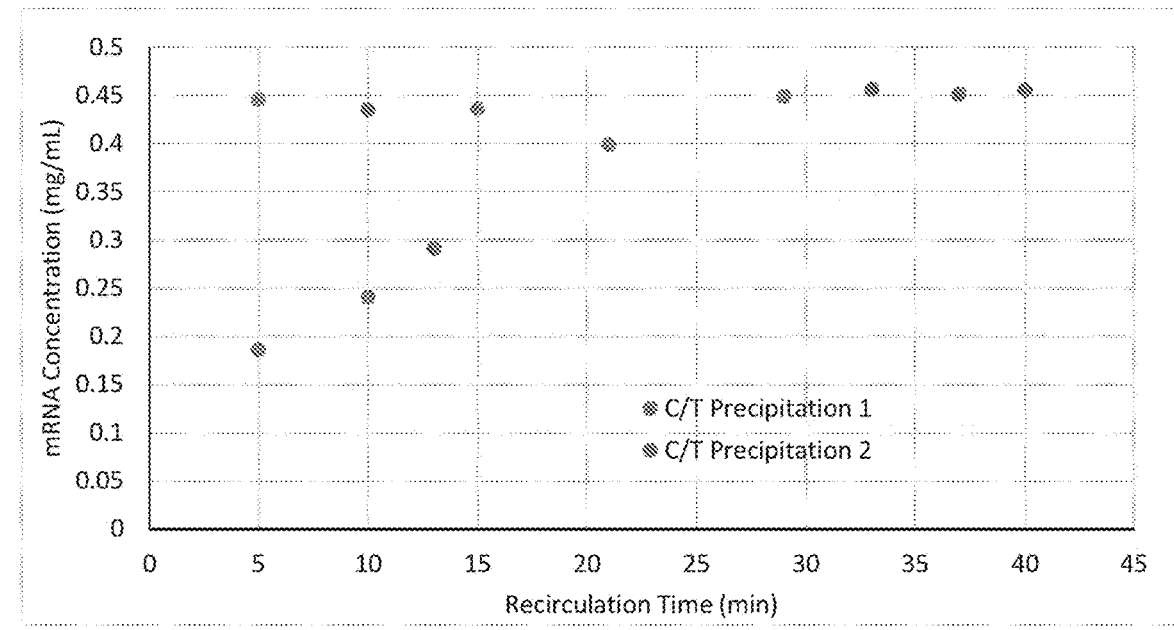
FIG. 8A and FIG. 8B each shows a plot of mRNA concentration over recirculation time for Precipitation 1 and Precipitation 2 after C/T.
Figure 8B:
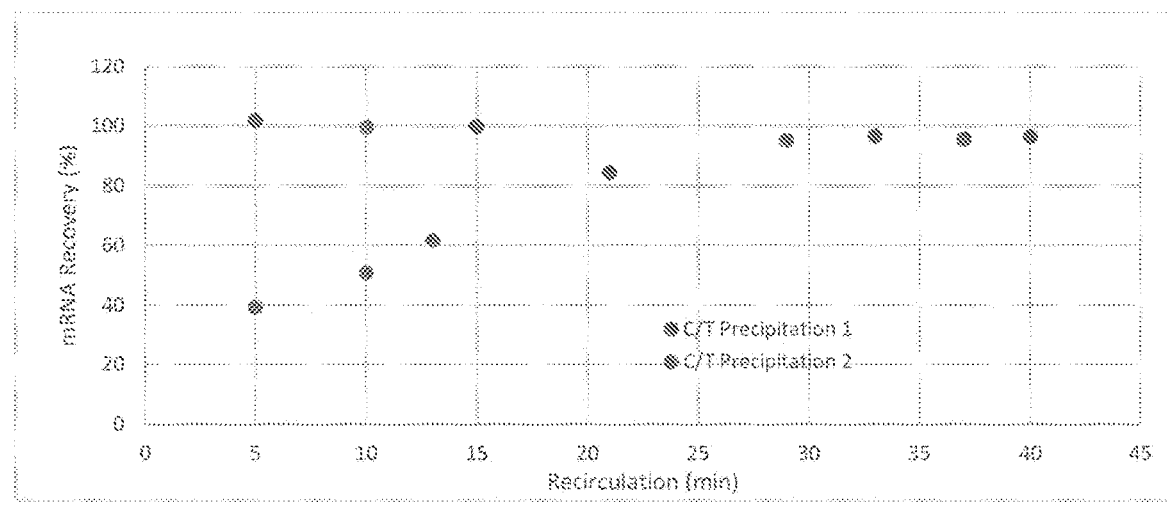

Precipitated mRNA post C/T reaction was successfully dissolved and recovered from the depth filter, further indicating that the precipitated mRNA was retained within the depth filter media and that the 80% Ethanol flush was effective in both maintaining mRNA in its precipitated state captured on and/or within the filter and in removing salt contaminants. The product recovery during recirculation is shown in FIGS. 8A-B and summarized in Table 2, summarizing the recovery mass and percentage.

TABLE 2

Summary of Product Recovery

|  | C/T Precipitation 1 | C/T Precipitation 2 |
|---|---|---|
| Starting Mass | 289 mg* | 270 mg |
| Recovered Mass: | 274 mg | 269 mg |
| % Recovery: | 95% | 100% |

*Starting mass assumes a 10% increase from C/T reaction concentration based on expected tail length.

Figure 9:
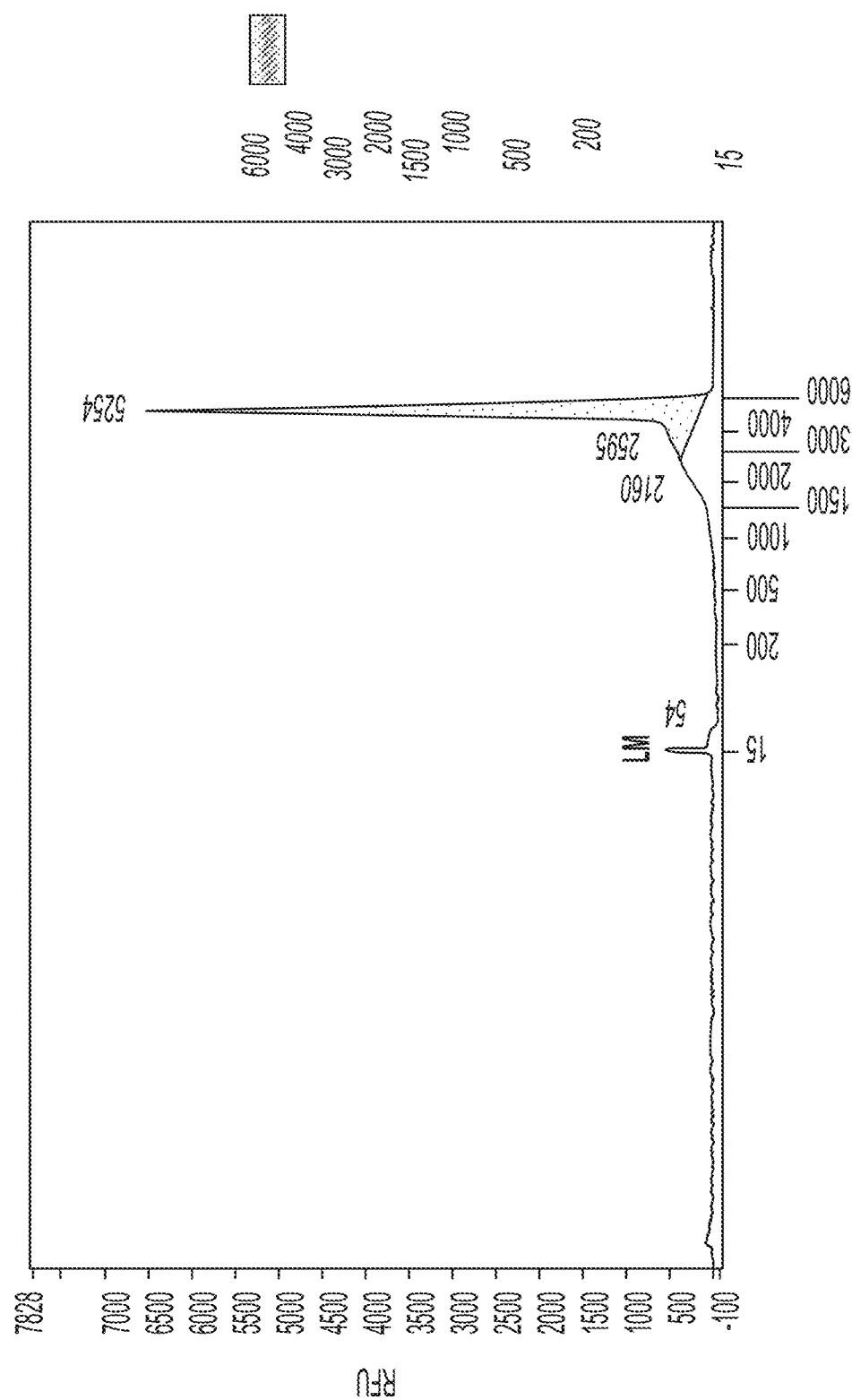
FIG. 9 shows capillary electrophoresis of C/T mRNA purified by depth filtration.

An assessment of the mRNA integrity was performed by examining an aliquot of the recovered purified mRNA using capillary electrophoresis. The results indicate high degree of purity and integrity as shown in FIG. 9. A single peak with no significant shoulder was observed. This indicates that the depth filter process successfully removed contaminants (e.g., shortmers) and at the same time did not adversely impact mRNA quality and integrity, rather it resulted in a highly purified mRNA with high level of mRNA integrity.

Figure 10:
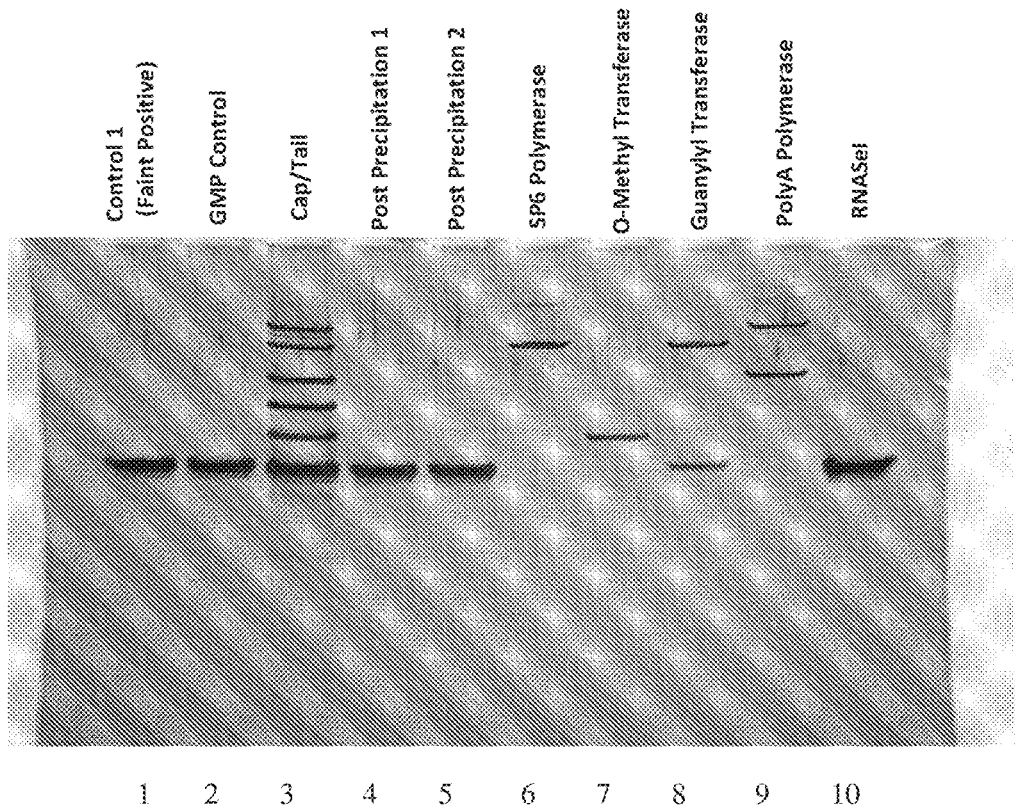
FIG. 10 shows purity of the mRNA by gel electrophoresis of RNAse 1 digested purified product and silver staining the gel to visualize remnant protein contaminants. Lane 1 is positive control, and Lane 2 is negative control. Lane 3 is the C/T mRNA before purification, similarly digested with RNase 1. Lanes 4-5 are purified mRNA products after first and second rounds of filtration respectively of the mRNAs from Precipitation 1 and Precipitation 2. Lanes 6-10 are controls for contaminant proteins expected from the IVT and C/T reactions of the process to make mRNA.

Analysis of the mRNA purity was further assessed by digesting the mRNA product with RNase I and visualizing the remaining contaminants by electrophoresing the digested products in a gel and visualizing with silver stain. Silver stain is sensitive to small amounts of protein in the composition and thus can detect even low amounts of residual capping enzymes or tailing enzyme. As shown in FIG. 10, lanes 4 and 5, the precipitated and filtered mRNA products were free of proteins, similar to lanes 2, which is a negative control of highly pure mRNA. No residual enzymes corresponding to the enzyme in lanes 6-10 were observed. This indicates that use of normal flow filtration as described herein is effective in removing salts and enzymes used in the manufacture of mRNA to produce a highly pure mRNA product.

Example 3. Evaluation of Normal Flow Filtration for the Large-Scale mRNA Purification In this experiment, a depth filter was used to perform normal flow filtration for purification of 15 grams of IVT synthesized CFTR mRNA. A summary of the process steps is described in Table 3.

TABLE 3

15 g CFTR mRNA Batch Manufacturing Process

| Process Step | Description |
|---|---|
| IVT Reaction | In vitro transcription reaction |
| IVT Purification | GSCN and Ethanol Precipitation. Capture, wash, and re-dissolve using depth filter (Clarisolve 60HX). |
| IVT UF/DF | Concentration and buffer exchange via diafiltration and ultrafiltration. |
| C/T | Capping and Tailing reaction. |
| C/T Purification 1 | GSCN and Ethanol Precipitation. Capture, wash, and re-dissolve using depth filter (Clarisolve 60HX). |
| C/T Purification 2 | GSCN and Ethanol Precipitation. Capture, wash, and re-dissolve using depth filter (Clarisolve 60HX). |
| C/T UF/DF | Concentration and buffer exchange via diafiltration and ultrafiltration. |
| Sterile Filter and Fill | Sterile Filtration, Fill in PETG bottles, and Store at ≤−20° C. |

For the normal flow filtration purification of the 15 grams of mRNA, a Clarisolve 60HX depth filter of 0.11 m$^2$, Process Scale Module (CS60HX01F1-X) was used, particularly for the capture and washing of the precipitated mRNA. mRNA loading was done at about 130 g/m$^2$.

Figure 11:
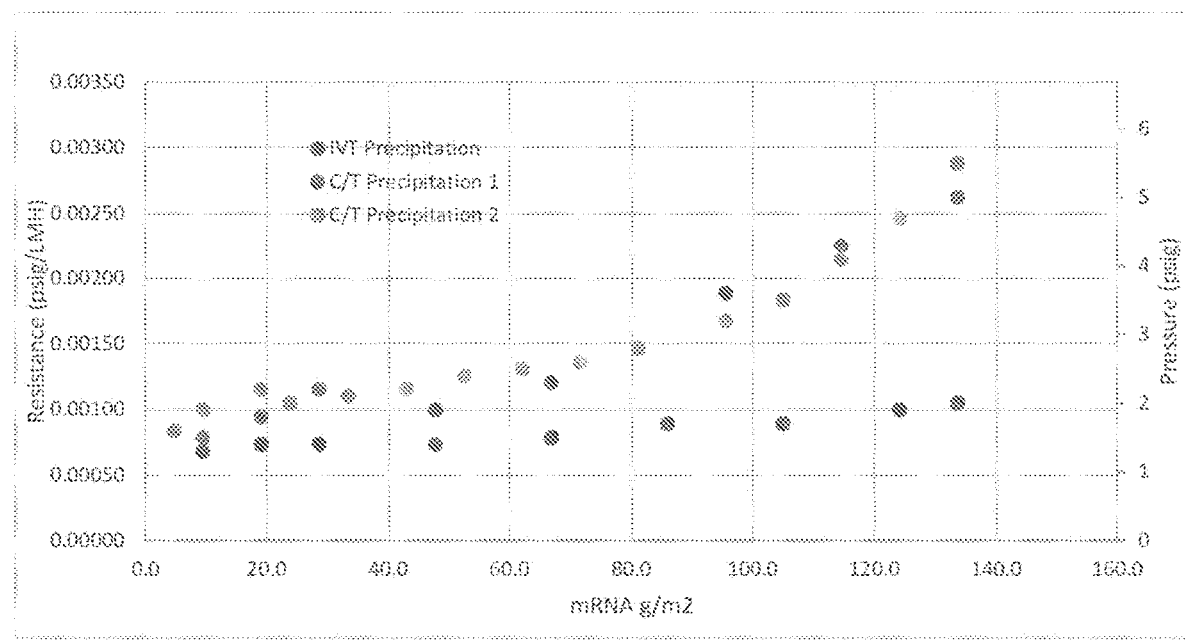
FIG. 11 demonstrates change in filter resistance with respect to the amount of mRNA loaded onto the filter for the IVT reaction, the first precipitation reaction (Precipitation 1) and second precipitation (Precipitation 2) after VT and C/T reactions to make CFTR mRNA.

The trends of resistance vs. mRNA loading for all three precipitations are shown in FIG. 11. Since all precipitations were loaded at the same flux, pressure drop was also included in the trends.

Figure 12:
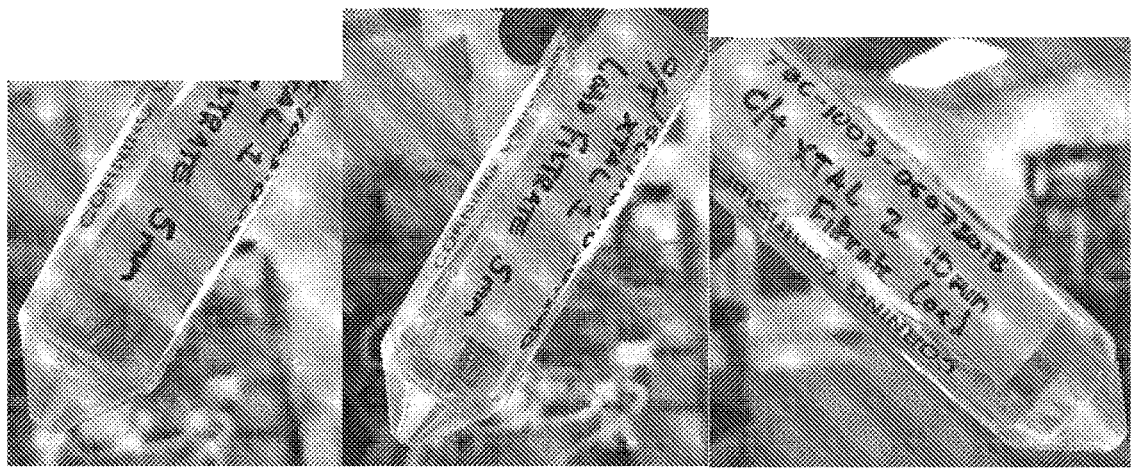
FIG. 12 demonstrates that the filtrates from three filtration runs in depth filter ((1) the VT reaction product, (2) Precipitation 1 following C/T reaction and (3) Precipitation 2 following Precipitation 2) were free of any precipitates. From Left to Right: (1) IVT, (2) C/T 1 Precipitation, and (3) C/T 2 Precipitation.
Figure 13:
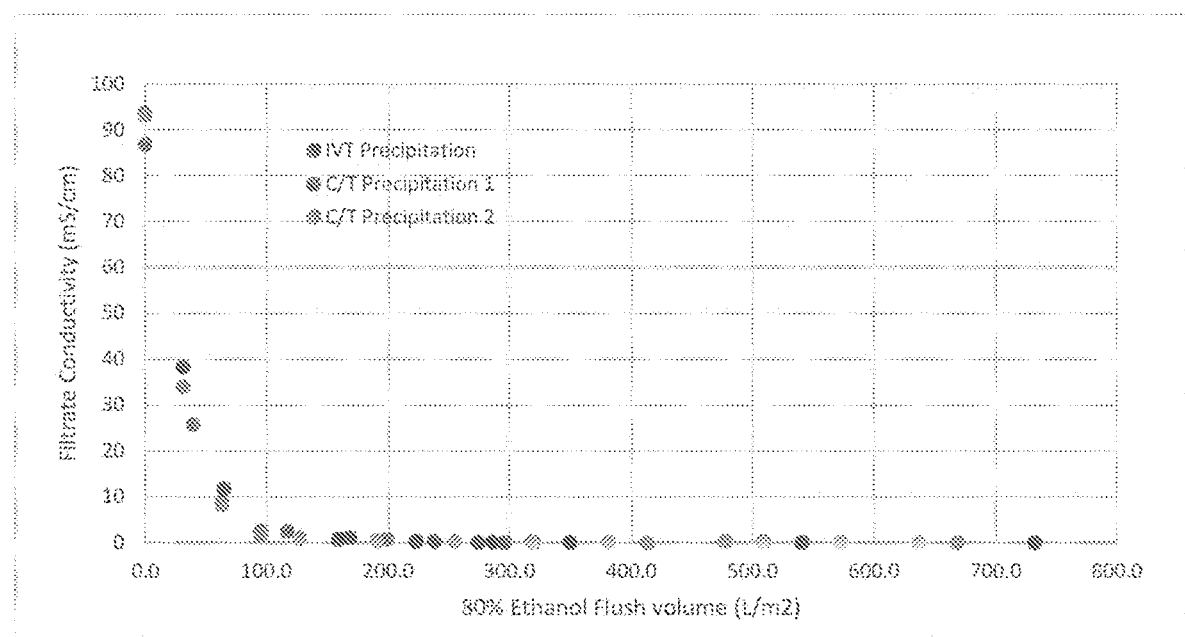
FIG. 13 shows filtrate conductivity plotted against 80% ethanol flush volume (L/m2) in purification of 15 g scale IVT batch preparation of CFTR mRNA.

The 15 grams of CFTR mRNA was precipitated, loaded into the filter system, captured on and/or in the filter, washed using GSCN/Ethanol buffer followed by 80% Ethanol buffer, and then dissolved into filtrate as described above. The filtrate from the load and washing steps (where precipitated mRNA was retained in the filter) was inspected for the presence of precipitates. Photographs of the filtrate from the load are shown in FIG. 12. No precipitates were observed in the filtrates. The effectiveness of 80% Ethanol flush to remove residual salt is shown in FIG. 13 for all three precipitation steps. A filtrate conductivity of 0.0 mS/cm was achieved after approximately 3 L of 80% Ethanol per gram of mRNA. A total of 5 L/g of 80% Ethanol was flushed prior to recirculation. Ethanol flush volumes required to reach 0.0 mS/cm were comparable to the small scale runs. The 80% Ethanol flush effectively removed residual salt from the filter and precipitated mRNA, as indicated in FIG. 13.

Figure 14A:
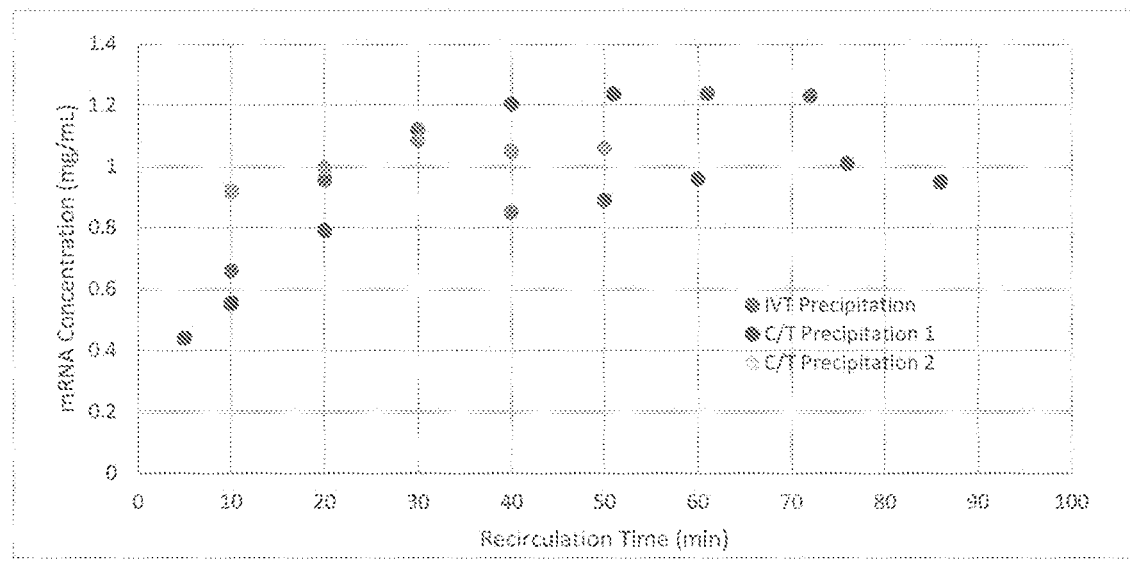
FIG. 14A and FIG. 14B each shows the recovery of mRNA against recirculation time at elution step during the purification of 15 g scale VT batch preparation of CFTR mRNA.
Figure 14B:
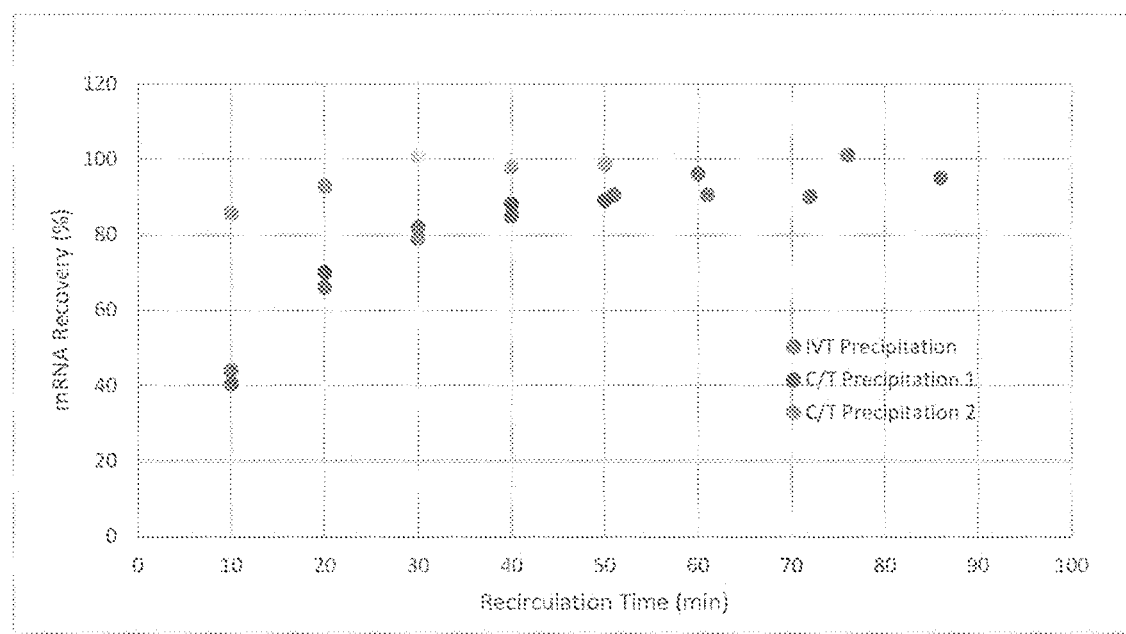

Next, the mRNA was dissolved by switching to a water flush, which was recirculated, as described above. Recovery of the re-dissolved mRNA during recirculation is shown in FIGS. 14A-B. FIG. 14A shows the concentration of mRNA recovered over time. FIG. 14B indicates the % recovery of mRNA over time. The mRNA concentrations stabilized after 30-60 minutes of recirculation, after which mRNA was recovered as filtrate. Precipitated mRNA was successfully re-dissolved and recovered from the depth filter after each of the precipitations, further indicating that the product was successfully captured within the depth filter media during the 80% Ethanol flushes.

Table 4 summarizes the yield of the mRNA at each filtration step. The starting mass assumes a 10% increase from C/T reaction concentration based on expected tail length. A total of 15.4 g of mRNA was produced from the 15 g IVT. This kind of recovery was surprising and unexpected; and was considerably better than the typical processes used in the art, which for a starting mass of 15 g mRNA would be expected to yield approximately 8-10 g of mRNA.

TABLE 4

Yield Summary

| Step Description | mRNA Mass (g) | Step Yield (%) |
| --- | --- | --- |
| IVT Reaction | N/M | N/A |
| IVT Precipitation 1 | 16.0 | N/A |
| IVT UFDF | 16.3 | 102% |
| C/T Reaction | N/M | N/A |
| C/T Precipitation 1* | 16.1 | 90% |
| C/T Precipitation 2 | 15.7 | 98% |
| C/T UFDF | 15.4 | 98% |

*Yield calculations assume a 10% increase in mass resulting from the addition of the tail.

Figure 15A:
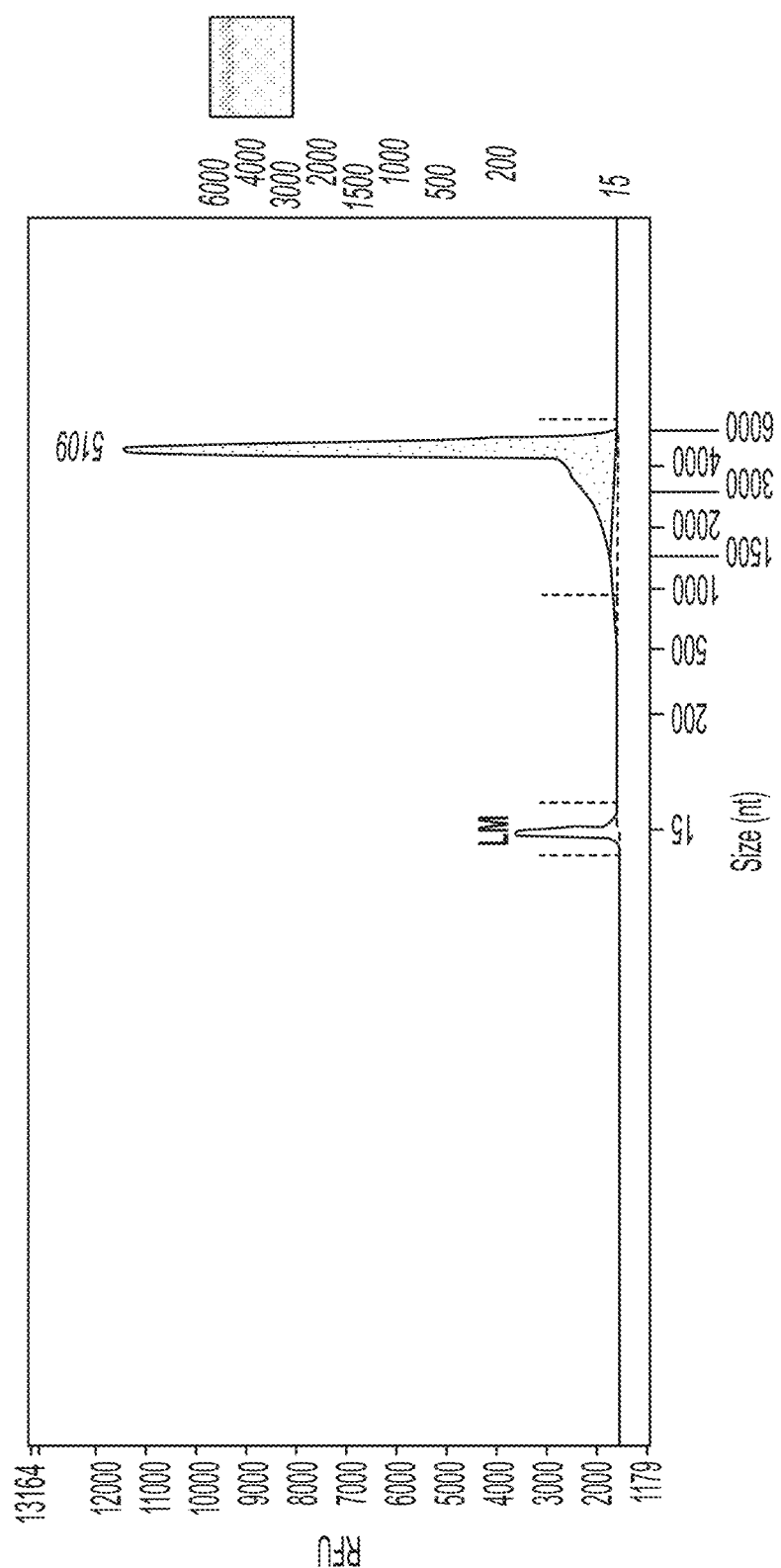
FIG. 15A and FIG. 15B shows electropherogram obtained by capillary electrophoresis of purified 15 g IVT batch purified CFTR mRNA.
Figure 15B:
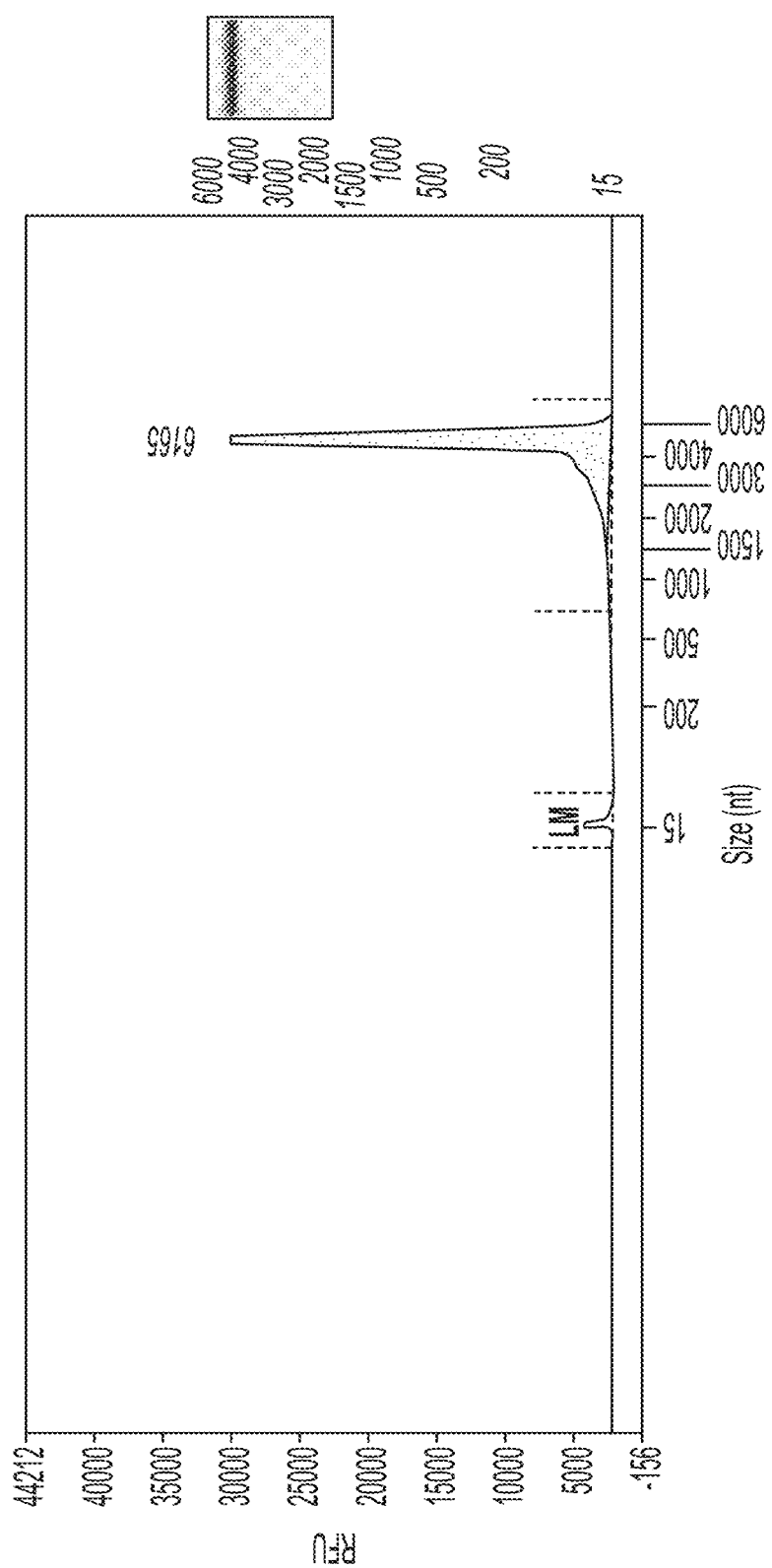

The quality of the purified mRNA was assessed by capillary electrophoresis. The electropherogram assessing mRNA integrity and tail length is shown in FIGS. 15A and 15B. An example of a high integrity control sample, in which CFTR mRNA product was purified earlier by a method without using depth filtration is shown in FIG. 15A. FIG. 15B shows an electropherogram of the depth filter eluted mRNA after two post C/T precipitations, and the result was better than the high integrity control sample. No significant shoulder was observed. The depth filter process did not adversely impact mRNA quality and integrity.

The results of smear analysis are shown in Table 5. The smear analysis of the depth filter batch indicates that mRNA quality was comparable to previously manufactured batches of mRNA by other methods.

TABLE 5

CE Smear Analysis

| Lot Number | Sample Description | Main Peak (%) | Shoulder (%) |
| --- | --- | --- | --- |
| Depth Filter purified mRNA | Drug Substance—Depth Filter | 78 | 21 |
| Control mRNA | Drug Substance— Control Sample | 70 | 28 |

Further, the tail length analysis and the capping efficiency were evaluated for the purified mRNA sample. The tail length analysis is summarized in Table 6. The construct size and tail length are consistant with expectations, indicating that depth filter purification did not adversely affect the capping reaction. The results of the capping assay are shown in Table 7. The cap percentage was consistent with expectations, indicating that depth filter purification did not adversely affect the tailing reaction.

TABLE 6 mRNA Tail Length Analysis

| Sample | Average Size (nt) | Tail Length (nt) |
| --- | --- | --- |
| IVT | 4649 | N/A |
| Drug Substance | 5141 | 492 |

TABLE 7 mRNA Capping Analysis

| Uncapped | 5 |
| --- | --- |
| Cap 0 | 0 |
| Cap G | 0 |
| Cap 1 | 95 |

Figure 16:
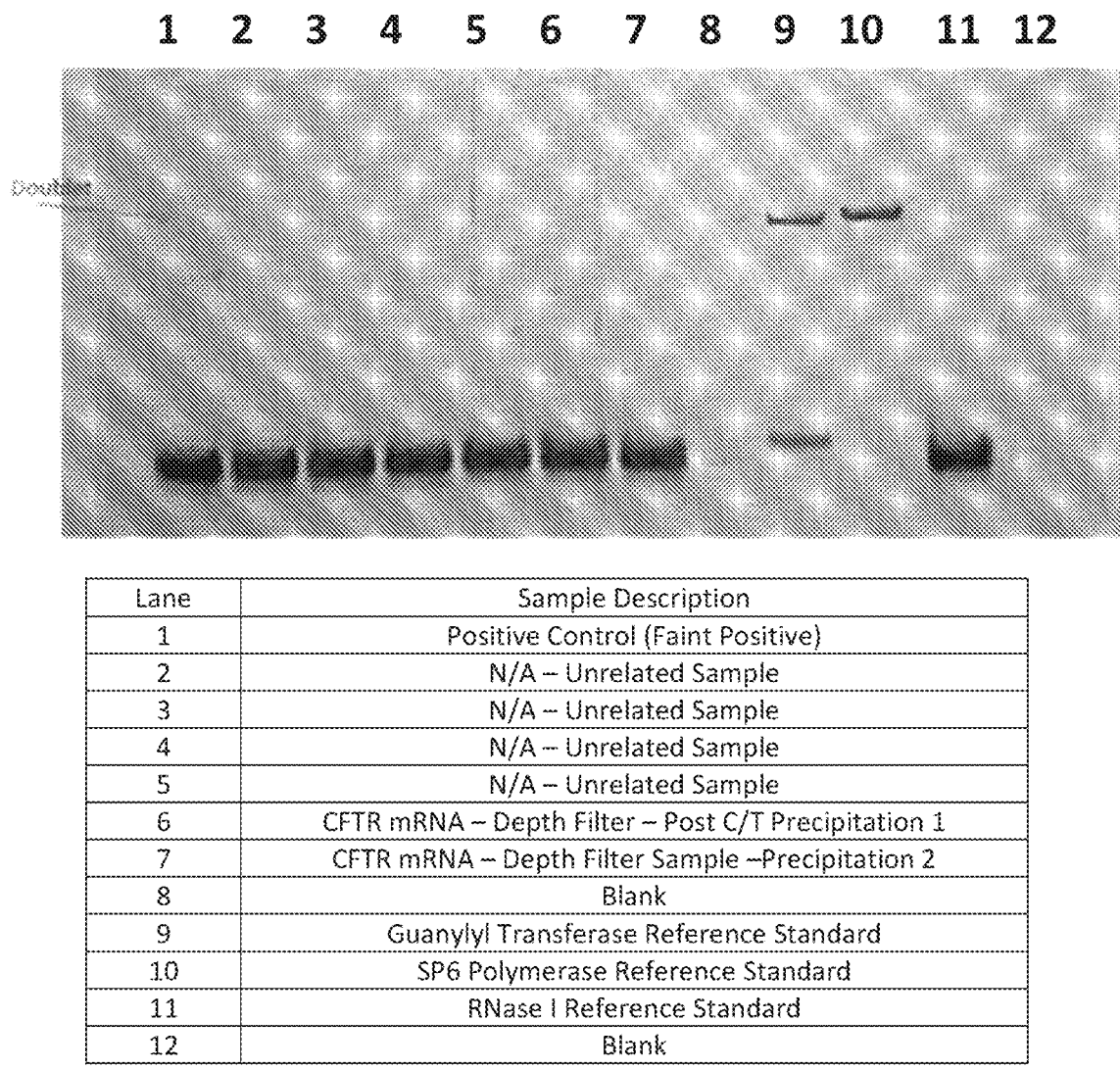
FIG. 16 shows a silver stain analysis assessing mRNA purity and residual enzymes used in the manufacture of the mRNA, including capping enzyme, polymerase enzyme, and RNase enzyme. No residual enzymes were observed in material purified via normal flow filtration after the first precipitation and second precipitation.

The silver stain analysis assessing mRNA purity and residual enzymes is shown in FIG. 16. The mRNA purity was assessed after the first C/T precipitation as well as the second CIT precipitation (drug substance), shown in lanes 6 and 7 respectively. No residual enzymes bands were observed for material purified via depth filtration after the first precipitation and second precipitation. The silver stain indicated that the sample post-CIT precipitation 1 was free of residual enzyme.

To summarize, these results indicate that the depth filter effectively captured, washed, and recovered large-scale amounts of mRNA after each of the IVT and CIT reactions. Step yields for each of the two C/T normal flow filtrations exceeded 90%. The integrity of mRNA manufactured using the normal flow filtration purification process as described herein was consistent with expectations and reference standard quality, indicating that the depth filter purification did not have an adverse impact on integrity. It additionally showed that the depth filter-based purification process did not have an adverse impact on the capping and tailing reactions. Cap percentages and tail lengths were within consistent with references. Finally, no residual capping or tailing enzyme bands were detected after Precipitation 1 or Precipitation 2 indicating the depth filter was effective for facilitating the removal of these enzymes, as well as salt and short abortive RNA species.

In sum, this example demonstrates that large-scale amounts of mRNA, e.g., CFTR mRNA, purified using a normal flow filtration process as described herein has high purity and integrity, and may be produced in a large scale suitable for clinical use.

Example 4. Evaluation of Normal Flow Filtration for 100 g Batch mRNA Purification In this experiment, a depth filter was used to perform normal flow filtration to purify 100 grams of IVT synthesized and capped and tailed (C/T) CFTR mRNA. A summary of the overall process steps is described in Table 8, with the normal flow filtration purification performed in each of the Purification steps (i.e., for IVT Purification and C/T Purification steps in Table 8).

TABLE 8

100 g CFTR mRNA Batch Manufacturing Process

| Process Step | Description |
|---|---|
| IVT Reaction | In vitro transcription reaction |
| IVT Purification | 5M GSCN and Ethanol Precipitation. Capture, wash, and re-dissolve using depth filter (Clarisolve 60HX). |
| IVT UF/DF | Concentration and buffer exchange via diafiltration and ultrafiltration. |
| C/T | Capping and Tailing reaction. |
| C/T Purification | 5M GSCN and Ethanol Precipitation. Capture, wash, and re-dissolve using depth filter (Clarisolve 60HX). |
| C/T UF/DF | Concentration and buffer exchange via diafiltration and ultrafiltration. |
| Sterile Filter and Fill | Sterile Filtration, Fill in PETG bottles, and Store at ≤−20° C. |

At the start of each purification step (i.e., IVT Purification and C/T Purification) mRNA was precipitated to a fine precipitate in suspension by addition of 5 M GSCN buffer followed by Ethanol. The precipitated mRNA was then transferred to the normal flow filtration system for purification. For each of the Purification steps, purification of 100 grams of mRNA was achieved using 0.66 m$^2$ of Clarisolve 60HX depth filter (2×0.33 m$^2$ process scale modules, CS60HX03F1-X), with the mRNA load on the filter being approximately 150 g/m$^2$.

For each purification step, the 100 grams of CFTR mRNA was (1) precipitated, (2) loaded into the filter system where the precipitated mRNA was captured by the filter, (3) washed on the filter using 80% Ethanol buffer, and then (4) dissolved into filtrate, which included recirculation of mRNA through the filter system. The 80% Ethanol wash removed all residual salt from the mRNA, as evidenced by a filtrate conductivity of 0.0 mS/cm with approximately 3 L of 80% Ethanol wash per gram of mRNA.

The mRNA was dissolved into filtrate by switching to a water flush, which was recirculated for approximately 60 minutes to maximize recovery, after which mRNA was recovered as filtrate.

For the 100 g batch of CFTR mRNA purified using the normal flow filtration described above, a final amount of 97.9 grams of the purified mRNA was recovered (e.g., across all steps in Table 8). This 97.9% recovery of purified mRNA was surprising and unexpected, especially at these high mass amounts of mRNA being processed.

The quality of the purified mRNA was assessed by several metrics, including by silver stain gel to measure residual enzyme and protein content, by capillary gel electrophoresis to measure mRNA integrity, and by known techniques to measure percent capping and poly A tail length. Those results are shown below in Table 9.

TABLE 9

Quality of Purified 100 g CFTR mRNA

| Scale (g) | Yield (g) | Yield (%) | Residual Enzyme (gel) | mRNA Integrity (CGE) | Cap1 % | Tail Length (nt) |
|---|---|---|---|---|---|---|
| 100 g | 97.9 g | 97.9 | Conforms to reference | 52.7% (conforms to reference) | 100% | N/A |

To summarize, these results indicate that the depth filter effectively captured, washed, and recovered a 100 g batch of mRNA. The yield of mRNA exceeded 95%. The integrity of mRNA manufactured using the normal flow filtration purification process as described herein was consistent with expectations and reference standard quality, indicating that the depth filter purification did not have an adverse impact on integrity. It additionally showed that the depth filter-based purification process did not have an adverse impact on the capping and tailing reactions. Cap percentages and tail lengths were consistent with references. Finally, no residual capping or tailing enzyme bands were detected in the purified mRNA, indicating the depth filter was effective for facilitating the removal of these enzymes, as well as salt and short abortive RNA species, from a 100 gram batch of mRNA. In sum, this example demonstrates that a 100 gram batch of mRNA, e.g., CFTR mRNA, can be purified using a normal flow filtration process as described herein to a level of high purity and integrity suitable for clinical use.

Example 5: Evaluation of Normal Flow Filtration Purification of MUT mRNA

In this experiment, normal flow filtration using depth filtration for purification of messenger RNA (mRNA) coding for methylmalonyl-CoA mutase protein (MUT) was evaluated. 15 grams of MUT mRNA was manufactured using steps described in Table 10 below with two normal flow filtration steps using a Clarisolve 60HX depth filter. Critical quality attributes of the purified MUT mRNA were used to evaluate the process performance and final drug substance profile.

TABLE 10

15 g MUT mRNA Batch Manufacturing Process

| Process Step | Description |
|---|---|
| IVT Reaction | In vitro transcription reaction |
| IVT Purification | 5M GSCN and Ethanol Precipitation. Capture, wash, and re-dissolve using depth filter (Clarisolve 60HX). |
| IVT UF/DF | Concentration and buffer exchange via diafiltration and ultrafiltration. |
| C/T | Capping and Tailing reaction. |
| C/T Purification | 5M GSCN and Ethanol Precipitation. Capture, wash, and re-dissolve C/T mRNA using depth filter (Clarisolve 60HX). |
| C/T UF/DF | Concentration and buffer exchange via diafiltration and ultrafiltration. |
| Sterile Filter and Fill | Sterile Filtration, Fill in PETG bottles, and Store at ≤−20° C. |

For each of the IVT Purification and the C/T Purification steps, the mRNA loading filters are described in Table 11 below.

TABLE 11 mRNA Loading During Purification Steps

| Parameters | IVT Purification (uncapped mRNA) | C/T Purification (capped and tailed mRNA) |
|---|---|---|
| Depth Filter Cat # | CS60HX01F1-X | CS60HX01F1-X |
| Total Surface Area (m$^2$): | 0.11 | 0.11 |
| mRNA Loaded (g) | 15.0 | 18.6 |
| Scaled Load (g/m$^2$) | 136 | 169 |

Purification of the mRNA using the depth filter in each purification step involved three processes following precipitation of the mRNA: (1) loading of precipitated mRNA, (2) washing of the captured mRNA and (3) elution of mRNA from the membrane. Results of each individual process is further described below.

(1) Loading of Precipitated mRNA

Manufactured mRNA (uncapped and capped) is first denatured and precipitated in GSCN/Ethanol solution at a defined ratio under continuous mixing condition for a desired amount of time followed by pumping the precipitated solution through the pre-conditioned Clarisolve 60HX depth filter device to capture the precipitated mRNA on the filter membrane. Filtrate samples were collected at frequent intervals and no loss of precipitated mRNA was observed.

(2) 80% Ethanol Wash to Remove Buffer and Salts

Figure 17:
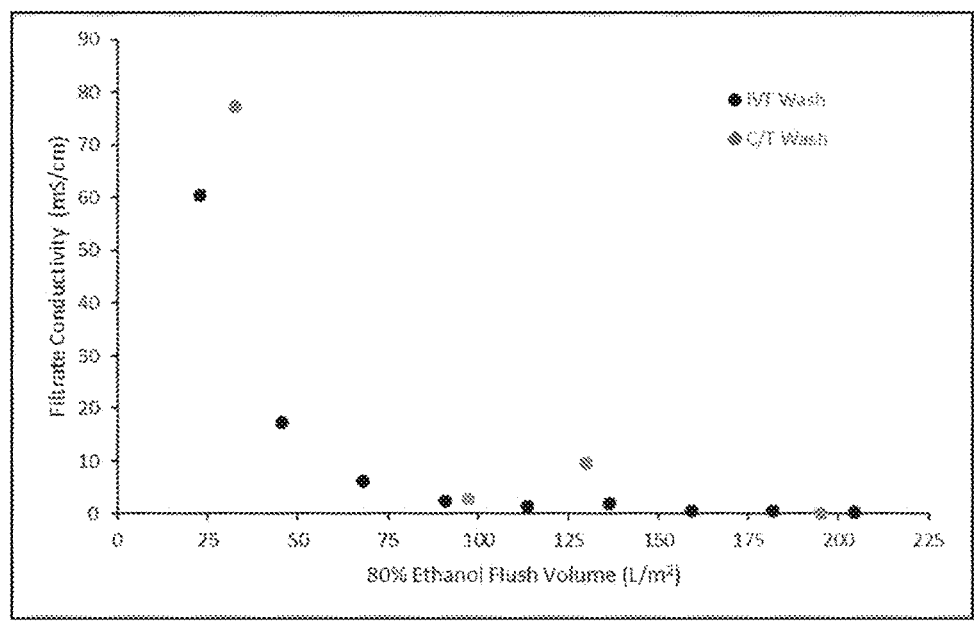
FIG. 17 shows the measure of residual salt, as measured by filtrate conductivity, with successive wash volumes of the 80% v/v ethanol solution from normal flow filtration purification steps for a 15 g batch manufacturing of MUT mRNA.

For each of the IVT Purification and the C/r Purification steps, following the loading of precipitated mRNA, the filter system was rinsed with 80% v/v ethanol solution to remove the buffer salts and other process residual enzymes. FIG. 17 provides the measure of residual salt, as measured by filtrate conductivity, with successive wash volumes of the 80% v/v ethanol solution. The trends in removal of residual salt were consistent across both the purification steps. A filtrate conductivity of 0.0 mS/cm was achieved after approximately 2.5 L/g of 80% ethanol. A total of 1.5 L/g of 80% ethanol was flushed prior to recirculation. Ethanol flush volumes required to reach 0.0 mS/cm were comparable to previous small-scale runs. This demonstrates that this 80% ethanol flush effectively removed residual salt from the filter and precipitated mRNA.

(3) Recovery of mRNA

Figure 18A:
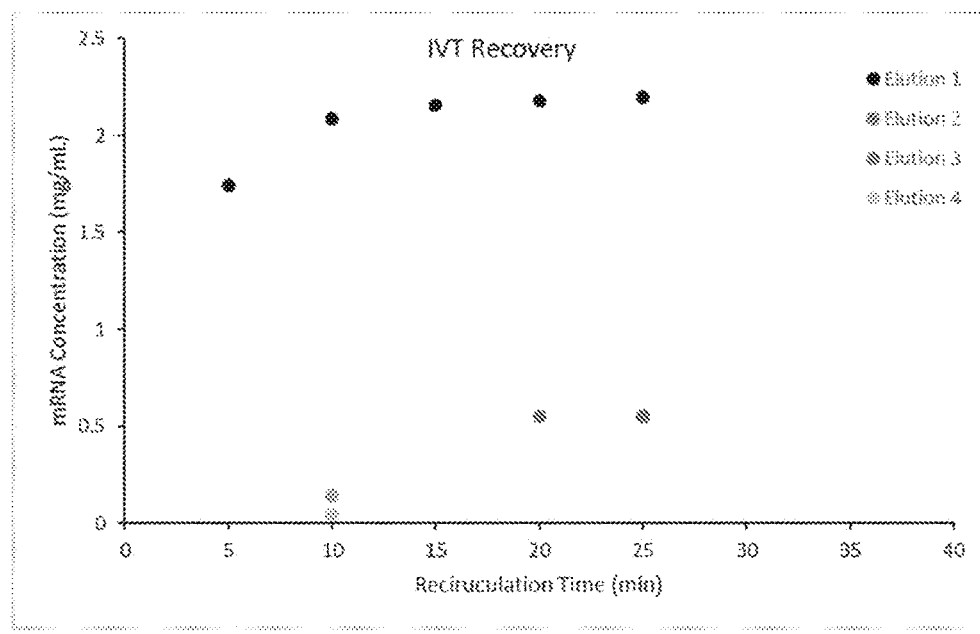
FIG. 18A and FIG. 18B show the recovery of mRNA (in terms of concentration) in the filtrate as a function of recirculation time from normal flow filtration purification of IVT manufactured mRNA, which is uncapped and untailed (FIG. 18A), and from normal flow filtration purification of following capping and tailing (C/T) the mRNA (FIG. 18B).
Figure 18B:
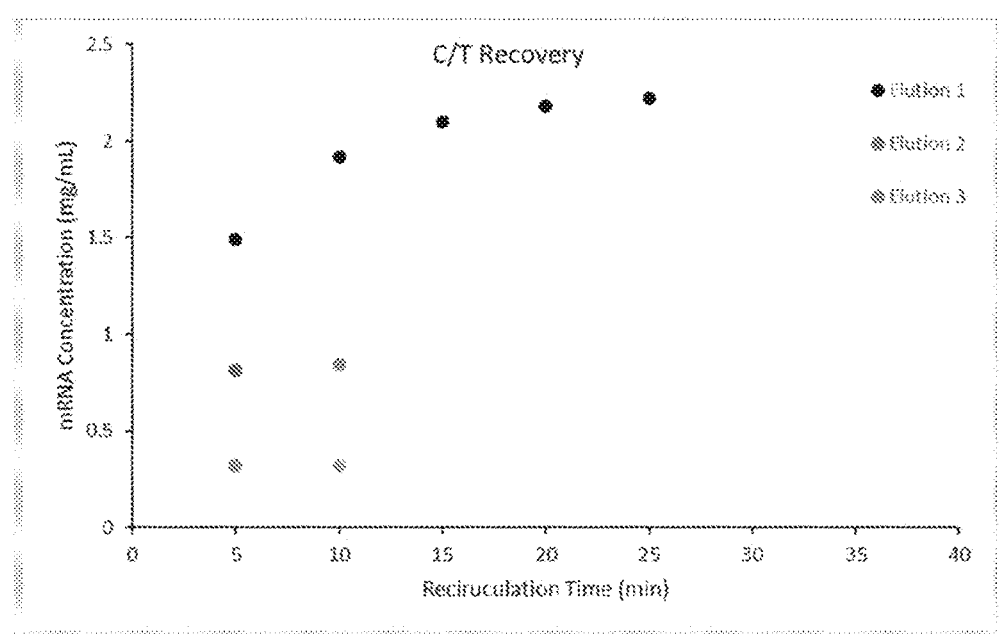

For each of the IVT Purification and the C/T Purification steps, recovery of mRNA from the depth filter was performed by recirculating RNase Free Water at 37° C., with frequent measurement of mRNA concentration of the filtrate pool to determine the point of saturation. Upon reaching the saturation level, the filtrate pool was replaced with a fresh RNase Free Water to elute the remaining mRNA. This step was performed until the concentration of mRNA in the filtrate pool was negligible. FIG. 18A and FIG. 18B show the recovery of mRNA (in terms of concentration) in the filtrate as a function of recirculation time.

As shown in the figures, the filtrate mRNA concentrations stabilized after 25 minutes of recirculation. This shows that precipitated mRNA was successfully re-dissolved and recovered from the depth filter after each of the precipitations, further indicating that the product was retained within the depth filter media and the effectiveness of the 80% ethanol flushes.

mRNA Yield

The total yield for mRNA across all manufacturing process steps as described in Table 10 exceeded 95%, based on a starting target mass of mRNA from the IVT reaction of 15 g of mRNA and assuming a 10% increase in mass after the CIT reaction due to the addition of the cap and 3' tail.

Figure 19:
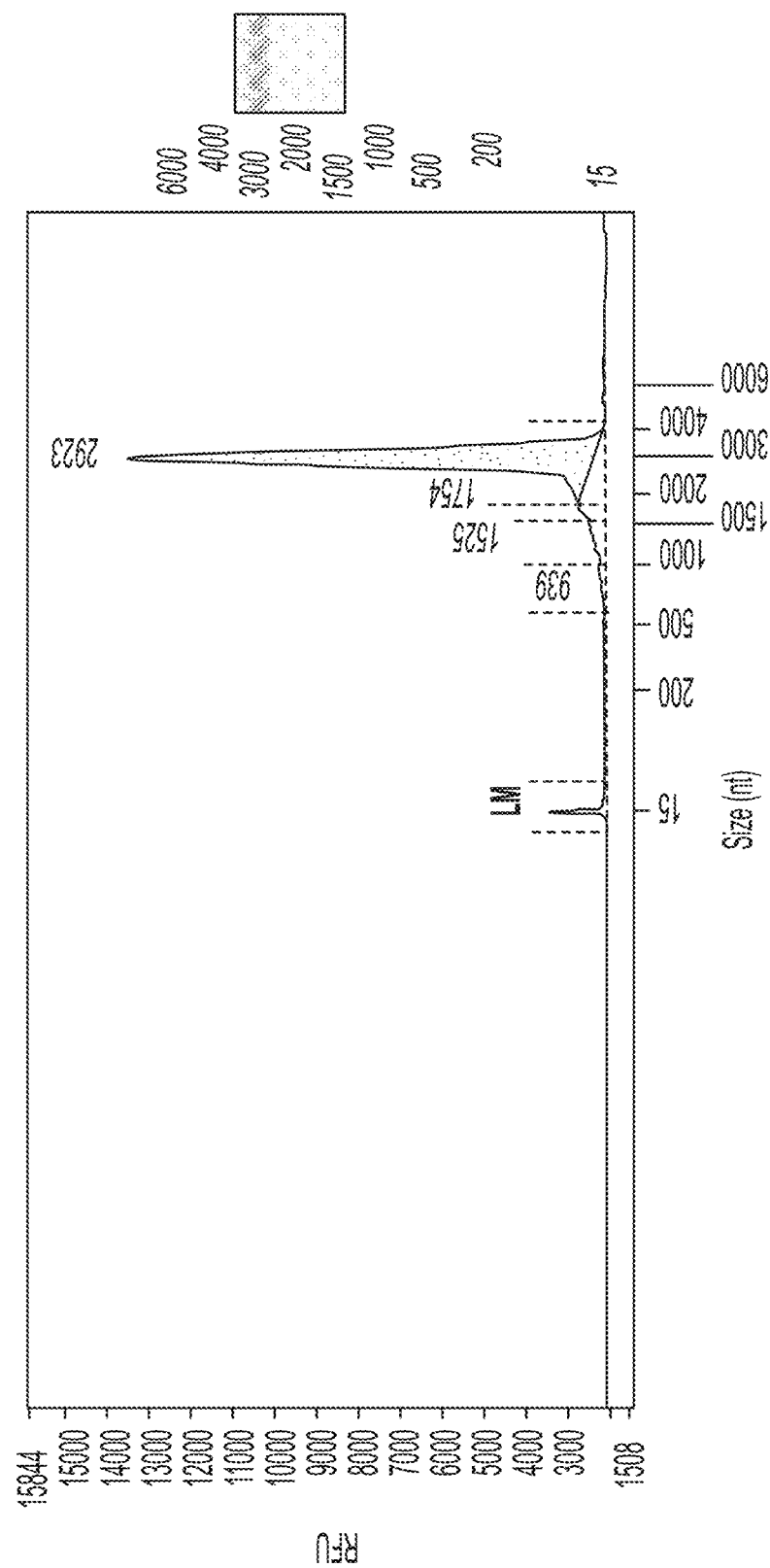
FIG. 19 shows mRNA integrity of MUT mRNA assessed by capillary gel electrophoresis (CGE) analysis following normal flow filtration of the mRNA according to the present invention.

Analytical Results The quality of the purified mRNA was assessed by several metrics, including by capillary gel electrophoresis (CGE) to measure mRNA integrity, by known techniques to measure percent capping and poly A tail length. The electropherogram assessing integrity and tail length of the MUT mRNA following the manufacture that included the two normal flow filtration steps as described in Table 10 is shown in FIG. 19. The electropherogram for the depth filter material after two precipitations (IVT and CIT) was consistent with expectations. No significant shoulder was observed, thereby indicating that the depth filter process did not adversely impact mRNA quality and integrity. The results of the smear analysis are shown below in Table 12.

TABLE 12

Smear Analysis of Purified MUT mRNA Drug Substance

| Sample Description | Main Peak (%) | Shoulder (%) |
|---|---|---|
| Drug Substance—Depth Filter | 80 | 18 |
| Control Sample | 78 | 20 |

The tail length analysis is summarized is Table 13. The construct size and tail length are consistent with expectations.

TABLE 13

Tail Length Analysis of MUT mRNA Drug Substance

| Sample | Average Size (nt) | Tail Length (nt) |
|---|---|---|
| IVT | 2577 | N/A |
| Drug Substance | 2923 | 380 |

The results of the capping assay are shown in Table 14. The cap percentage was consistent with expectations.

TABLE 14

Capping Efficiency for MUT mRNA Drug Substance

| Cap Species | Percentage (%) |
|---|---|
| Uncapped | 5 |
| Cap 0 | 0 |
| Cap G | 0 |
| Cap 1 | 95 |

Figure 20:
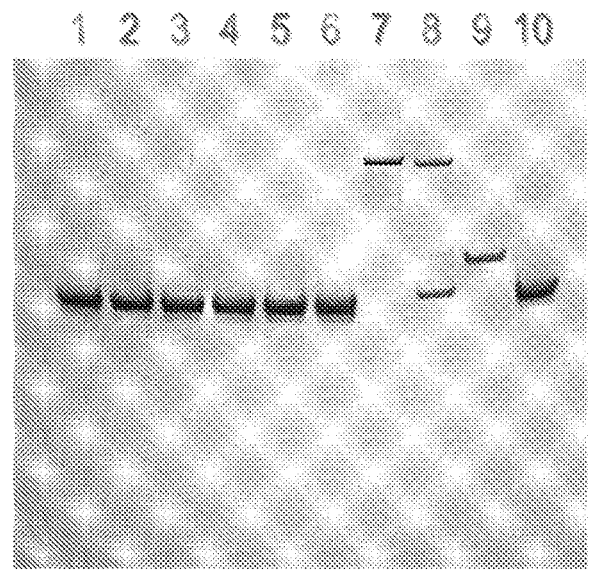
FIG. 20 shows a silver stain gel of purified MUT mRNA with controls and reference enzymes used in the manufacture of the mRNA and removed by the normal flow filtration process described herein.

The silver stain analysis assessing mRNA purity and residual enzymes is shown in FIG. 20. No residual enzymes bands were observed for material purified via depth filtration after the C/f precipitation (Lanes 3-6) at both 1 mg/mL and 2 mg/mL concentration, thereby indicating the efficiency of depth filter process in removing residual enzymes.

In summary, the depth filter effectively captured, washed, and recovered mRNA after the IVT and C/T reactions to yield a highly pure mRNA drug substance. The overall process yield with these purification steps exceeded 95%.

The integrity of mRNA manufactured by a depth-filter based purification process was consistent with expectation and reference standards, indicating that the depth filter purification did not have an adverse impact on integrity. In addition, the depth-filter based purification process did not have an adverse impact on the capping and tailing reactions. Cap percentages and tail lengths were within expectations and analytical specifications. Moreover, residual enzyme bands were detected after precipitation step indicating the depth filter was effective in facilitating the removal of residual process enzymes thereby improving the purity of mRNA.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. A method for large scale purification of messenger RNA (mRNA), the method comprising the steps of:

(a) precipitating mRNA from a solution comprising one or more contaminants from manufacturing the mRNA to provide a suspension comprising precipitated mRNA;
(b) subjecting the suspension comprising the precipitated mRNA to a depth filter, wherein the suspension flows in a direction perpendicular to the surface of the filter and precipitated mRNA is retained by the filter, comprising pore sizes ranging from 400 µm to 5 µm;
(c) dissolving the precipitated mRNA retained by the filter in step (b) thereby allowing purified mRNA to pass through the filter; and
(d) recovering the purified mRNA from step (c);
wherein each of steps (b), and (c) is conducted using normal flow filtration, and wherein at least 10 grams of mRNA is purified by the method in a single batch.

2. The method of claim 1, wherein the manufacturing comprises in vitro transcription (IVT) synthesis of the mRNA prior to step (a).

3. The method of claim 1, wherein the manufacturing comprises a step of 5'-capping of the mRNA prior to step (a).

4. The method of claim 1, wherein the manufacturing comprises a step of 3'-tailing of the mRNA prior to step (a).

5. The method of claim 1, wherein the one or more contaminants comprise an enzyme.

6. The method of claim 5, wherein the enzyme is a polymerase or a capping enzyme.

7. The method of claim 1, wherein the one or more contaminants comprise a salt.

8. The method of claim 1, wherein the one or more contaminants comprise short abortive transcripts.

9. The method of claim 1, further comprising a step of washing the precipitated mRNA retained on the filter from step (b).

10. The method of claim 1, wherein the filter is made of an inert material.

11. The method of claim 1, wherein no dispersant is added to the suspension.

12. The method of claim 1, wherein the mRNA encodes a protein or a peptide.

13. The method of claim 1, wherein the total purified mRNA recovered from the method is recovered in an amount that results in a yield of about 85%.

14. The method of claim 1, wherein the total purified mRNA is recovered in an amount that results in a yield of about 90%.

15. The method of claim 1, wherein the purified mRNA has a clinical grade purity without further purification.

16. The method of claim 15, wherein the purified mRNA comprises 5% or less of protein contaminants as determined by capillary electrophoresis.

17. The method of claim 1, wherein the purified mRNA has integrity of 95% or greater as determined by capillary electrophoresis.

18. A method of purifying a composition comprising 100 gm or more of mRNA manufactured by in vitro transcription (IVT) synthesis, the method comprising:
precipitating the IVT-transcribed mRNA comprising one or more contaminants from the IVT synthesis to generate a suspension;
subjecting the suspension comprising the precipitated mRNA and contaminants to normal flow filtration through a filter, where the precipitated mRNA is retained by the filter;
recovering the mRNA from the filter in a solution, thereby purifying the mRNA,
wherein at least 85% of the mRNA is recovered and the recovered mRNA has integrity of 90% or greater and is substantially free of protein contaminants.

19. The method of claim 1, wherein at least 100 grams of mRNA is purified by the method in a single batch.

20. The method of claim 1, wherein at least 250 grams of mRNA is purified by the method in a single batch.

21. The method of claim 1, wherein at least 500 grams of mRNA is purified by the method in a single batch.

22. The method of claim 1, wherein at least 1 kilogram of mRNA is purified by the method in a single batch.

23. The method of claim 1, wherein the depth filter has a surface area of or greater than 264 m$^2$.

24. The method of claim 1, wherein the depth filter has a surface area of or greater than 1056 m$^2$.

25. The method of claim 1, wherein the depth filter has a surface area of or greater than 2112 m$^2$.

* * * * *